US007371763B2

(12) United States Patent
Dumas et al.

(10) Patent No.: US 7,371,763 B2
(45) Date of Patent: May 13, 2008

(54) INHIBITION OF RAF KINASE USING QUINOLYL, ISOQUINOLYL OR PYRIDYL UREAS

(75) Inventors: Jacques Dumas, Orange, CT (US); Bernd Riedl, Wuppertal (DE); Uday Khire, Hamden, CT (US); Robert N. Sibley, North Haven, CT (US); Holia Hatoum-Mokdad, Hamden, CT (US); Mary-Katherine Monahan, Hamden, CT (US); David E. Gunn, Hamden, CT (US); Timotthy B. Lowinger, Nishinomiya (JP); William J. Scott, Guilford, CT (US); Roger A. Smith, Madison, CT (US); Jill E. Wood, Hamden, CT (US)

(73) Assignee: Bayer Pharmaceuticals Corporation, West Haven, CT (US)

( * ) Notice: Subject to any disclaimer, the term of this patent is extended or adjusted under 35 U.S.C. 154(b) by 2 days.

(21) Appl. No.: 11/158,048

(22) Filed: Jun. 22, 2005

(65) Prior Publication Data
US 2006/0019990 A1    Jan. 26, 2006

Related U.S. Application Data

(63) Continuation of application No. 10/125,369, filed on Apr. 19, 2002, now abandoned.

(60) Provisional application No. 60/367,376, filed on Apr. 20, 2001.

(51) Int. Cl.
C07D 401/02 (2006.01)
A61K 31/44 (2006.01)
A61K 31/47 (2006.01)

(52) U.S. Cl. ............... 514/310; 514/313; 514/332; 546/143; 546/159; 546/255

(58) Field of Classification Search ................ 546/143, 546/159, 255; 514/310, 313, 332
See application file for complete search history.

(56) References Cited

U.S. PATENT DOCUMENTS

| 502,504 | A | 8/1893 | Thoms |
|---|---|---|---|
| 1,742,156 | A | 2/1931 | Fritzky |
| 2,046,375 | A | 7/1936 | Goldstein et al. |
| 2,093,265 | A | 9/1937 | Coffey et al. |
| 2,288,422 | A | 6/1942 | Rohm |
| 2,649,476 | A | 8/1953 | Martin |
| 2,683,082 | A | 7/1954 | Hill et al. |
| 2,722,544 | A | 11/1955 | Martin |
| 2,745,874 | A | 5/1956 | Schetty et al. |
| 2,781,330 | A | 2/1957 | Downey |
| 2,797,214 | A | 6/1957 | Bossard |
| 2,867,659 | A | 1/1959 | Model et al. |
| 2,877,268 | A | 3/1959 | Applegate et al. |
| 2,960,488 | A | 11/1960 | Tamblyn et al. |
| 2,973,386 | A | 2/1961 | Weldon |
| 3,151,023 | A | 9/1964 | Martin |
| 3,200,035 | A | 8/1965 | Martin et al. |
| 3,230,141 | A | 1/1966 | Frick et al. |
| 3,424,760 | A | 1/1969 | Helsley et al. |
| 3,424,761 | A | 1/1969 | Helsley et al. |
| 3,424,762 | A | 1/1969 | Helsley et al. |
| 3,547,940 | A | 12/1970 | Brantley |
| 3,646,059 | A | 2/1972 | Brantley |
| 3,689,550 | A | 9/1972 | Schellenbaum et al. |
| 3,743,498 | A | 7/1973 | Brantley |
| 3,754,887 | A | 8/1973 | Brantley |
| 3,823,161 | A | 7/1974 | Lesser |
| 3,828,001 | A | 8/1974 | Broad et al. |
| 3,860,645 | A | 1/1975 | Nikawitz |
| 3,990,879 | A | 11/1976 | Soper |
| 4,001,256 | A | 1/1977 | Callahan et al. |
| 4,009,847 | A | 3/1977 | Aldrich et al. |
| 4,042,372 | A | 8/1977 | Harper |
| 4,062,861 | A | 12/1977 | Yukinaga et al. |
| 4,071,524 | A | 1/1978 | Banitt |
| 4,111,680 | A | 9/1978 | Yukinaga et al. |
| 4,111,683 | A | 9/1978 | Singer |
| 4,116,671 | A | 9/1978 | Yukinaga et al. |
| 4,173,637 | A | 11/1979 | Nishiyama et al. |
| 4,173,638 | A | 11/1979 | Nishiyama et al. |
| 4,183,854 | A | 1/1980 | Crossley |
| 4,212,981 | A | 7/1980 | Yukinaga et al. |
| 4,240,820 | A | 12/1980 | Dickore et al. |
| 4,279,639 | A | 7/1981 | Okamoto et al. |
| 4,405,644 | A | 9/1983 | Kabbe et al. |
| 4,410,697 | A | 10/1983 | Török et al. |
| 4,437,878 | A | 3/1984 | Acker et al. |
| 4,468,380 | A | 8/1984 | O'Doherty et al. |
| 4,473,579 | A | 9/1984 | Devries et al. |
| 4,511,571 | A | 4/1985 | Böger et al. |
| 4,514,571 | A | 4/1985 | Nakai et al. |
| 4,526,997 | A | 7/1985 | O'Doherty et al. |
| 4,623,662 | A | 11/1986 | De Vries |
| 4,643,849 | A | 2/1987 | Hirai et al. |
| 4,740,520 | A | 4/1988 | Hallenbach et al. |

(Continued)

FOREIGN PATENT DOCUMENTS

CA    2146707    10/1995

(Continued)

OTHER PUBLICATIONS

European Office Action mailed Mar. 2, 2005 of EP Patent Application No. 02 725 710.4-2101, filed Apr. 18, 2002.

(Continued)

*Primary Examiner*—Zinna N. Davis
(74) *Attorney, Agent, or Firm*—Millen, White, Zelano, Branigan, P.C.

(57) ABSTRACT

The invention relates to a group of quinolyl, isoquinolyl and pyridyl ureas, their the use in treating raf mediated diseases, and pharmaceutical compositions which contain these ureas for use in such therapy.

37 Claims, No Drawings

U.S. PATENT DOCUMENTS

| | | |
|---|---|---|
| 4,760,063 A | 7/1988 | Hallenbach et al. |
| 4,808,588 A | 2/1989 | King |
| 4,820,871 A | 4/1989 | Kissener et al. |
| 4,863,924 A | 9/1989 | Haga et al. |
| 4,973,675 A | 11/1990 | Israel et al. |
| 4,983,605 A | 1/1991 | Kondo et al. |
| 4,985,449 A | 1/1991 | Haga et al. |
| 5,036,072 A | 7/1991 | Nakajama et al. |
| 5,059,614 A | 10/1991 | Lepage et al. |
| 5,098,907 A | 3/1992 | Kondo et al. |
| 5,130,331 A | 7/1992 | Pascual |
| 5,162,360 A | 11/1992 | Creswell et al. |
| 5,185,358 A | 2/1993 | Creswell |
| 5,312,820 A | 5/1994 | Ashton et al. |
| 5,319,099 A | 6/1994 | Kamata et al. |
| 5,399,566 A | 3/1995 | Katano et al. |
| 5,423,905 A | 6/1995 | Fringeli |
| 5,429,918 A | 7/1995 | Seto et al. |
| 5,432,468 A | 7/1995 | Moriyama et al. |
| 5,447,951 A | 9/1995 | Politi et al. |
| 5,447,957 A | 9/1995 | Adams et al. |
| 5,470,882 A | 11/1995 | Dixon et al. |
| 5,500,424 A | 3/1996 | Nagamine et al. |
| 5,508,288 A | 4/1996 | Forbes et al. |
| 5,559,137 A | 9/1996 | Adams et al. |
| 5,596,001 A | 1/1997 | Hamanaka |
| 5,597,719 A | 1/1997 | Freed et al. |
| 5,696,138 A | 12/1997 | Olesen et al. |
| 5,698,581 A | 12/1997 | Kleemann et al. |
| 5,773,459 A | 6/1998 | Tang et al. |
| 5,780,483 A | 7/1998 | Widdowson et al. |
| 5,807,891 A | 9/1998 | Bold et al. |
| 5,814,646 A | 9/1998 | Heinz |
| 5,886,044 A | 3/1999 | Widdowson et al. |
| 5,891,895 A | 4/1999 | Shiraishi et al. |
| 5,908,865 A | 6/1999 | Doi et al. |
| 5,929,250 A | 7/1999 | Widdowson et al. |
| 5,965,573 A | 10/1999 | Petrie et al. |
| 6,004,965 A | 12/1999 | Breu et al. |
| 6,005,008 A | 12/1999 | Widdowson et al. |
| 6,015,908 A | 1/2000 | Widdowson et al. |
| 6,020,345 A | 2/2000 | Vacher et al. |
| 6,022,884 A | 2/2000 | Mantlo et al. |
| 6,040,339 A | 3/2000 | Yoshida et al. |
| 6,043,374 A | 3/2000 | Widdowson et al. |
| 6,080,763 A | 6/2000 | Regan et al. |
| 6,093,742 A | 7/2000 | Salituro et al. |
| 6,133,319 A | 10/2000 | Widdowson |
| 6,143,764 A | 11/2000 | Kubo et al. |
| 6,147,116 A | 11/2000 | Barbachyn et al. |
| 6,150,415 A | 11/2000 | Hammock et al. |
| 6,174,901 B1 | 1/2001 | Mantlo et al. |
| 6,178,399 B1 | 1/2001 | Takebayashi et al. |
| 6,180,675 B1 | 1/2001 | Widdowson et al. |
| 6,187,799 B1 | 2/2001 | Wood et al. |
| 6,211,373 B1 | 4/2001 | Widdowson et al. |
| 6,218,539 B1 | 4/2001 | Widdowson et al. |
| 6,242,601 B1 | 6/2001 | Breu et al. |
| 6,262,113 B1 | 7/2001 | Widdowson et al. |
| 6,271,261 B1 | 8/2001 | Widdowson |
| 6,310,068 B1 | 10/2001 | Bottcher et al. |
| 6,333,341 B1 | 12/2001 | Mantlo et al. |
| 6,339,045 B1 | 1/2002 | Kanno et al. |
| 6,344,476 B1 | 2/2002 | Ranges et al. |
| 6,391,917 B1 | 5/2002 | Petrie et al. |
| 2002/0062763 A1 | 5/2002 | Macholdt et al. |
| 2002/0065298 A1 | 5/2002 | Dumas et al. |
| 2002/0082255 A1 | 6/2002 | Eastwood |
| 2002/0128321 A1 | 9/2002 | Widdowson et al. |

FOREIGN PATENT DOCUMENTS

| | | |
|---|---|---|
| DE | 0 487 014 | 12/1929 |
| DE | 0 511 468 | 10/1930 |
| DE | 0 523 437 | 5/1931 |
| DE | 583207 * | 8/1933 |
| DE | 2436179 A1 | 2/1975 |
| DE | 2436179 C2 | 2/1975 |
| DE | 25 01 648 | 7/1975 |
| DE | 3305866 A1 | 2/1983 |
| DE | 35 29 247 A1 | 8/1985 |
| DE | 35 40 377 A1 | 11/1985 |
| DE | 0 253 997 | 2/1988 |
| EP | 0016371 A1 | 3/1980 |
| EP | 0107214 A1 | 5/1984 |
| EP | 0116932 | 8/1984 |
| EP | 0192263 B1 | 8/1986 |
| EP | 0202538 A1 | 11/1986 |
| EP | 0230400 A2 | 7/1987 |
| EP | 0233559 B1 | 8/1987 |
| EP | 242666 | 10/1987 |
| EP | 0264904 A2 | 4/1988 |
| EP | 335156 | 3/1989 |
| EP | 371876 | 11/1989 |
| EP | 0359148 A1 | 3/1990 |
| EP | 0379915 A1 | 8/1990 |
| EP | 0380048 A2 | 8/1990 |
| EP | 0381987 A1 | 8/1990 |
| EP | 0 405 233 | 1/1991 |
| EP | 0405233 A1 | 1/1991 |
| EP | 459887 | 5/1991 |
| EP | 676395 | 7/1996 |
| EP | 860433 A1 | 8/1998 |
| FR | 1 457 172 | 9/1966 |
| GB | 0 828 231 | 10/1956 |
| GB | 0 771 333 | 3/1957 |
| GB | 0 921 682 | 3/1963 |
| GB | 1590870 | 6/1981 |
| IR | 36555 | 1/2000 |
| JP | 44 2569 | 2/1969 |
| JP | 50-76072 | 6/1975 |
| JP | 50-77375 | 6/1975 |
| JP | 50-149668 | 11/1975 |
| JP | 51 063170 | 1/1976 |
| JP | 51-80862 | 7/1976 |
| JP | 53 086033 | 7/1978 |
| JP | 54-032468 | 9/1979 |
| JP | 55 98152 | 7/1980 |
| JP | 55-124763 | 9/1980 |
| JP | 55-162772 | 12/1980 |
| JP | 3 532 47 | 3/1991 |
| JP | 8 301841 | 11/1996 |
| JP | 10-306078 | 11/1998 |
| LB | 6124 | 1/2000 |
| WO | 90/02112 | 3/1990 |
| WO | 93/18028 | 9/1993 |
| WO | 93/24458 | 12/1993 |
| WO | 94/14801 | 7/1994 |
| WO | 94/18170 | 8/1994 |
| WO | 94/22807 | 10/1994 |
| WO | 94/25012 | 11/1994 |
| WO | 95/02591 | 1/1995 |
| WO | 95/07922 | 3/1995 |
| WO | 95/13067 | 5/1995 |
| WO | 95/31451 | 11/1995 |
| WO | 95/33458 | 12/1995 |
| WO | 96/10559 | 4/1996 |
| WO | WO 96/13632 | 5/1996 |
| WO | 96/25157 A1 | 8/1996 |
| WO | 96/40673 | 12/1996 |
| WO | 96/40675 A1 | 12/1996 |

| | | |
|---|---|---|
| WO | 97/17329 | 5/1997 |
| WO | 97/29743 | 8/1997 |
| WO | 97/30992 | 8/1997 |
| WO | 97/40028 A1 | 10/1997 |
| WO | 97/45400 | 12/1997 |
| WO | 97/49399 | 12/1997 |
| WO | 97/49400 | 12/1997 |
| WO | 98/17267 | 4/1998 |
| WO | 98/22103 | 5/1998 |
| WO | 98/22432 | 5/1998 |
| WO | 98/52558 | 11/1998 |
| WO | 98/52559 | 11/1998 |
| WO | 99/00357 | 1/1999 |
| WO | 99/00370 | 1/1999 |
| WO | WO 96/20617 | 4/1999 |
| WO | 99/23091 | 5/1999 |
| WO | 99/24398 | 5/1999 |
| WO | WO 99/21835 | 5/1999 |
| WO | WO 99/24635 | 5/1999 |
| WO | 99/32106 | 7/1999 |
| WO | 99/32110 | 7/1999 |
| WO | 99/32111 | 7/1999 |
| WO | 99/32436 | 7/1999 |
| WO | 99/32437 | 7/1999 |
| WO | 99/32455 | 7/1999 |
| WO | 99/32463 | 7/1999 |
| WO | 99/33458 | 7/1999 |
| WO | 99/40673 | 8/1999 |
| WO | 00/43366 A1 | 1/2000 |
| WO | 00/17175 | 3/2000 |
| WO | 00/43384 | 7/2000 |
| WO | WO 00/41698 | 7/2000 |
| WO | WO 00/42012 | 7/2000 |
| WO | WO 0047577 | 8/2000 |
| WO | 00/55139 | 9/2000 |
| WO | 00/55152 | 9/2000 |
| WO | WO 01/36403 A1 | 5/2001 |
| WO | WO 02/24635 | 3/2002 |
| WO | WO 02/24635 A2 | 3/2002 |
| WO | WO 02/42012 | 5/2002 |
| WO | WO 02/062763 | 8/2002 |

OTHER PUBLICATIONS

A "Notice of References Cited" from the USPTO for U.S. Appl. No. 08/995,749, filed Dec. 2, 1998, Inhibition Of P38 Kinase Using Symmetrical And Unsymmetrical Diphenyl Ureas.

A "Notice of References Cited" from the USPTO for U.S. Appl. No. 09/083,399, filed Jan. 8, 2001, Inhibition of Raf Kinase Using Aryl Ureas.

A "Notice of References Cited" from the USPTO for U.S. Appl. No. 09/425,228, filed Sep. 10, 2001, Inhibition of Raf Kinase Using Symmetrical and Unsymmetrical Substituted Diphenyl Ureas.

A "Notice of References Cited" from the USPTO for U.S. Appl. No. 09/425,229, filed Mar. 4, 2002, Omega Carboxy Aryl Substituted Diphenyl Ureas as P38 Kinase Inhibitors.

A "Notice of References Cited" from the USPTO for U.S. Appl. No. 09/458,015, filed Feb. 1, 2002, Inhibition of P38 Kinase Using Symmetrical And Unsymmetrical Diphenyl Ureas.

A "Notice of References Cited" from the USPTO for U.S. Appl. No. 09/472,232, filed Dec. 27, 1999, Inhibition of Raf Kinase Using Aryl and Heteroaryl Substituted Heterocyclic Ureas.

A "Notice of References Cited" from the USPTO for U.S. Appl. No. 09/773,604, filed Feb. 2, 2001, Publication No. US 2001-0034447-A1, Publication Date Oct. 25, 2001, Omega-carboxyaryl Substituted Diphenyl Ureas as Raf Kinase Inhibitors.

A "Notice of References Cited" from the USPTO for U.S. Appl. No. 09/773,659, filed Feb. 2, 2001, W-carboxyaryl Substituted Diphenyl Ureas As Raf Kinase Inhibitors.

A "Notice of References Cited" from the USPTO for U.S. Appl. No. 09/773,672, filed Feb. 2, 2001, Publication No. US 2001-0016659-A1, Publication Date Aug. 23, 2001, Omega-carboxyaryl substituted Diphenyl Ureas as Raf Kinase Inhibitors.

A "Notice of References Cited" from the USPTO for U.S. Appl. No. 09/773,675, filed Feb. 2, 2001, Publication No. US 2001-0011136-A1, Publication Date Aug. 2, 2001, Omega-Carboxyaryl Substituted Diphenyl Ureas as Raf Kinase Inhibitors.

A "Notice of References Cited" from the USPTO for U.S. Appl. No. 09/776,935, filed Dec. 12, 1998, Inhibition Of P38 Kinase Using Aryl and Heteroaryl Substituted Heterocyclic Ureas.

A "Notice of References Cited" from the USPTO for U.S. Appl. No. 09/776,936, filed Dec. 22, 1998, Inhibition of Raf Kinase Using Symmetrical and Unsymmetrical Substituted Diphenyl Ureas.

A "Notice of References Cited" from the USPTO for U.S. Appl. No. 09/777,920, filed Feb. 7, 2002, Omega-Carboxyaryl Substituted Diphenyl Ureas as Raf Kinase Inhibitors.

A "Notice of References Cited" from the USPTO for U.S. Appl. No. 09/948,915, filed Feb. 11, 2002, Omega-Carboxyaryl Substituted Diphenyl Ureas as Raf Kinase Inhibitors.

A "Notice of References Cited" from the USPTO for U.S. Appl. No. 10/042,226, filed Jan. 1, 2002, Omega Carboxyaryl Substituted Diphenyl Ureas as Raf Kinase Inhibitors.

Supplemental search report from the EPO for European application EP 98/963809 dated Mar. 30, 2001, Inhibition of Raf Kinase Using Symmetrical and Unsymmetrical Substituted Diphenyl Ureas, publication No. 1049664, publication date Nov. 8, 2000.

Supplemental search report from the EPO for European application EP 98/963810 dated Dec. 21, 2000, Inhibition of Raf Kinase Using Aryl and Heteroaryl Substituted Heterocyclic Ureas, publication No. 1056725, publication date Dec. 6, 2000.

Supplemental search report from the EPO for European application EP 98/965981 dated Dec. 21, 2000, Inhibition of Raf Kinase Using Substituted Heterocyclic Ureas, publication No. 1047418, publication date Nov. 2, 2000.

Supplemental search report from the EPO for European application EP 00/903239 dated Aug. 7, 2002, Omega-Carboxyaryl Substituted Diphenyl Ureas as Raf Kinase Inhibitors.

International search report for International Application No. PCT/US98/10375 dated Sep. 3, 1998, Inhibition of p38 Kinase Activity by Aryl Ureas, publication No. 98/52558, publication date Nov. 26, 1998.

International search report for International Application No. PCT/US98/10376 dated Jul. 30, 1998, Raf Kinase Inhibitors, publication No. WO 98/52559, publication date Nov. 26, 1998.

International search report for International Application No. PCT/US98/26078 dated Apr. 2, 1999, Inhibition of Raf Kinase Using Substituted Heterocyclic Ureas, publication No. WO99/32106, publication date Jul. 1, 1999.

International search report for International Application No. PCT/US98/26079 dated Apr. 12, 1999, Inhibition of p36 Activity Using Aryl and Heteroaryl Substituted Heterocyclic Ureas, publication No. WO99/32110, publication date Jul. 1, 1999.

International search report for International Application No. PCT/US98/26080 dated Apr. 12, 1999, Inhibition of p38 Kinase Using Substituted Heterocyclic Ureas, publication No. WO99/32111, publication date Jul. 1, 1999.

International search report for International Application No. PCT/US98/26081 dated Apr. 2, 1999, Inhibition of Raf Kinase Using Symmetrical and Unsymmetrical Substituted Diphenyl Ureas, publication No. WO99/32436, publication date Jul. 1, 1999.

International search report for International Application No. PCT/US98/26082 dated May 12, 1999, Inhibition of Raf Kinase Using Aryl and Heteroaryl Substituted Heterocyclic Ureas, publication No. WO99/32455, publication date Jul. 1, 1999.

International search report for International Application No. PCT/US98/24765 dated Mar. 2, 1999, Inhibition Of P38 Kinase Using Aryl and Heteroaryl Substituted Heterocyclic Ureas.

International search report for International Application No. PCT/US00/00648 dated Jun. 29, 2000, Omega-Carboxyaryl Substituted Diphenyl Ureas as Raf Kinase Inhibitors.

International search report for International Application No. PCT/US00/00768 dated May 16, 2000, Omega-Carboxy Aryl Substituted Diphenyl Ureas as P38 Kinase Inhibitors.

International search report for International Application No. PCT/US02/12064 dated Sep. 20, 2002, Omega-Carboxypyridyl Substituted Dephenyl Ureas as Raf Kinase Inhibitors, publication No. 02/085859, publication date Oct. 31, 2002.
International search report for International Application No. PCT/US02/12066 dated Sep. 13, 2002, Inhibition of Raf Kinase Quinolyl, Isoquinolyl or Pyridyl Ureas, publication No. 02/085857, publication date Oct. 31, 2002.
International search report for International Application No. PCT/US/26081 dated Apr. 2, 1999, Inhibition of Raf Kinase Using Symmetrical and Unsymmetrical Substituted Diphenyl Ureas, publication No. WO99/32436, publication date Jul. 1, 1999.
Abstract of EP 202,538 (Nov. 28, 1986).
Abstract of DE 3305886 A (EP equivalent 116,932), R.D. Acker et al., Aug. 23, 1984.
Abstract of EP 116,932, Aug. 29, 1984.
Abstract of EP 16,371, Oct. 1, 1980.
Abstract of EP 4931A (Equivalent 4,240,820), Dickore, K. et al. (1978).
Abstract of EP 0405233A1, Tetsuo Sekiya et al. (Jun. 15, 1989).
Abstract of EP 0 676 395 (U.S. equlvalent 5,698,581), Dec. 16, 1997.
Caplus 113:106314, Abstract of JP 2022650, Silver halide color photographic material containing a cyan coupler of 2-ureido-phenol type to improve dye developability and remove lecuo cyan dye, Noboru Mizukura et al. Jan. 25, 1990.
Caplus 113:142130, Abstract of JP 2023337, Silver halide color photographic material containing phenolic cyan coupler a colorless cyan coupler, Toshihiko Yagi et al., Jan. 25, 1990.
Caplus 87:62295, "The metabolism and toxicity of halogenated carbanilides. Billary metabolites of 3,4,4'-trichlorocarbanilide and 3-trifluoromethyl-4,4'-dichlorocarbanilide in the rat", Chemical Life Science, pp. 157-166, 1977.
Caplus 127:293717, "Optical properties of segmented oligourethane with azomethine terminal fragments", National Academy of Science of Ukraine, M. V, Kurik et al., pp. 2038-2041, 1996.
Caplus 127:273945, "Quantitative structure-biodegradability studies: an investigation of the MITI aromatic compound database", School of Pharmacy and Chemistry, J. C. Dearden, pp. 93-104, 1996.
Caplus 126:166148, "Inhibitors of coenzyme A-Independent transacylase induce apoptosis in human HL-60 cells", James D. Winkler et al., J. Pharmacol. Exp. Ther. pp. 956-966, 1996.
Caplus 98:78152, Abstract of JP 57185219, "Antitumor benzophenone derivatives", Nov. 15, 1982.
Caplus 72:79046, Abstract of CH 479557, "Tuberculostatic and cancerostatic polybasic ureas", Dr. A. Wander, Oct. 15, 1969.
Caplus 125:245169, "Production of murine monoclonal antibodies against sulcofuron and flucofuron by in vitro immunization", G. A. Bonwick et al., J. Immunol. Methods, pp. 163-173, 1996.
Caplus 127:341371, "Preparation of quinoline an dquilazoline derivatives inhibiting platelet-derived growth factor receptor autophosphorylation", Kazuo Kubo et al., May 15, 1997.
Caplus 131:58658, "Inhibition of raf kinase using symmetrical and unsymmetrical substituted diphenly ureas", Miller, Scott, Jul. 1, 1999.
Caplus 131:87909y, "Inhibition of p38 kinase activity using substituted heterocyclic ureas", Jacques Dumas, Jul. 1, 1999.
Caplus 131:73649b, "Preparation of pyrazolyl aryl ureas and related compounds as p38kinase inhibitor", Jacques Dumas, Jul. 1, 1999.
Joseph V. Simone, "Cecil Textbook of Medicine", 20th Edition, vol. 1, Feb. 3, 1997, pp. 1004-1010.
Cesar Raposo et al., "Catalysis of Nucleophilic Addition of Pyrrolidine to 2-(5H)-Furanone through Chromenone Cleft-Type Receptors", vol. 37, No. 38, pp. 6947-6950, 1996.
Jacqueline E. van Muljlwijk-Koezen et al., "Isoquinoline and Quinazoline Urea Analogues as Antagonists for the Human Adenosine $A_3$ Receptor", J. Ed. Chem. 2000, 43, pp. 2227-2238, Jan. 3, 2000.
Jacques Dumas et al., "1-Phenyl-5-pyrazolyl Ureas: Potent and Selective p38 Kinase Inhibitors", Bioorganic & Medicinal Chemistry Letters, pp. 2051-2054, May 2, 2000.
Robert W. Carling et al., "1-(3-Cyanobenxylpiperidin-4-yl)-5-methyl-4-phenyl-1, 3-dihydroimidazol-2-one: A Selective High-Affinity Antagonist for the Human Dopamine $D_4$ Receptor with Excellent Selectivity over Ion Channels", J. Med. Chem., 1999, 42, pp. 2706-2715.
Abstract WO 9822103, May 28, 1998, John Philip Hedge et al.
Abstract of DE 3305866A1, Aug. 29, 1984, Dr. Acker Rolf-Dieter et al.
Abstract of EP 4931 (equivalent 4,240,820), K. Dickore e tal, (1980).
Dumas, J., "CAS Structure," May 6, 1997, pp. 1-29.
Scott,Bill, "Substructure (Patent Families)", Aug. 11, 1997, pp. 1-19.
Scott, Bill, "Substructure #2", Nov. 25, 1997, pp. 1-3.
"Bellstein number" Collection, 28 pages (1997).
"Bellstein Collection", 4 pages (1997).
Scott, Bill, "Substrate Search", Dec. 2, 1997, pp. 1-51.
Substructure Search, pp. 1-30. (1997).
Derwent World Patents Index Search, pp. 20-26. (1997).
Abstract of EP 116,932 (1984).
Abstract of EP 676,395 (1995).
Abstract of EP 202,538 (1986).
Abstract of EP 16,371 (1980).
A "Notice of References Cited" from the USPTO for U.S. Appl. No. 08/995,749.
A "Notice of References Cited" from the USPTO for U.S. Appl. No. 09/083,399.
A "Notice of References Cited" from the USPTO for U.S. Appl. No. 09/425,228.
A "Notice of References Cited" from the USPTO for U.S. Appl. No. 09/425,229.
A "Notice of References Cited" from the USPTO for U.S. Appl. No. 09/458,015.
A "Notice of References Cited" from the USPTO for U.S. Appl. No. 09/472,232.
A "Notice of References Cited" from the USPTO for U.S. Appl. No. 09/773,604.
A "Notice of References Cited" from the USPTO for U.S. Appl. No. 09/773,659.
A "Notice of References Cited" from the USPTO for U.S. Appl. No. 09/773,672.
A "Notice of References Cited" from the USPTO for U.S. Appl. No. 09/773,675.
A "Notice of References Cited" from the USPTO for U.S. Appl. No. 09/776,935.
A "Notice of References Cited" from the USPTO for U.S. Appl. No. 09/776,936.
A "Notice of References Cited" from the USPTO for U.S. Appl. No. 09/777,920.
A "Notice of References Cited" from the USPTO for U.S. Appl. No. 09/948,915.
A "Notice of References Cited" from the USPTO for U.S. Appl. No. 10/042,226.
A "Notice of References Cited" from the EPO fro European application No. EP 98/963809.
Supplemental search report from the EPO for European application EP 98/963810.
Supplemental search report from the EPO for European application EP 98/965981.
Supplemental search report from the EPO for European application EP 00/903239.
International search report for International Application No. PCT/US98/10375.
International search report for International Application No. PCT/US98/10376.
International search report for International Application No. PCT/US98/26078.
International search report for International Application No. PCT/US98/26079.
International search report for International Application No. PCT/US98/26080.
International search report for International Application No. PCT/US98/26081.
International search report for International Application No. PCT/US98/26082.

International search report for International Application No. PCT/US98/24265.

International search report for International Application No. PCT/US00/00648.

International search report for International Application No. PCT/US00/00768.

International search report for International Application No. PCT/US02/12064.

International search report for International Application No. PCT/US02/12066.

International search report for International Application No. PCT/US/26081.

Caplus 86:72448, Abstract JP 57053785, Pyridine derivatives, Maeda Ryozo et al., Nov. 15, 1982.

Caplus 84:180049, Abstract JP 56029871, Hamada Yoshinori et al., Jul. 10, 1981.

Caplus 84:43857, Abstract JP 58021626, Maeda Ryozo et al., May 2, 1983.

Caplus 95:61995, Abstract JP 55162772, Substituted acetic derivatives, Shionogi & Co., May 23, 1980.

Abstract of EP 202,538.

Abstract of DE 3305866 (EP equivalent 116,932).

Abstract of EP 116,932.

Abstract of EP 16,371.

Abstract of EP 4931A equivalent 4,240,820).

Abstract of EP 676,395 (U.S. equivalent 5,698,581).

Abstract WO 9822103, Hedge May 28, 1998.

Chemical Abstract, vol. 116, No. 21, May 25, 1992, pp. 741-742.

Tarzia, G. et al., Whythesis and anti-inflammatory properties of some pyrrolo(1H,3H) [3,4]pyrimidin-2-ones and pyrrolo(1H,3H)[3,4-d]pyurimidin-2-ones and pyrrolo(1H,3H)-pyrimidin-2-ones. Chemical Abstracts. Aug. 27, 1979, No. 74558p; p. 594.

White, A. D., et al., "Heterocyclic Ureas: Inhibitors of Acyl-CoA:Cholesterol O-Acyltransferase as Hypochelesterolemic Agents," Jun. 6, 1996, pp. 4382-4395.

Audia, James E., et al., "Potent, Selective Tetraphdro-β-carboline Antagonists of the Serotonin 2B (5HT$_{2B}$) Contractile Receptor in the Rat Stomach Fundus," Jan. 22, 1996, pp. 2773-2780.

Forbes, Ian T., "N-(1-Methyl-5-indolyl)-N'-(3-methyl-5-isothiazolyl)urea: A Novel, High-Affinity 5-HT$_{2B}$ Receptor Antagonist," Mar. 17, 1995, pp. 855-857.

Boulton, A. J., et al., "Heterocyclic Rearrangements. Part X.[1] A Generalised Monocyclic Rearrangement," 1967, 2005-07.

W. Kolch, et al., "Raf-1 protein kinase is required for growth of induced NIH/3T3 cells," Letters to Nature, vol. 349, Jan. 31, 1991, p. 226-28.

M. Fridman, et al., "The Minimal Fragments of c-RAF-1 and NF1 That Can Suppress v-Ha-Ras-Induced Malignant Phenotype," The Journal of Biological Chemistry, vol. 269, No. 48, Dec. 2, 1994, pp. 30105-30108.

G. L. Bolton, et al., Chapter 17. Ras Oncogene Directed Approaches in Cancer Chemotherapy, Annual Reports in Medicinal Chemistry, vol. 29, 1994, pp. 165-174.

J. L. Bos, "ras Oncogenes in Human Cancer: A Review," Cancer Research, vol. 49, Sep. 1, 1989, pp. 4682-4689.

Michaelis, Justus, Liebigs Ann. Chem. (JLACBF) 397, 1913, 143.

B. P. Monia, et al., "Antitumor activity of a phosphorothioate antisense oligodeopxynucleotide targeted against C-raf kinase," Nature Medicine, vol. 2, No. 6, Jun. 1996, pp. 668-675.

Lee, et al., Bicyclic Imidazoles as a Novel Class of Cytokine Biosynthesis Inhiibitors, N.Y. Academy of Science, 1993, pp. 149-170.

F. Lepage, et al., "New N-aryl isoxazolecarboxamides and N-isoxazolybenzamides as anticonvulsant agents," Eur. J. Med. Chem, vol. 27, 1992, pp. 581-593.

Ridley, et al., "Actions of IL-1 are Selectively Controlled by p38 Mitogen-Activated Protein Kinase," The American Association of Immunologists, 1997, p. 3165-73.

N. S. Magnuson, et al., "The Raf-1 serine/threonine protein kinase," Cancer Biology, vol. 5, 1994, pp. 247-253.

G. Daum, et al., The ins and outs of Raf Kinases,: TIBS 19, Nov. 1994, pp. 474-480.

Grant, A.M. et al.: "Hypotensive thiadiazoles" J. Med. Chem. (1972), 15(10), 1082-4.

Russo, F. et al. "Synthesis of 2,6-substituted derivatives of 5H-1,3,4-thiadiazolo'3,2-a!-s triazine-5,7-dione" Farmaco, Ed.Sci. (1978), 33(12), 972-83.

Joseph T. Bruder and Imre Kovesdi, Adenovirus Infection Stimulates the Raf/MAPK Signaling Pathway and Induces Interleukin-8 Expression, May 17, 1996, pp. 198-404.

Foussard-Blanpin, Odette: "Comparative pharmacodynamic study of variously substituted carboxamides of the central nervous ststem" Ann. Pharm. Fr. (1982), 40 (4), 339-50.

Kubo, Hiroshi et al. "Herbicidal activity of 1,3,4-thiadiazole derivatives" J. Agr. Food Chem. (1970), 18(1), 60-5.

Avruch et al., "Raf meets Ras: completing the framework of a signal transduction pathway", TIBS 19; Jul. 1994; pp. 279-2823.

* cited by examiner

INHIBITION OF RAF KINASE USING QUINOLYL, ISOQUINOLYL OR PYRIDYL UREAS

This application is a continuation of U.S. non-provisional application No. 10/125,369, filed Apr. 19, 2002 now abandoned, which claims the benefit of U.S. provisional application No. 60/367,376 filed Apr. 20, 2001. The contents of U.S. non-provisional application No. 10/125,369 filed Apr. 19, 2002 and U.S. provisional application No. 60/367,376, filed Apr. 20, 2001 are incorporated by reference herein.

FIELD OF THE INVENTION

This invention relates to the use of a group of aryl ureas in treating raf mediated diseases, and pharmaceutical compositions for use in such therapy.

BACKGROUND OF THE INVENTION

The p21$^{ras}$ oncogene is a major contributor to the development and progression of human solid cancers and is mutated in 30% of all human cancers (Bolton et al. *Ann. Rep. Med. Chem.* 1994, 29, 165-74; Bos. *Cancer Res.* 1989, 49, 4682-9). In its normal, unmutated form, the ras protein is a key element of the signal transduction cascade directed by growth factor receptors in almost all tissues (Avruch et al. *Trends Biochem. Sci.* 1994, 19, 279-83). Biochemically, ras is a guanine nucleotide binding protein, and cycling between a GTP-bound activated and a GDP-bound resting form is strictly controlled by ras' endogenous GTPase activity and other regulatory proteins. In the ras mutants in cancer cells, the endogenous GTPase activity is alleviated and, therefore, the protein delivers constitutive growth signals to downstream effectors such as the enzyme raf kinase. This leads to the cancerous growth of the cells which carry these mutants (Magnuson et al. *Semin. Cancer Biol.* 1994, 5, 247-53). It has been shown that inhibiting the effect of active ras by inhibiting the raf kinase signaling pathway by administration of deactivating antibodies to raf kinase or by co-expression of dominant negative raf kinase or dominant negative MEK, the substrate of raf kinase, leads to the reversion of transformed cells to the normal growth phenotype (see: Daum et al. *Trends Biochem. Sci.* 1994, 19, 474-80; Fridman et al. *J. Biol. Chem.* 1994, 269, 30105-8. Kolch et al. (*Nature* 1991, 349, 426-28) have further indicated that inhibition of raf expression by antisense RNA blocks cell proliferation in membrane-associated oncogenes. Similarly, inhibition of raf kinase (by antisense oligodeoxynucleotides) has been correlated in vitro and in vivo with inhibition of the growth of a variety of human tumor types (Monia et al., *Nat. Med.* 1996, 2, 668-75).

SUMMARY OF THE INVENTION

The present invention provides compounds which are inhibitors of the enzyme raf kinase. Since the enzyme is a downstream effector of p21$^{ras}$, the instant inhibitors are useful in pharmaceutical compositions for human or veterinary use where inhibition of the raf kinase pathway is indicated, e.g., in the treatment of tumors and/or cancerous cell growth mediated by raf kinase. In particular, the compounds are useful in the treatment of human or animal, e.g., murine cancer, since the progression of these cancers is dependent upon the ras protein signal transduction cascade and therefore susceptible to treatment by interruption of the cascade, i.e., by inhibiting raf kinase. Accordingly, the compounds of the invention are useful in treating solid cancers, such as, for example, carcinomas (e.g., of the lungs, pancreas, thyroid, bladder or colon, myeloid disorders (e.g., myeloid leukemia) or adenomas (e.g., villous colon adenoma).

The present invention, therefore, provides compounds generally described as aryl ureas, including both aryl and heteroaryl analogues, which inhibit the raf pathway. The invention also provides a method for treating a raf mediated disease state in humans or mammals. Thus, the invention is directed to compounds which inhibit the enzyme RAF kinase and also to compounds, compositions and methods for the treatment of cancerous cell growth mediated by raf kinase wherein a compound of one of the formulae I, II or III, or a pharmaceutically acceptable salt thereof, is administered.

A-D-B (I)

A'-D-B' (II)

A"-D-B" (III)

In formulae I-III,
D is —NH—C(O)—NH—,
A is selected from the group consisting of substituted or unsubstituted t-butylpyridyl groups, (trifluoromethyl) pyridyl groups, isopropylpyridyl groups, (2-methyl-2-butyl) pyridyl groups, (3-methyl-3-pentyl) pyridyl groups and (3-ethyl-3-pentyl)pyridyl groups,
A' is a substituted isoquinolinyl group or unsubstituted isoquinolinyl group or an unsubstituted quinolinyl group,
A" is a substituted quinolinyl group,
B and B' are each, independently, a substituted or unsubstituted bridged cyclic structure of up to 30 carbon atoms of the formula -L-(ML$^1$)$_q$ wherein L comprises a cyclic moiety having at least 5 members and is bound directly to D, L$^1$ comprises a cyclic moiety having at least 5 members, M is a bridging group having at least one atom, q is an integer of from 1-3, and each cyclic structure of L and L$^1$ contains 0-4 members of the group consisting of nitrogen, oxygen and sulfur,
subject to the provisos that B is not

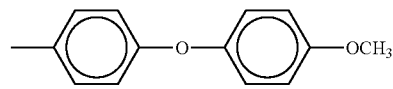

and B' is not

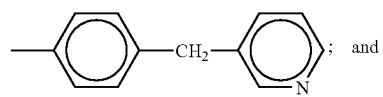

B" is a substituted or unsubstituted, up to tricyclic aryl or heteroaryl moiety of up to 30 carbon atoms with a cyclic structure bound directly to D containing at least 5 members with 0-4 members of the group consisting of nitrogen, oxygen and sulfur.

The moiety B" is preferably either a substituted or unsubstituted bridged cyclic structure of up to 30 carbon atoms of the formula -L-(ML$^1$)$_q$, a substituted or unsubstituted 6 member cyclic aryl moiety or 5 membered hetaryl moiety or a substituted or unsubstituted fused aryl ring or hetaryl ring of from 2-3 fused rings. For Example, B" can be phenyl, substituted phenyl, napthyl substituted napthyl, pyridinyl, substituted pyridinyl, pyrimidinyl, substituted pyrimidinyl, quinolinyl, substituted quinolinyl, isoquinolinyl, substituted isoquinolinyl or of the formula -L-$(ML^1)_q$.

The substituents for A" and the substituted isoquinolinyl groups of A' are selected from the group consisting of halogen, up to per-halo, and Wn, where n is 0-3 and each W is independently selected from the group consisting of $C_{1-10}$ alkyl, $C_{1-10}$ alkoxy, at least a five membered $C_{3-10}$ cycloalkyl having 0-3 heteroatoms, $C_{2-10}$ alkenyl, $C_{1-10}$ alkenoyl, substituted $C_{1-10}$ alkyl, substituted $C_{1-10}$ alkoxy, a substituted $C_{3-10}$ cycloalkyl having at least 5 cyclic members and 0-3 heteroatoms selected from N, S and O; $C_6$-$C_{14}$ aryl, $C_7$-$C_{24}$ alkaryl, $C_7$-$C_{24}$ aralkyl, $C_3$-$C_{12}$ heteroaryl having 1-3 heteroatoms selected from O, N and S, $C_4$-$C_{23}$ alkheteroaryl having 1-3 heteroatoms selected from O, N and S, up to per halo substituted $C_6$-$C_{12}$ aryl, up to per halo substituted $C_3$-$C_{12}$ hetaryl having at least 5 members and 1-3 heteroatoms selected from O, N and S, up to per halo substituted $C_7$-$C_{24}$ aralkyl, up to per halo substituted $C_7$-$C_{24}$ alkaryl, up to per halo substituted $C_4$-$C_{23}$ alkheteroaryl having at least 5 cyclic members and 1-3 heteroatoms selected from O, N and S, —CN, —$CO_2R^7$, —$C(O)NR^7R^{7'}$, —C(O)—$R^7$, —$NO_2$, —$OR^7$, —$SR^7$, —$NR^7R^{7'}$, —$NR^7C(O)OR^{7'}$, —$NR^7C(O)R^{7'}$, with each $R^7$ and $R^{7'}$ independently selected from hydrogen, $C_{1-10}$ alkyl, $C_{1-10}$ alkoxy, $C_{2-10}$ alkenyl, $C_{1-10}$ alkenoyl, up to per halosubstituted $C_{1-10}$ alkyl, up to per halosubstituted $C_{1-10}$ alkoxy, up to per halosubstituted $C_{2-10}$ alkenyl and up to per halosubstituted $C_{1-10}$ alkenoyl.

The substituents for the substituted t-butylpyridyl, (trifluoromethyl) pyridyl, isopropylpyridyl, (2-methyl-2-butyl) pyridyl, (3-methyl-3-pentyl) pyridyl groups and (3-ethyl-3-penty)pyridyl groups, of A are selected from the group consisting of halogen, up to per-halo, and Zn, where n is 0-3 and each Z is independently selected from the group consisting of $C_{1-10}$ alkyl, $C_{1-10}$ alkoxy, $C_{2-10}$ alkenyl, $C_{1-10}$ alkenoyl, —CN, —$CO_2R^7$, —$C(O)NR^7R^{7'}$, —C(O)—$R^7$, —$NO_2$, —$OR^7$, —$SR^7$, —$NR^7R^{7'}$, —$NR^7C(O)OR^{7'}$, —$NR^7C(O)R^{7'}$, with each $R^7$ and $R^{7'}$ independently as defined above.

Where B, B' and B" are substituted, the substituents are selected from the group consisting of halogen, up to per-halo, and Jn, where n is 0-3 and each J is independently selected from the group consisting of —CN, —$CO_2R^7$, —$C(O)NR^7R^{7'}$, —C(O)—$R^7$, —$NO_2$, —OR, —$SR^7$, —$NR^7R^{7'}$, —$NR^7C(O)OR^{7'}$, —$NR^7C(O)R^{7'}$, $C_{1-10}$ alkyl, $C_{1-10}$ alkoxy, $C_{3-10}$ cycloalkyl having at least five cyclic members and 0-3 heteroatoms, $C_{2-10}$ alkenyl, $C_{1-10}$ alkenoyl, $C_{6-12}$ aryl, $C_{3-12}$ hetaryl having at least five cyclic members and 1-3 heteroatoms selected from N, S and O, $C_{7-24}$ aralkyl, $C_{7-24}$ alkaryl, substituted $C_{1-10}$ alkyl, substituted $C_{1-10}$ alkoxy, substituted $C_{3-10}$ cycloalkyl having at least five cyclic members and 0-3 heteroatoms selected from N, S and O, substituted $C_6$-$C_{14}$ aryl, substituted $C_{3-12}$ hetaryl having at least five cyclic members and 1-3 heteroatoms selected from N, S and O, substituted $C_{7-24}$ alkaryl, substituted $C_7$-$C_{24}$ aralkyl and -Q-Ar, subject to the proviso that where B, B' or B" is -L$(ML^1)_q$, $L^1$ is not substituted by the substituents —$C(O)R^a$, —$C(NR^a)R^b$, —$C(O)NR^aR^b$ and —$SO_2R^a$ wherein $R^a$ and $R^b$ are each, independently, hydrogen or a carbon based moiety of up to 24 carbon atoms, optionally containing heteroatoms selected from N, S and 0.

$R^a$ and $R^b$ are preferably $C_{1-10}$ alkyl, $C_{1-10}$ alkoxy, $C_{3-10}$ cycloalkyl having 0-3 heteroatoms, $C_{2-10}$ alkenyl, $C_{1-10}$ alkenoyl, $C_{6-12}$ aryl, $C_{3-12}$ hetaryl having 1-3 heteroatoms selected from N, S and O, $C_{7-24}$ aralkyl, $C_{7-24}$ alkaryl, substituted $C_{1-10}$ alkyl, substituted $C_{1-10}$ alkoxy, substituted $C_{3-10}$ cycloalkyl having 0-3 heteroatoms selected from N, S and O, substituted $C_6$-$C_{14}$ aryl, substituted $C_{3-12}$ hetaryl having 1-3 heteroatoms selected from N, S and O, substituted $C_{7-24}$ alkaryl or substituted $C_7$-$C_{24}$ aralkyl, where $R^a$ is a substituted group, it is substituted by halogen up to per halo.

Where B" of Formula III is a substituted pyridyl, substituted quinolinyl or isoquinolinyl group, B" is preferably substituted 1 to 3 times by 1 or more substituents selected from the group consisting of —CN, halogen, $C_1$-$C_{10}$ alkyl, $C_1$-$C_{10}$ alkoxy, —OH, up to per halo substituted $C_1$-$C_{10}$ alkyl, up to per halo substituted $C_1$-$C_{10}$ alkoxy or phenyl substituted by halogen up to per halo.

Where J is a substituted group, it is substituted by halogen, up to per halo, or by one or more substituents independently selected from the group consisting of —CN, —$CO_2R^7$, —$OR^7$, —$SR^7$, —$NR^7R^{7'}$, —$NO_2$, —$NR^7C(O)R^{7'}$, —$NR^7C(O)OR^{7'}$; with each $R^7$ and $R^{7'}$ independently as defined above.

Where the substituents for B, B' and B" are -Q-Ar, Q is —O—, —S—, —$N(R^7)$—, —$(CH_2)_m$—, —C(O)—, —O—$[C(R^9)(R^{9'})]_m$—, —CH(OH)—, —$(CH_2)_mO$—, —$(CH_2)_mS$—, —$(CH_2)_mN(R^7)$—, —$O(CH_2)_m$—, —$CHX^a$—, —$CX^a_2$—, —S—$(CH_2)_m$— and —$N(R^7)(CH_2)_m$—, where m=1-3, $R^9$ and $R^{9'}$ are each, independently, hydrogen, $C_1$-$C_4$ alkyl and halogen, and $X^a$ is halogen and each $R^7$ is as defined above, and Ar is a 5- or 6-member aromatic structure. This aromatic structure of Ar
  a) contains 0-2 members selected from the group consisting of nitrogen, oxygen and sulfur,
  b) is free of the substituents —$C(O)R^a$, —$C(NR^a)R^b$, —$C(O)NR^aR^b$, and $SO_2R^a$, wherein $R^a$ and $R^b$ are as defined above;
  c) is optionally substituted by halogen, up to per-halo, and
  d) is optionally substituted by Mp, wherein p is 0 to 3 and each M is independently selected from the group consisting of —CN, —$NO_2$, —$OR^7$, —$SR^7$, —$NR^7R^7$, —$NR^7C(O)OR^{7'}$, —$NR^7C(O)R^7$, with each $R^7$ and $R^{7'}$ independently as defined above, $C_{1-10}$ alkyl, $C_{1-10}$ alkoxy, $C_{2-10}$ alkenyl and $C_{1-10}$ alkenoyl halo substituted $C_{1-10}$ alkyl up to per halo, halo substituted $C_{1-10}$ alkoxy up to per halo, halosubstituted $C_{2-10}$ alkenyl up to per halo and halosubstituted $C_{1-10}$ alkenoyl up to per halo.

The bridging group M in the formula -L-$(ML^1)_q$, for B, B' and B" is preferably selected from the group consisting of —O—, —S—, —$N(R^7)$—, —$(CH_2)_m$—, —C(O)—, —CH(OH)—, —$(CH_2)_mO$—, —$(CH_2)_mS$—, —$(CH_2)_m N(R^7)$—, —$O(CH_2)_m$— $CHX^a$—, —$CX^a_2$—, —S—$(CH_2)_m$— and —$N(R^7)(CH_2)_m$—, where m=1-3, $X^a$ is hydrogen and $R^7$ is as defined above and q is 1. More preferably, M is —O—, —$CH_2$—, —S—, —NH—, —C(O)—, —O—$CH_2$— and —$CH_2$—O—.

The moieties L and $L^1$ in the formula -L-$(ML^1)_q$ for B, B' and B" are typically each, independently, a substituted aryl moiety having at least 6 cyclic members, a substituted hetaryl moiety having at least 5 cyclic members, an unsubstituted aryl moiety having at least 6 cyclic members or an unsubstituted hetaryl moiety having at least 5 cyclic members. The hetaryl moieties for L and L' typically have 1 to 4 members selected from the group of hetaryl atoms consisting of nitrogen, oxygen and sulfur with the balance of the hetaryl moiety being carbon. More typical moieties for $L^1$ and L are selected from the group consisting of thiophene, phenyl, substituted phenyl, pyridinyl, substituted pyridinyl, pyrimidinyl substituted pyrimidinyl, quinolyl, substituted quinolyl isoquinolyl, substituted isoquinolyl, napthyl and substituted napthyl.

The substituted t-butylpyridyls, (trifluoromethyl) pyridyls, isopropylpyridyls, (2-methyl-2-butyl) pyridyls, (3-methyl-3-pentyl) pyridyls and (3-ethyl-3-pentyl) pyridyls of A, the substituted isoquinolinyls of A' and the substituted quinolinyls of A" preferably have 1-3 substituents selected from the group consisting of $C_{1-10}$ alkyl, up to per halo substituted $C_{1-10}$ alkyl, —CN, —OH, halogen, $C_{1-10}$ alkoxy, up to per halo substituted $C_{1-10}$ alkoxy and C3-C10 heterocyclic moieties comprising 1 to 2 heteroatoms selected from the group of consisting of nitrogen, oxygen and sulfur.

Preferred compounds of Formula I include those wherein the cyclic structures of B and L bound directly to D are not substituted in the ortho position by —OH.

In Formulae I, II and III suitable hetaryl groups include, but are not limited to, 5-12 carbon-atom aromatic rings or ring systems containing 1-3 rings, at least one of which is aromatic, in which one or more, e.g., 1-4 carbon atoms in one or more of the rings can be replaced by oxygen, nitrogen or sulfur atoms. Each ring typically has 3-7 atoms. For example, B can be 2- or 3-furyl, 2- or 3-thienyl, 2- or 4-triazinyl, 1-, 2- or 3-pyrrolyl, 1-, 2-, 4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, 1,2,3-triazol-1-, -4- or -5-yl, 1,2,4-triazol-1-, -3- or -5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-oxadiazol-3- or -5-yl, 1,3,4-thiadiazol-2- or -5-yl, 1,3,4-thiadiazol-3- or -5-yl, 1,2,3-thiadiazol-4- or -5-yl, 2-, 3-, 4-, 5- or 6-2H-thiopyranyl, 2-, 3- or 4-4H-thiopyranyl, 3- or 4-pyridazinyl, pyrazinyl, 2-, 3-, 4-, 5-, 6- or 7-benzofuryl, 2-, 3-, 4-, 5-, 6- or 7-benzothienyl, 1-, 2-, 3-, 4-, 5-, 6- or 7-indolyl, 1-, 2-, 4- or 5-benzimidazolyl, 1-, 3-, 4-, 5-, 6- or 7-benzopyrazolyl, 2-, 4-, 5-, 6- or 7-benzoxazolyl, 3-, 4-, 5-6- or 7-benzisoxazolyl, 1-, 3-, 4-, 5-, 6- or 7-benzothiazolyl, 2-, 4-, 5-, 6- or 7-benzisothiazolyl, 2-, 4-, 5-, 6- or 7-benz-1,3-oxadiazolyl, 2-, 3-, 4-, 5-, 6-, 7- or 8-quinolinyl, 1-, 3-, 4-, 5-, 6-, 7-, 8-isoquinolinyl, 1-, 2-, 3-, 4- or 9-carbazolyl, 1-, 2-, 3-, 4-, 5-, 6-, 7-, 8- or 9-acridinyl, or 2-, 4-, 5-, 6-, 7- or 8-quinazolinyl, or additionally optionally substituted phenyl, 2- or 3-thienyl, 1,3,4-thiadiazolyl, 3-pyrryl, 3-pyrazolyl, 2-thiazolyl or 5-thiazolyl, etc. For example, B can be 4-methylphenyl, 5-methyl-2-thienyl, 4-methyl-2-thienyl, 1-methyl-3-pyrryl, 1-methyl-3-pyrazolyl, 5-methyl-2-thiazolyl or 5-methyl-1,2,4-thiadiazol-2-yl.

Suitable alkyl groups and alkyl portions of groups, e.g., alkoxy, etc. throughout include methyl, ethyl, propyl, butyl, etc., including all straight-chain and branched isomers such as isopropyl, isobutyl, sec-butyl, tert-butyl, etc.

Suitable aryl groups which do not contain heteroatoms include, for example, phenyl and 1- and 2-naphthyl.

The term "cycloalkyl", as used herein, refers to cyclic structures with or without alkyl substituents such that, for example, "$C_4$ cycloalkyl" includes methyl substituted cyclopropyl groups as well as cyclobutyl groups. The term "cycloalkyl", as used herein also includes saturated heterocyclic groups.

Suitable halogen groups include F, Cl, Br, and/or I, from one to per-substitution (i.e. all H atoms on a group replaced by a halogen atom) being possible where an alkyl group is substituted by halogen, mixed substitution of halogen atom types also being possible on a given moiety.

The invention also relates to compounds per se, of formula I, II and III.

The present invention is also directed to pharmaceutically acceptable salts of formulae I, II and III. Suitable pharmaceutically acceptable salts are well known to those skilled in the art and include basic salts of inorganic and organic acids, such as hydrochloric acid, hydrobromic acid, sulphuric acid, phosphoric acid, methanesulphonic acid, trifluoromethanesulfonic acid, benzenesulphonic acid, p-toluenesulfonic acid, 1-naphthalenesulfonic acid, 2-naphthalenesulfonic acid, acetic acid, trifluoroacetic acid, malic acid, tartaric acid, citric acid, lactic acid, oxalic acid, succinic acid, fumaric acid, maleic acid, benzoic acid, salicylic acid, phenylacetic acid, and mandelic acid. In addition, pharmaceutically acceptable salts include acid salts of inorganic bases, such as salts containing alkaline cations (e.g., $Li^+$ Na+ or $K^+$), alkaline earth cations (e.g., $Mg^{+2}$, $Ca^{+2}$ or $Ba^{+2}$), the ammonium cation, as well as acid salts of organic bases, including aliphatic and aromatic substituted ammonium, and quaternary ammonium cations, such as those arising from protonation or peralkylation of triethylamine, N,N-diethylamine, N,N-dicyclohexylamine, lysine, pyridine, N,N-dimethylaminopyridine (DMAP), 1,4-diazabiclo[2.2.2]octane (DABCO), 1,5-diazabicyclo[4.3.0]non-5-ene (DBN) and 1,8-diazabicyclo[5.4.0]undec-7-ene (DBU).

A number of the compounds of Formula I, II and III possess asymmetric carbons and can therefore exist in racemic and optically active forms. Methods of separation of enantiomeric and diastereomeric mixtures are well known to one skilled in the art. The present invention encompasses any racemic or optically active form of compounds described in Formulae I, II and III which possess progesterone receptor binding activity.

General Preparative Methods

The compounds of Formulae I, II and III may be prepared by the use of known chemical reactions and procedures, some from starting materials which are commercially available. Nevertheless, general preparative methods are provided below to aid one skilled in the art in synthesizing these compounds, with more detailed examples being provided in the Experimental section which follows.

Substituted and unsubstituted aminoquinolines, aminoisoquinolines and aminopyridines may be prepared using standard methods (see, for example: A. R. Katritzky et al. (Eds.). *Comprehensive Heterocyclic Chemistry II*, Vol. 5. M. H. Palmer. *Heterocyclic Compounds*; Arnold Ltd., London (1967). C. K. Esser et al. WO 96/18616. C. J. Donahue et al. *Inorg. Chem.* 30, 1991, 1588. E. Cho et al. WO 98/00402. A. Cordi et al. *Bioorg. Med. Chem.* 3, 1995, 129). In addition, many aminoquinolines, aminoisoquinolines and aminopyridines are commercially available.

Substituted anilines may be generated using standard methods (March. *Advanced Organic Chemistry*, 3$^{rd}$ Ed.; John Wiley: New York (1985). Larock. *Comprehensive Organic Transformations*; VCH Publishers: New York (1989)). As shown in Scheme I, aryl amines are commonly synthesized by reduction of nitroaryls using a metal catalyst, such as Ni, Pd, or Pt, and $H_2$ or a hydride transfer agent, such as formate, cyclohexadiene, or a borohydride (Rylander. *Hydrogenation Methods*; Academic Press: London, UK (1985)). Nitroaryls may also be directly reduced using a strong hydride source, such as $LiAlH_4$ (Seyden-Penne. *Reductions by the Alumino- and Borohydrides in Organic Synthesis*; VCH Publishers: New York (1991)), or using a zero valent metal, such as Fe, Sn or Ca, often in acidic media. Many methods exist for the synthesis of nitroaryls (March. *Advanced Organic Chemistry*, 3$^{rd}$ Ed.; John Wiley:

New York (1985). Larock. *Comprehensive Organic Transformations*; VCH Publishers: New York (1989)).

Scheme I Reduction of Nitroaryls to Aryl Amines

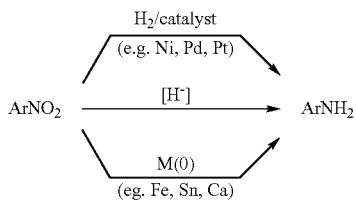

Nitroaryls are commonly formed by electrophilic aromatic nitration using $HNO_3$, or an alternative $NO_2^+$ source. Nitroaryls may be further elaborated prior to reduction. Thus, nitroaryls substituted with

potential leaving groups (eg. F, Cl, Br, etc.) may undergo substitution reactions on treatment with nucleophiles, such as thiolate (exemplified in Scheme II) or phenoxide. Nitroaryls may also undergo Ullman-type coupling reactions (Scheme II).

Scheme II Selected Nucleophilic Aromatic Substitution using Nitroaryls

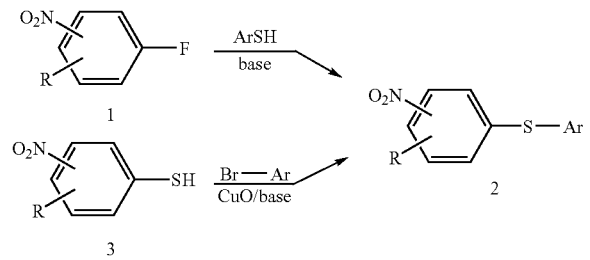

Nitroaryls may also undergo transition metal mediated cross coupling reactions. For example, nitroaryl electrophiles, such as nitroaryl bromides, iodides or triflates, undergo palladium mediated cross coupling reactions with aryl nucleophiles, such as arylboronic acids (Suzuki reactions, exemplified below), aryltins (Stille reactions) or arylzincs (Negishi reaction) to afford the biaryl (5).

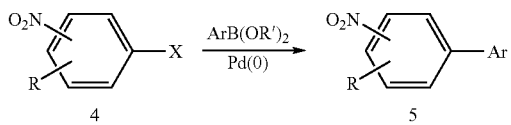

Either nitroaryls or anilines may be converted into the corresponding arenesulfonyl chloride (7) on treatment with chlorosulfonic acid. Reaction of the sulfonyl chloride with a fluoride source, such as KF then affords sulfonyl fluoride (8). Reaction of sulfonyl fluoride 8 with trimethylsilyl trifluoromethane in the presence of a fluoride source, such as tris(dimethylamino)sulfonium difluorotrimethylsiliconate (TASF) leads to the corresponding trifluoromethylsulfone (9). Alternatively, sulfonyl chloride 7 may be reduced to the arenethiol (10), for example with zinc amalgum. Reaction of thiol 10 with $CHClF_2$ in the presence of base gives the difluoromethyl mercaptan (11), which may be oxidized to the sulfone (12) with any of a variety of oxidants, including $CrO_3$-acetic anhydride (Sedova et al. *Zh. Org. Khim.* 1970, 6, (568).

Scheme III Selected Methods of Fluorinated Aryl Sulfone Synthesis

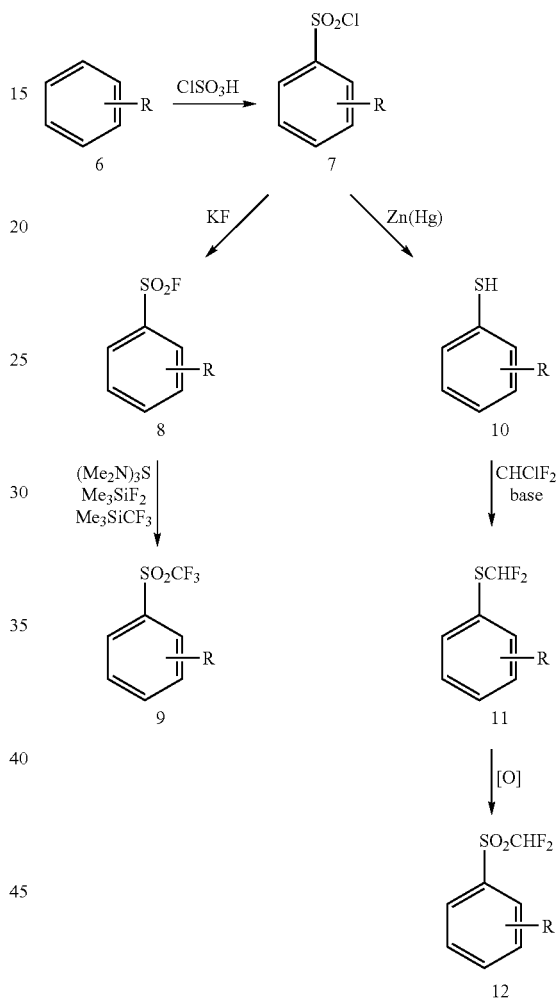

As shown in Scheme IV, non-symmetrical urea formation may involve reaction of an aryl isocyanate (14) with an aryl amine (13). The heteroaryl isocyanate may be synthesized from a heteroaryl amine by treatment with phosgene or a phosgene equivalent, such as trichloromethyl chloroformate (diphosgene), bis(trichloromethyl) carbonate (triphosgene), or N,N'-carbonyldiimidazole (CDI). The isocyanate may also be derived from a heterocyclic carboxylic acid derivative, such as an ester, an acid halide or an anhydride by a Curtius-type rearrangement. Thus, reaction of acid derivative 16 with an azide source, followed by rearrangement affords the isocyanate. The corresponding carboxylic acid (17) may also be subjected to Curtius-type rearrangements using diphenylphosphoryl azide (DPPA) or a similar reagent.

Scheme IV Selected Methods of Non-Symmetrical Urea Formation

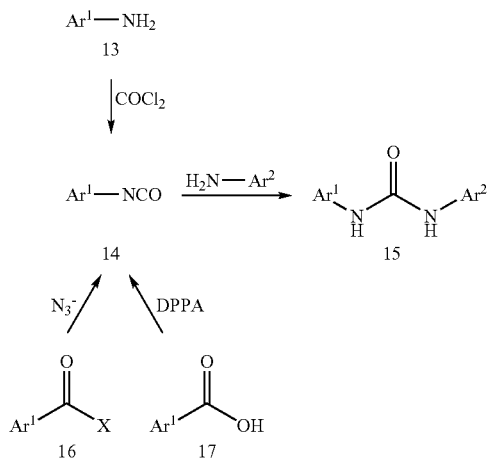

Finally, ureas may be further manipulated using methods familiar to those skilled in the art.

The invention also includes pharmaceutical compositions including at least one compound of Formula I, II or III and a physiologically acceptable carrier.

The compounds may be administered orally, dermally, parenterally, by injection, by inhalation or spray, or sublingually, rectally or vaginally in dosage unit formulations. The term 'administration by injection' includes intravenous, intraarticular, intramuscular, subcutaneous and parenteral injections, as well as use of infusion techniques. Dermal administration may include topical application or transdermal administration. One or more compounds may be present in association with one or more non-toxic pharmaceutically acceptable carriers and if desired other active ingredients.

Compositions intended for oral use may be prepared according to any suitable method known to the art for the manufacture of pharmaceutical compositions. Such compositions may contain one or more agents selected from the group consisting of diluents, sweetening agents, flavoring agents, coloring agents and preserving agents in order to provide palatable preparations. Tablets contain the active ingredient in admixture with non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; and binding agents, for example magnesium stearate, stearic acid or talc. The tablets may be uncoated or they may be coated by known techniques to delay disintegration and adsorption in the gastrointestinal tract and thereby provide a sustained action over a longer period. For example, a time delay material such as glyceryl monostearate or glyceryl distearate may be employed. These compounds may also be prepared in solid, rapidly released form.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions containing the active materials in admixture with excipients suitable for the manufacture of aqueous suspensions may also be used. Such excipients are suspending agents, for example sodium carboxymethylcellulose, methylcellulose, hydroxypropyl-methylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example, sweetening, flavoring and coloring agents, may also be present.

The compounds may also be in the form of non-aqueous liquid formulations, e.g., oily suspensions which may be formulated by suspending the active ingredients in a vegetable oil, for example arachis oil, olive oil, sesame oil or peanut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Pharmaceutical compositions of the invention may also be in the form of oil-in-water emulsions. The oil phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The compounds may also be administered in the form of suppositories for rectal or vaginal administration of the drug. These compositions can be prepared by mixing the drug with a suitable non-irritating excipient which is solid at ordinary temperatures but liquid at the rectal or vaginal temperature and will therefore melt in the rectum or vagina to release the drug. Such materials include cocoa butter and polyethylene glycols.

Compounds of the invention may also be administered transdermally using methods known to those skilled in the art (see, for example: Chien; "Transdermal Controlled Systemic Medications"; Marcel Dekker, Inc.; 1987. Lipp et al. WO94/04157 3 Mar. 1994). For example, a solution or suspension of a compound of Formula I in a suitable volatile solvent optionally containing penetration enhancing agents can be combined with additional additives known to those skilled in the art, such as matrix materials and bacteriocides. After sterilization, the resulting mixture can be formulated following known procedures into dosage forms. In addition, on treatment with emulsifying agents and water, a solution or suspension of a compound of Formulae I, II or III may be formulated into a lotion or salve.

Suitable solvents for processing transdermal delivery systems are known to those skilled in the art, and include lower alcohols such as ethanol or isopropyl alcohol, lower ketones such as acetone, lower carboxylic acid esters such as ethyl acetate, polar ethers such as tetrahydrofuran, lower hydrocarbons such as hexane, cyclohexane or benzene, or halogenated hydrocarbons such as dichloromethane, chloroform, trichlorotrifluoroethane, or trichlorofluoroethane. Suitable solvents may also include mixtures one or more materials selected from lower alcohols, lower ketones, lower carboxylic acid esters, polar ethers, lower hydrocarbons, halogenated hydrocarbons.

Suitable penetration enhancing materials for transdermal delivery systems are known to those skilled in the art, and include, for example, monohydroxy or polyhydroxy alcohols such as ethanol, propylene glycol or benzyl alcohol, saturated or unsaturated $C_8$-$C_{18}$ fatty alcohols such as lauryl alcohol or cetyl alcohol, saturated or unsaturated $C_8$-$C_{18}$ fatty acids such as stearic acid, saturated or unsaturated fatty esters with up to 24 carbons such as methyl, ethyl, propyl, isopropyl, n-butyl, sec-butyl isobutyl tert-butyl or monoglycerin esters of acetic acid, capronic acid, lauric acid, myristinic acid, stearic acid, or palmitic acid, or diesters of saturated or unsaturated dicarboxylic acids with a total of up to 24 carbons such as diisopropyl adipate, diisobutyl adipate, diisopropyl sebacate, diisopropyl maleate, or diisopropyl fumarate. Additional penetration enhancing materials include phosphatidyl derivatives such as lecithin or cephalin, terpenes, amides, ketones, ureas and their derivatives, and ethers such as dimethyl isosorbid and diethyleneglycol monoethyl ether. Suitable penetration enhancing formulations may also include mixtures one or more materials selected from monohydroxy or polyhydroxy alcohols, saturated or unsaturated $C_8$-$C_{18}$ fatty alcohols, saturated or unsaturated $C_8$-$C_{18}$ fatty acids, saturated or unsaturated fatty esters with up to 24 carbons, diesters of saturated or unsaturated dicarboxylic acids with a total of up to 24 carbons, phosphatidyl derivatives, terpenes, amides, ketones, ureas and their derivatives, and ethers.

Suitable binding materials for transdermal delivery systems are known to those skilled in the art and include polyacrylates, silicones, polyurethanes, block polymers, styrene-butadiene copolymers, and natural and synthetic rubbers. Cellulose ethers, derivatized polyethylenes, and silicates may also be used as matrix components. Additional additives, such as viscous resins or oils may be added to increase the viscosity of the matrix.

For all regimens of use disclosed herein for compounds of Formulae I, II and III, the daily oral dosage regimen will preferably be from 0.01 to 200 mg/Kg of total body weight. The daily dosage for administration by injection, including intravenous, intramuscular, subcutaneous and parenteral injections, and use of infusion techniques will preferably be from 0.01 to 200 mg/Kg of total body weight. The daily rectal dosage regimen will preferably be from 0.01 to 200 mg/Kg of total body weight. The daily vaginal dosage regimen will preferably be from 0.01 to 200 mg/Kg of total body weight. The daily dosages for oral administration, administration by injection, rectal administration and vaginal administration can be achieved by multiple administrations per day or by administration as infrequently as once every 14 days. The long term dosage, can range from 100-800 mg/Kg of total body weight, more preferably 200-600 mg/Kg of total body weight. The daily topical dosage regimen will preferably be from 0.1 to 200 mg administered between one to four times daily. The transdermal concentration will preferably be that required to maintain a daily dose of from 0.01 to 200 mg/Kg of total body weight. The daily inhalation dosage regimen will preferably be from 0.01 to 10 mg/Kg of total body weight.

It will be appreciated by those skilled in the art that the particular method of administration will depend on a variety of factors, all of which are considered routinely when administering therapeutics. It will also be understood, however, that the specific dose level for any given patient will depend upon a variety of factors, including, but not limited to the activity of the specific compound employed, the age of the patient, the body weight of the patient, the general health of the patient, the gender of the patient, the diet of the patient, time of administration, route of administration, rate of excretion, drug combinations, and the severity of the condition undergoing therapy. It will be further appreciated by one skilled in the art that the optimal course of treatment, ie., the mode of treatment and the daily or weekly number of doses of a compound of Formulae I, II or III or a pharmaceutically acceptable salt thereof given for a defined number of days, can be ascertained by those skilled in the art using conventional treatment tests.

The entire disclosure of all applications, patents and publications cited above and below are hereby incorporated by reference.

The compounds of FIG. I, II and III are producible from known compounds (or from starting materials which, in turn, are producible from known compounds), e.g., through the general preparative methods shown below. The activity of a given compound to inhibit raf kinase can be routinely assayed, e.g., according to procedures disclosed below. The following examples are for illustrative purposes only and are not intended, nor should they be construed to limit the invention in any way.

EXAMPLES

All reactions were performed in flame-dried or oven-dried glassware under a positive pressure of dry argon or dry nitrogen, and were stirred magnetically unless otherwise indicated. Sensitive liquids and solutions were transferred via syringe or cannula, and introduced into reaction vessels through rubber septa. Unless otherwise stated, the term 'concentration under reduced pressure' refers to use of a Buchi rotary evaporator at approximately 15 mmHg. Unless otherwise stated, the term 'under high vacuum' refers to a vacuum of 0.4-1.0 mmHg.

All temperatures are reported uncorrected in degrees Celsius (° C.). Unless otherwise indicated, all parts and percentages are by weight.

Commercial grade reagents and solvents were used without further purification. N-cyclohexyl-N'-(methylpolystyrene)carbodiimide was purchased from Calbiochem-Novabiochem Corp. 5-(Trifluoromethyl)-2-aminopyridine, 3-aminoqunioline, 3-aminoisoquinoline, 1-(4-methylpiperazinyl)-3-aminoisoquinoline, ethyl 4-isocyanatobenzoate, N-acetyl-4-chloro-2-methoxy-5-(trifluoromethyl)aniline, 4-(4-nitrobenzyl)pyridine, 4-phenoxyaniline, 4-(4-methylphenoxy)aniline, 4-(4-chlorophenoxy)aniline and 4-chloro-3-(trifluoromethyl)phenyl isocyanate were purchased and used without further purification. Syntheses of 2-amino-4-tert-butylpyridine (C. K. Esser et al. WO 96/18616; C. J. Donahue et al. *Inorg. Chem.* 30, 1991, 1588), 3-amino-2-methoxyquinoline (E. Cho et al. WO 98/00402; A. Cordi et al. EP 542,609; *IBID Bioorg. Med. Chem.* 3, 1995, 129), 4-(3-carbamoylphenoxy)-1-nitrobenzene (K. Ikawa *Yakugaku Zasshi* 79, 1959, 760; *Chem. Abstr.* 53, 1959, 12761b), 4-[(4-methoxyphenyl)methylamino]aniline (P. Brenneisen et al. U.S. Pat. No. 3,755,406; *IBID* U.S. Pat. No. 3,839,582; *IBID* DE 1,935,388), 4-(4-pyridylcarbonyl)aniline (M. L. Carmello et al. *Pestic. Sci.* 45, 1995, 227), 3-tert-butylphenyl isocyanate (O. Rohr et al. DE 2,436,108) and 2-methoxy-5-(trifluoromethyl)phenyl isocyanate (K. Inukai et al. JP 42,025,067; *IBID Kogyo Kagaku Zasshi* 70, 1967, 491) have previously been described.

Thin-layer chromatography (TLC) was performed using Whatman® pre-coated glass-backed silica gel 60A F-254 250 μm plates. Visualization of plates was effected by one or more of the following techniques: (a) ultraviolet illumination, (b) exposure to iodine vapor, (c) immersion of the plate in a 10% solution of phosphomolybdic acid in ethanol followed by heating, (d) immersion of the plate in a cerium sulfate solution followed by heating, and/or (e) immersion of the plate in an acidic ethanol solution of 2,4-dinitrophenylhydrazine followed by heating. Column chromatography (flash chromatography) was performed using 230-400 mesh EM Science® silica gel.

Melting points (mp) were determined using a Thomas-Hoover melting point apparatus or a Mettler FP66 automated melting point apparatus and are uncorrected. Fourier transform infrared spectra were obtained using a Mattson 4020 Galaxy Series spectrophotometer. Proton ($^1$H) nuclear magnetic resonance (NMR) spectra were measured with a General Electric GN-Omega 300 (300 MHz) spectrometer with either Me$_4$Si (δ0.00) or residual protonated solvent (CHCl$_3$ δ 7.26; MeOH δ 3.30; DMSO δ 2.49) as standard. Carbon ($^{13}$C) NMR spectra were measured with a General Electric GN-Omega 300 (75 MHz) spectrometer with solvent (CDCl$_3$ δ 77.0; MeOD-d$_3$; δ 49.0; DMSO-d$_6$ δ 39.5) as standard. Low resolution mass spectra (MS) and high resolution mass spectra (HRMS) were either obtained as electron impact (EI) mass spectra or as fast atom bombardment (FAB) mass spectra. Electron impact mass spectra (EI-MS) were obtained with a Hewlett Packard 5989A mass spectrometer equipped with a Vacumetrics Desorption Chemical Ionization Probe for sample introduction. The ion source was maintained at 250° C. Electron impact ionization was performed with electron energy of 70 eV and a trap current of 300 μA. Liquid-cesium secondary ion mass spectra (FAB-MS), an updated version of fast atom bombardment were obtained using a Kratos Concept 1-H spectrometer. Chemical ionization mass spectra (CI-MS) were obtained using a Hewlett Packard MS-Engine (5989A) with methane or ammonia as the reagent gas (1×10$^{-4}$ torr to 2.5×10$^{-4}$ torr). The direct insertion desorption chemical ionization (DCI) probe (Vaccumetrics, Inc.) was ramped from 0-1.5 amps in 10 sec and held at 10 amps until all traces of the sample disappeared (~1-2 min). Spectra were scanned from 50-800 amu at 2 sec per scan. HPLC—electrospray mass spectra (HPLC ES-MS) were obtained using a Hewlett-Packard 1100 HPLC equipped with a quaternary pump, a variable wavelength detector, a C-18 column, and a Finnigan LCQ ion trap mass spectrometer with electrospray ionization. Spectra were scanned from 120-800 amu using a variable ion time according to the number of ions in the source. Gas chromatography-ion selective mass spectra (GC-MS) were obtained with a Hewlett Packard 5890 gas chromatograph equipped with an HP-1 methyl silicone column (0.33 mM coating; 25 m×0.2 mm) and a Hewlett Packard 5971 Mass Selective Detector (ionization energy 70 eV). Elemental analyses were conducted by Robertson Microlit Labs, Madison N.J.

All compounds displayed NMR spectra, LRMS and either elemental analysis or HRMS consistant with assigned structures.

| List of Abbreviations and Acronyms: | |
|---|---|
| AcOH | acetic acid |
| anh | anhydrous |
| atm | atmosphere(s) |
| BOC | tert-butoxycarbonyl |
| CDI | 1,1'-carbonyl diimidazole |
| conc | concentrated |
| dec | decomposition |
| DMAC | N,N-dimethylacetamide |
| DMPU | 1,3-dimethyl-3,4,5,6-tetrahydro-2(1H)-pyrimidinone |
| DMF | N,N-dimethylformamide |
| DMSO | dimethylsulfoxide |
| DPPA | diphenylphosphoryl azide |
| EDCI | 1-(3-dimethylaminopropyl)-3-ethylcarbodiimide |
| EtOAc | ethyl acetate |
| EtOH | ethanol (100%) |
| Et$_2$O | diethyl ether |
| Et$_3$N | triethylamine |
| HOBT | 1-hydroxybenzotriazole |
| m-CPBA | 3-chloroperoxybenzoic acid |
| MeOH | methanol |
| pet. ether | petroleum ether (boiling range 30-60° C.) |
| THF | tetrahydrofuran |
| TFA | trifluoroacetic acid |
| Tf | trifluoromethanesulfonyl |

A. General Methods for Synthesis of Substituted Anilines

A1. General Method for Substituted Aniline Formation Via Hydrogenation of a Nitroarene

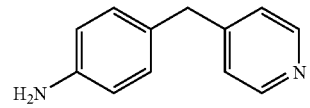

4-(4-Pyridinylmethyl)aniline: To a solution of 4-(4-nitrobenzyl)pyridine (7.0 g, 32.68 mmol) in EtOH (200 mL) was added 10% Pd/C (0.7 g) and the resulting slurry was shaken under a H$_2$ atmosphere (50 psi) using a Parr shaker. After 1 h, TLC and $^1$H-NMR of an aliquot indicated complete reaction. The mixture was filtered through a short pad of Celite®. The filtrate was concentrated in vacuo to afford a white solid (5.4 g, 90%): $^1$H-NMR (DMSO-d$_6$) δ 3.74 (s, 2H), 4.91 (br s, 2H), 6.48 (d, J=8.46 Hz, 2H), 6.86 (d, J=8.09 Hz, 2H), 7.16 (d, J=5.88 Hz, 2H), 8.40 (d, J=5.88 Hz, 2H); EI-MS m/z 184 (M$^+$). This material was used in urea formation reactions without further purification.

A2. General Method for Substituted Aniline Formation Via Dissolving Metal Reduction of a Nitroarene

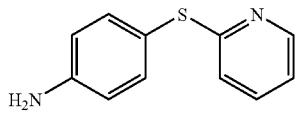

4-(2-Pyridinylthio)aniline: To a solution of 4-(2-pyridinylthio)-1-nitrobenzene (Menai ST 3355A; 0.220 g, 0.95 mmol) and H$_2$O (0.5 mL) in AcOH (5 mL) was added iron powder (0.317 g, 5.68 mmol) and the resulting slurry stirred for 16 h at room temp. The reaction mixture was diluted with EtOAc (75 mL) and H$_2$O (50 mL), basified to pH 10 by adding solid K$_2$CO$_3$ in portions (Caution: foaming). The organic layer was washed with a saturated NaCl solution, dried (MgSO$_4$), concentrated in vacuo. The residual solid was purified by MPLC (30% EtOAc/70% hexane) to give the desired product as a thick oil (0.135 g, 70%): TLC (30% EtOAc/70% hexanes) R$_f$ 0.20.

A3a. General Method for Substituted Aniline Formation Via Nitroarene Formation Through Nucleophilic Aromatic Substitution, Followed by Reduction

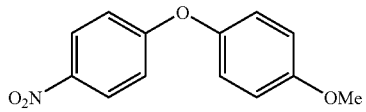

Step 1. 1-Methoxy-4-(4-nitrophenoxy)benzene: To a suspension of NaH (95%, 1.50 g, 59 mmol) in DMF (100 mL) at room temp. was added dropwise a solution of 4-methoxyphenol (7.39 g, 59 mmol) in DMF (50 mL). The reaction was stirred 1 h, then a solution of 1-fluoro-4-nitrobenzene (7.0 g, 49 mmol) in DMF (50 mL) was added dropwise to form a dark green solution. The reaction was heated at 95° C. overnight, then cooled to room temp., quenched with H$_2$O, and concentrated in vacuo. The residue was partitioned between EtOAc (200 mL) and H$_2$O (200 mL). The organic layer was sequentially washed with H$_2$O (2×200 mL), a saturated NaHCO$_3$ solution (200 mL), and a saturated NaCl solution (200 mL), dried (Na$_2$SO$_4$), and concentrated in vacuo. The residue was triturated (Et$_2$O/hexane) to afford 1-methoxy-4-(4-nitrophenoxy)benzene (12.2 g, 100%): $^1$H-NMR (CDCl$_3$) δ 3.83 (s, 3H), 6.93-7.04 (m, 6H), 8.18 (d, J=9.2 Hz, 2H); EI-MS m/z 245 (M$^+$).

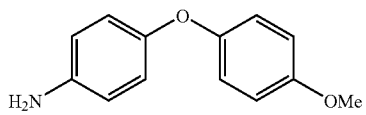

Step 2. 4-(4-Methoxyphenoxy)aniline: To a solution of 1-methoxy-4-(4-nitrophenoxy)benzene (12.0 g, 49 mmol) in EtOAc (250 mL) was added 5% Pt/C (1.5 g) and the resulting slurry was shaken under a H$_2$ atmosphere (50 psi) for 18 h. The reaction mixture was filtered through a pad of Celite® with the aid of EtOAc and concentrated in vacuo to give an oil which slowly solidified (10.6 g, 100%): $^1$H-NMR (CDCl$_3$) δ 3.54 (br s, 2H), 3.78 (s, 3H), 6.65 (d, J=8.8 Hz, 2H), 6.79-6.92 (m, 6H); EI-MS m/z 215 (M$^+$).

A3b. General Method for Substituted Aniline Formation Via Nitroarene Formation Through Nucleophilic Aromatic Substitution, Followed by Reduction

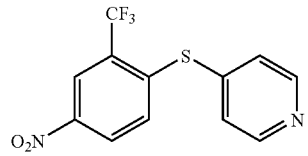

Step 1. 3-(Trifluoromethyl)-4-(4-pyridinylthio)nitrobenzene: A solution of 4-mercaptopyridine (2.8 g, 24 mmoles), 2-fluoro-5-nitrobenzotrifluoride (5 g, 23.5 mmoles), and potassium carbonate (6.1 g, 44.3 mmoles) in anhydrous DMF (80 mL) was stirred at room temperature and under argon overnight. TLC showed complete reaction. The mixture was diluted with Et$_2$O (100 mL) and water (100 mL) and the aqueous layer was back-extracted with Et$_2$O (2×100 mL). The organic layers were washed with a saturated NaCl solution (100 mL), dried (MgSO$_4$), and concentrated under reduced pressure. The solid residue was triturated with Et$_2$O to afford the desired product as a tan solid (3.8 g, 54%): TLC (30% EtOAc/70% hexane) R$_f$ 0.06; $^1$H-NMR (DMSO-d$_6$) δ 7.33 (dd, J=1.2, 4.2 Hz, 2H), 7.78 (d, J=8.7 Hz, 1H), 8.46 (dd, J=2.4, 8.7 Hz, 1H), 8.54-8.56 (m, 3H).

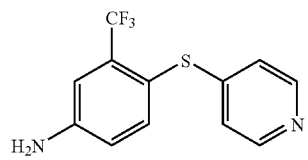

Step 2. 3-(Trifluoromethyl)-4-(4-pyridinylthio)aniline: A slurry of 3-trifluoromethyl-4-(4-pyridinylthio)nitrobenzene (3.8 g, 12.7 mmol), iron powder (4.0 g, 71.6 mmol), acetic acid (100 mL), and water (1 mL) were stirred at room temp. for 4 h. The mixture was diluted with Et$_2$O (100 mL) and water (100 mL). The aqueous phase was adjusted to pH 4 with a 4 N NaOH solution. The combined organic layers were washed with a saturated NaCl solution (100 mL), dried (MgSO$_4$), and concentrated under reduced pressure. The residue was filtered through a pad of silica (gradient from 50% EtOAc/50% hexane to 60% EtOAc/40% hexane) to afford the desired product (3.3 g): TLC (50% EtOAc/50% hexane) R$_f$ 0.10; $^1$H-NMR (DMSO-d$_6$) δ 6.21 (s, 2H), 6.84-6.87 (m, 3H), 7.10 (d, J=2.4 Hz, 1H), 7.39 (d, J=8.4 Hz, 1H), 8.29 (d, J=6.3 Hz, 2H).

A3c. General Method for Substituted Aniline Formation Via Nitroarene Formation Through Nucleophilic Aromatic Substitution, Followed by Reduction

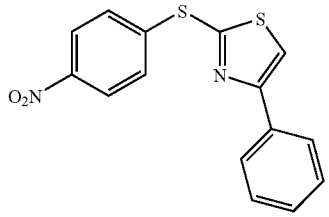

Step 1. 4-(2-(4-Phenyl)thiazolyl)thio-1-nitrobenzene: A solution of 2-mercapto-4-phenylthiazole (4.0 g, 20.7 mmoles) in DMF (40 mL) was treated with 1-fluoro-4-nitrobenzene (2.3 mL, 21.7 mmoles) followed by $K_2CO_3$ (3.18 g, 23 mmol), and the mixture was heated at approximately 65° C. overnight. The reaction mixture was then diluted with EtOAc (100 mL), sequentially washed with water (100 mL) and a saturated NaCl solution (100 mL), dried ($MgSO_4$) and concentrated under reduced pressure. The solid residue was triturated with a $Et_2O$/hexane solution to afford the desired product (6.1 g): TLC (25% EtOAc/75% hexane) $R_f$ 0.49; $^1$H-NMR ($CDCl_3$) δ 7.35-7.47 (m, 3H), 7.58-7.63 (m, 3H), 7.90 (d, J=6.9 Hz, 2H), 8.19 (d, J=9.0 Hz, 2H).

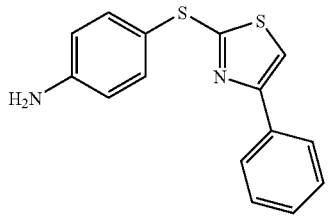

Step 2. 4-(2-(4-Phenyl)thiazolyl)thioaniline: 4-(2-(4-Phenyl)thiazolyl)thio-1-nitro-benzene was reduced in a manner analagous to that used in the preparation of 3-(trifluoromethyl)-4-(4-pyridinylthio)aniline: TLC (25% EtOAc/75% hexane) $R_f$ 0.18; $^1$H-NMR ($CDCl_3$) δ 3.89 (br s, 2H), 6.72-6.77 (m, 2H), 7.26-7.53 (m, 6H), 7.85-7.89 (m, 2H).

A3d. General Method for Substituted Aniline Formation Via Nitroarene Formation Through Nucleophilic Aromatic Substitution, Followed by Reduction

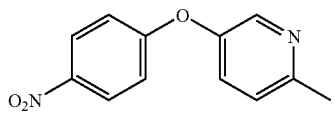

Step 1. 4-(6-Methyl-3-pyridinyloxy)-1-nitrobenzene: To a solution of 5-hydroxy-2-methylpyridine (5.0 g, 45.8 mmol) and 1-fluoro-4-nitrobenzene (6.5 g, 45.8 mmol) in anh DMF (50 mL) was added $K_2CO_3$ (13.0 g, 91.6 mmol) in one portion. The mixture was heated at the reflux temp. with stirring for 18 h and then allowed to cool to room temp. The resulting mixture was poured into water (200 mL) and extracted with EtOAc (3×150 mL). The combined organics were sequentially washed with water (3×100 mL) and a saturated NaCl solution (2×100 mL), dried ($Na_2SO_4$), and concentrated in vacuo to afford the desired product (8.7 g, 83%). This material was carried to the next step without further purification.

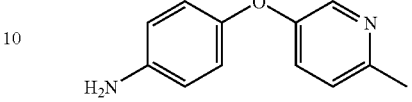

Step 2. 4-(6-Methyl-3-pyridinyloxy)aniline: A solution of 4-(6-methyl-3-pyridinyloxy)-1-nitrobenzene (4.0 g, 17.3 mmol) in EtOAc (150 mL) was added to 10% Pd/C (0.500 g, 0.47 mmol) and the resulting mixture was placed under a $H_2$ atmosphere (balloon) and was allowed to stir for 18 h at room temp. The mixture was then filtered through a pad of Celite® and concentrated in vacuo to afford the desired product as a tan solid (3.2 g, 92%): EI-MS m/z 200 ($M^+$).

A3e. General Method for Substituted Aniline Formation Via Nitroarene Formation Through Nucleophilic Aromatic Substitution, Followed by Reduction

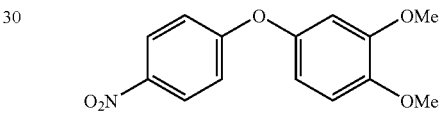

Step 1. 4-(3,4-Dimethoxyphenoxy)-1-nitrobenzene: To a solution of 3,4-dimethoxyphenol (1.0 g, 6.4 mmol) and 1-fluoro-4-nitrobenzene (700 µL, 6.4 mmol) in anh DMF (20 mL) was added $K_2CO_3$ (1.8 g, 12.9 mmol) in one portion. The mixture was heated at the reflux temp with stirring for 18 h and then allowed to cool to room temp. The mixture was then poured into water (100 mL) and extracted with EtOAc (3×100 mL). The combined organics were sequentially washed with water (3×50 mL) and a saturated NaCl solution (2×50 mL), dried ($Na_2SO_4$), and concentrated in vacuo to afford the desired product (0.8 g, 54%). The crude product was carried to the next step without further purification.

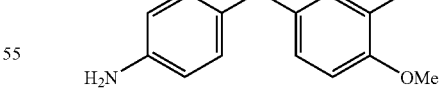

Step 2. 4-(3,4-Dimethoxyphenoxy)aniline: A solution of 4-(3,4-dimethoxy-phenoxy)-1-nitrobenzene (0.8 g, 3.2 mmol) in EtOAc (50 mL) was added to 10% Pd/C (0.100 g) and the resulting mixture was placed under a $H_2$ atmosphere (balloon) and was allowed to stir for 18 h at room temp. The mixture was then filtered through a pad of Celite® and concentrated in vacuo to afford the desired product as a white solid (0.6 g, 75%): EI-MS m/z 245 ($M^+$).

A3f. General Method for Substituted Aniline Formation Via Nitroarene Formation Through Nucleophilic Aromatic Substitution, Followed by Reduction

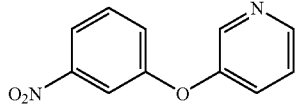

Step 1. 3-(3-Pyridinyloxy)-1-nitrobenzene: To a solution of 3-hydroxypyridine (2.8 g, 29.0 mmol), 1-bromo-3-nitrobenzene (5.9 g, 29.0 mmol) and copper(I) bromide (5.0 g, 34.8 mmol) in anh DMF (50 mL) was added $K_2CO_3$ (8.0 g, 58.1 mmol) in one portion. The resulting mixture was heated at the reflux temp. with stirring for 18 h and then allowed to cool to room temp. The mixture was then poured into water (200 mL) and extracted with EtOAc (3×150 mL). The combined organics were sequentially washed with water (3×100 mL) and a saturated NaCl solution (2×100 mL), dried ($Na_2SO_4$), and concentrated in vacuo. The resulting oil was purified by flash chromatography (30% EtOAc/70% hexane) to afford the desired product (2.0 g, 32%). This material was used in the next step without further purification.

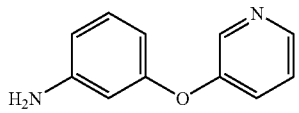

Step 2. 3-(3-Pyridinyloxy)aniline: A solution of 3-(3-pyridinyloxy)-1-nitrobenzene (2.0 g, 9.2 mmol) in EtOAc (100 mL) was added to 10% Pd/C (0.200 g) and the resulting mixture was placed under a $H_2$ atmosphere (balloon) and was allowed to stir for 18 h at room temp. The mixture was then filtered through a pad of Celite® and concentrated in vacuo to afford the desired product as a red oil (1.6 g, 94%): EI-MS m/z 186 ($M^+$).

A3g. General Method for Substituted Aniline Formation Via Nitroarene Formation Through Nucleophilic Aromatic Substitution, Followed by Reduction

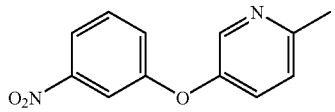

Step 1. 3-(5-Methyl-3-pyridinyloxy)-1-nitrobenzene: To a solution of 3-hydroxy-5-methylpyridine (5.0 g, 45.8 mmol), 1-bromo-3-nitrobenzene (12.0 g, 59.6 mmol) and copper(I) iodide (10.0 g, 73.3 mmol) in anh DMF (50 mL) was added $K_2CO_3$ (13.0 g, 91.6 mmol) in one portion. The mixture was heated at the reflux temp. with stirring for 18 h and then allowed to cool to room temp. The mixture was then poured into water (200 mL) and extracted with EtOAc (3×150 mL). The combined organics were sequentially washed with water (3×100 mL) and a saturated NaCl solution (2×100 mL), dried ($Na_2SO_4$), and concentrated in vacuo. The resulting oil was purified by flash chromatography (30% EtOAc/ 70% hexane) to afford the desired product (1.2 g, 13%).

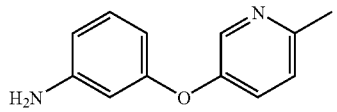

Step 2. 3-(5-Methyl-3-pyridinyloxy)-1-nitrobenzene: A solution of 3-(5-methyl-3-pyridinyloxy)-1-nitrobenzene (1.2 g, 5.2 mmol) in EtOAc (50 mL) was added to 10% Pd/C (0.100 g) and the resulting mixture was placed under a $H_2$ atmosphere (balloon) and was allowed to stir for 18 h at room temp. The mixture was then filtered through a pad of Celite® and concentrated in vacuo to afford the desired product as a red oil (0.9 g, 86%): CI-MS m/z 201 (($M+H)^+$).

A3h. General Method for Substituted Aniline Formation Via Nitroarene Formation Through Nucleophilic Aromatic Substitution, Followed by Reduction

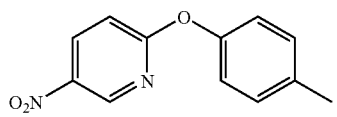

Step 1. 5-Nitro-2-(4-methylphenoxy)pyridine: To a solution of 2-chloro-5-nitropyridine (6.34 g, 40 mmol) in DMF (200 mL) were added of 4-methylphenol (5.4 g, 50 mmol, 1.25 equiv) and $K_2CO_3$ (8.28 g, 60 mmol, 1.5 equiv). The mixture was stirred overnight at room temp. The resulting mixture was treated with water (600 mL) to generate a precipitate. This mixture was stirred for 1 h, and the solids were separated and sequentially washed with a 1 N NaOH solution (25 mL), water (25 mL) and pet ether (25 mL) to give the desired product (7.05 g, 76%): mp 80-82° C.; TLC (30% EtOAc/70% pet ether) $R_f$ 0.79; $^1$H-NMR (DMSO-$d_6$) δ 2.31 (s, 3H), 7.08 (d, J=8.46 Hz, 2H), 7.19 (d, J=9.20 Hz, 1H), 7.24 (d, J=8.09 Hz, 2H), 8.58 (dd, J=2.94, 8.82 Hz, 1H), 8.99 (d, J=2.95 Hz, 1H); FAB-MS m/z (rel abundance) 231 (($M+H)^+$), 100%).

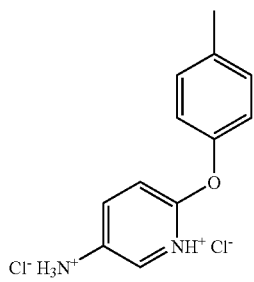

Step 2. 5-Amino-2-(4-methylphenoxy)pyridine Dihydrochloride: A solution 5-nitro-2-(4-methylphenoxy)pyridine (6.94 g, 30 mmol, 1 eq) and EtOH (10 mL) in EtOAc (190 mL) was purged with argon then treated with 10% Pd/C (0.60 g). The reaction mixture was then placed under a $H_2$ atmosphere and was vigorously stirred for 2.5 h. The reaction mixture was filtered through a pad of Celite®. A solution of HCl in $Et_2O$ was added to the filtrate was added dropwise. The resulting precipitate was separated and washed with EtOAc to give the desired product (7.56 g, 92%): mp 208-210° C. (dec); TLC (50% EtOAc/50% pet ether) $R_f$ 0.42; $^1$H-NMR (DMSO-$d_6$) δ 2.25 (s, 3H), 6.98 (d, J=8.45 Hz, 2H), 7.04 (d, J=8.82 Hz, 1H), 7.19 (d, J=8.09 Hz, 2H), 8.46 (dd, J=2.57, 8.46 Hz, 1H), 8.63 (d, J=2.57 Hz, 1H); EI-MS m/z (rel abundance) (M$^+$, 100%).

A3i. General Method for Substituted Aniline Formation Via Nitroarene Formation Through Nucleophilic Aromatic Substitution, Followed by Reduction

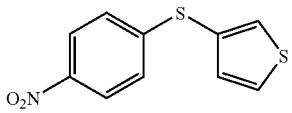

Step 1. 4-(3-Thienylthio)-1-nitrobenzene: To a solution of 4-nitrothiophenol (80% pure; 1.2 g, 6.1 mmol), 3-bromothiophene (1.0 g, 6.1 mmol) and copper(II) oxide (0.5 g, 3.7 mmol) in anhydrous DMF (20 mL) was added KOH (0.3 g, 6.1 mmol), and the resulting mixture was heated at 130° C. with stirring for 42 h and then allowed to cool to room temp. The reaction mixture was then poured into a mixture of ice and a 6N HCl solution (200 mL) and the resulting aqueous mixture was extracted with EtOAc (3×100 mL). The combined organic layers were sequentially washed with a 1M NaOH solution (2×100 mL) and a saturated NaCl solution (2×100 mL), dried (MgSO$_4$), and concentrated in vacuo. The residual oil was purified by MPLC (silica gel; gradient from 10% EtOAc/90% hexane to 5% EtOAc/95% hexane) to afford of the desired product (0.5 g, 34%). GC-MS m/z 237 (M$^+$).

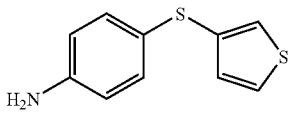

Step 2. 4-(3-Thienylthio)aniline: 4-(3-Thienylthio)-1-nitrobenzene was reduced to the aniline in a manner analogous to that described in Method A1.

A3j. General Method for Substituted Aniline Formation Via Nitroarene Formation Through Nucleophilic Aromatic Substitution, Followed by Reduction

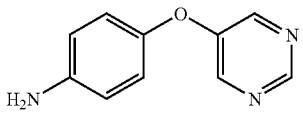

4-(5-Pyrimininyloxy)aniline: 4-Aminophenol (1.0 g, 9.2 mmol) was dissolved in DMF (20 mL) then 5-bromopyrimidine (1.46 g, 9.2 mmol) and K$_2$CO$_3$ (1.9 g, 13.7 mmol) were added. The mixture was heated to 100° C. for 18 h and at 130° C. for 48 h at which GC-MS analysis indicated some remaining starting material. The reaction mixture was cooled to room temp. and diluted with water (50 mL). The resulting solution was extracted with EtOAc (100 mL). The organic layer was washed with a saturated NaCl solution (2×50 mL), dried (MgSO$_4$), and concentrated in vacuo. The residual solids were purified by MPLC (50% EtOAc/50% hexanes) to give the desired amine (0.650 g, 38%).

A3k. General Method for Substituted Aniline Formation Via Nitroarene Formation Through Nucleophilic Aromatic Substitution, Followed by Reduction

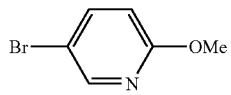

Step 1. 5-Bromo-2-methoxypyridine: A mixture of 2,5-dibromopyridine (5.5 g, 23.2 mmol) and NaOMe (3.76 g, 69.6 mmol) in MeOH (60 mL) was heated at 70° C. in a sealed reaction vessel for 42 h, then allowed to cool to room temp. The reaction mixture was treated with water (50 mL) and extracted with EtOAc (2×100 mL). The combined organic layers were dried (Na$_2$SO$_4$) and concentrated under reduced pressure to give a pale yellow, volatile oil (4.1 g, 95% yield): TLC (10% EtOAc/90% hexane) $R_f$ 0.57.

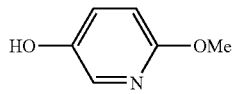

Step 2. 5-Hydroxy-2-methoxypyridine: To a stirred solution of 5-bromo-2-methoxypyridine (8.9 g, 47.9 mmol) in THF (175 mL) at −78° C. was added an n-butyllithium solution (2.5 M in hexane; 28.7 mL, 71.8 mmol) dropwise and the resulting mixture was allowed to stir at −78° C. for 45 min. Trimethyl borate (7.06 mL, 62.2 mmol) was added via syringe and the resulting mixture was stirred for an additional 2 h. The bright orange reaction mixture was warmed to 0° C. and was treated with a mixture of a 3 N NaOH solution (25 mL, 71.77 mmol) and a hydrogen peroxide solution (30%; approx. 50 mL). The resulting yellow and slightly turbid reaction mixture was warmed to room temp. for 30 min and then heated to the reflux temp. for 1 h. The reaction mixture was then allowed to cool to room temp. The aqueous layer was neutralized with a 1N HCl solution then extracted with Et$_2$O (2×100 mL). The combined organic layers were dried (Na$_2$SO$_4$) and concentrated under reduced pressure to give a viscous yellow oil (3.5 g, 60%).

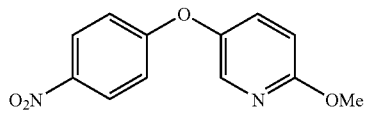

Step 3. 4-(5-(2-Methoxy)pyridyl)oxy-1-nitrobenzene: To a stirred slurry of NaH (97%, 1.0 g, 42 mmol) in anh DMF (100 mL) was added a solution of 5-hydroxy-2-methoxypyridine (3.5 g, 28 mmol) in DMF (100 mL). The resulting mixture was allowed to stir at room temp. for 1 h, 4-fluoronitrobenzene (3 mL, 28 mmol) was added via syringe. The reaction mixture was heated to 95° C. overnight, then treated with water (25 mL) and extracted with EtOAc (2×75 mL). The organic layer was dried (MgSO$_4$) and concentrated under reduced pressure. The residual brown oil was crystalized EtOAc/hexane) to afford yellow crystals (5.23 g, 75%).

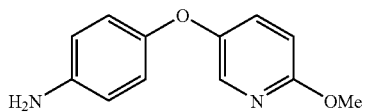

Step 4. 4-(5-(2-Methoxy)pyridyl)oxyaniline: 4-(5-(2-Methoxy)pyridyl)oxy-1-nitrobenzene was reduced to the aniline in a manner analogous to that described in Method A3d, Step2.

A4a. General Method for Substituted Aniline Synthesis Via Nucleophilic Aromatic Substitution Using a Halopyridine

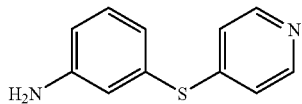

3-(4-Pyridinylthio)aniline: To a solution of 3-aminothiophenol (3.8 mL, 34 mmoles) in anh DMF (90 mL) was added 4-chloropyridine hydrochloride (5.4 g, 35.6 mmoles) followed by $K_2CO_3$ (16.7 g, 121 mmoles). The reaction mixture was stirred at room temp. for 1.5 h, then diluted with EtOAc (100 mL) and water (100 mL). The aqueous layer was back-extracted with EtOAc (2×100 mL). The combined organic layers were washed with a saturated NaCl solution (100 mL), dried ($MgSO_4$), and concentrated under reduced pressure. The residue was filtered through a pad of silica (gradient from 50% EtOAc/50% hexane to 70% EtOAc/30% hexane) and the resulting material was triturated with a $Et_2O$/hexane solution to afford the desired product (4.6 g, 66%): TLC (100% ethyl acetate) $R_f$ 0.29; $^1$H-NMR (DMSO-$d_6$) δ 5.41 (s, 2H), 6.64-6.74 (m, 3H), 7.01 (d, J=4.8, 2H), 7.14 (t, J=7.8 Hz, 1H), 8.32 (d, J=4.8, 2H).

A4b. General Method for Substituted Aniline Synthesis Via Nucleophilic Aromatic Substitution Using a Halopyridine

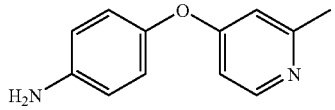

4-(2-Methyl-4-pyridinyloxy)aniline: To a solution of 4-aminophenol (3.6 g, 32.8 mmol) and 4-chloropicoline (5.0 g, 39.3 mmol) in anh DMPU (50 mL) was added potassium tert-butoxide (7.4 g, 65.6 mmol) in one portion. The reaction mixture was heated at 100° C. with stirring for 18 h, then was allowed to cool to room temp. The resulting mixture was poured into water (200 mL) and extracted with EtOAc (3×150 mL). The combined extracts were sequentially washed with water (3×100 mL) and a saturated NaCl solution (2×100 mL), dried ($Na_2SO_4$), and concentrated in vacuo. The resulting oil was purified by flash chromatography (50% EtOAc/50% hexane) to afford the desired product as a yellow oil (0.7 g, 9%): CI-MS m/z 201 ((M+H)$^+$).

A4c. General Method for Substituted Aniline Synthesis Via Nucleophilic Aromatic Substitution Using a Halopyridine

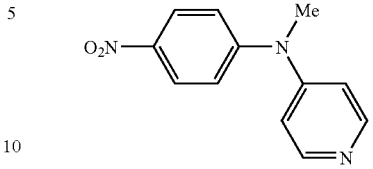

Step 1. Methyl(4-nitrophenyl)-4-pyridylamine: To a suspension of N-methyl-4-nitroaniline (2.0 g, 13.2 mmol) and $K_2CO_3$ (7.2 g, 52.2 mmol) in DMPU (30 mL) was added 4-chloropyridine hydrochloride (2.36 g, 15.77 mmol). The reaction mixture was heated at 90° C. for 20 h, then cooled to room temperature. The resulting mixture was diluted with water (100 mL) and extracted with EtOAc (100 mL). The organic layer was washed with water (100 mL), dried ($Na_2SO_4$) and concentrated under reduced pressure. The residue was purified by column chromatography (silica gel, gradient from 80% EtOAc/20% hexanes to 100% EtOAc) to afford methyl(4-nitrophenyl)-4-pyridylamine (0.42 g)

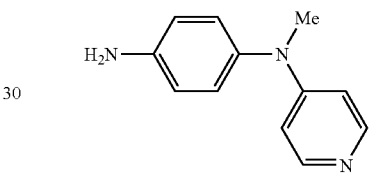

Step 2. Methyl(4-aminophenyl)-4-pyridylamine: Methyl(4-nitrophenyl)-4-pyridylamine was reduced in a manner analogous to that described in Method A1.

A5. General Method of Substituted Aniline Synthesis Via Phenol Alkylation Followed by Reduction of a Nitroarene

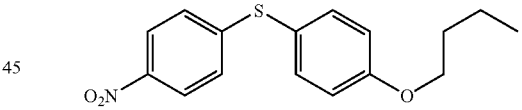

Step 1. 4-(4-Butoxyphenyl)thio-1-nitrobenzene: To a solution of 4-(4-nitrophenyl-thio)phenol (1.50 g, 6.07 mmol) in anh DMF (75 ml) at 0° C. was added NaH (60% in mineral oil, 0.267 g, 6.67 mmol). The brown suspension was stirred at 0° C. until gas evolution stopped (15 min), then a solution of iodobutane (1.12 g, 690 ml, 6.07 mmol) in anh DMF (20 mL) was added dropwise over 15 min at 0° C. The reaction was stirred at room temp. for 18 h at which time TLC indicated the presence of unreacted phenol, and additional iodobutane (56 mg, 0.035 mL, 0.303 mmol, 0.05 equiv) and NaH (13 mg, 0.334 mmol) were added. The reaction was stirred an additional 6 h at room temp., then was quenched by the addition of water (400 mL). The resulting mixture was extracted with $Et_2O$ (2×500 mL). The combined organics were washed with water (2×400 mL), dried ($MgSO_4$), and concentrated under reduced pressure to give a clear yellow oil, which was purified by silica gel chromatography (gradient from 20% EtOAc/80% hexane to 50% EtOAc/50% hexane) to give the product as a yellow solid (1.24 g, 67%):

TLC (20% EtOAc/80% hexane) $R_f$ 0.75; $^1$H-NMR (DMSO-$d_6$) δ 0.92 (t, J=7.5 Hz, 3H), 1.42 (app hex, J=7.5 Hz, 2H), 1.70 (m, 2H), 4.01 (t, J=6.6 Hz, 2H), 7.08 (d, J=8.7 Hz, 2H), 7.17 (d, J=9 Hz, 2H), 7.51 (d, J=8.7 Hz, 2H), 8.09 (d, J=9 Hz, 2H).

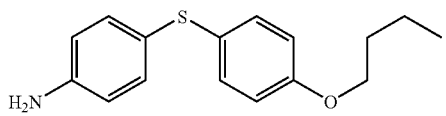

Step 2. 4-(4-Butoxyphenyl)thioaniline: 4-(4-Butoxyphenyl)thio-1-nitrobenzene was reduced to the aniline in a manner analagous to that used in the preparation of 3-(trifluoromethyl)-4-(4-pyridinylthio)aniline (Method A3b, Step 2): TLC (33% EtOAc/77% hexane) $R_f$ 0.38.

A6. General Method for Synthesis of Substituted Anilines by the Acylation of Diaminoarenes

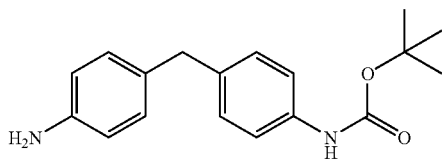

4-(4-tert-Butoxycarbamoylbenzyl)aniline: To a solution of 4,4'-methylenedianiline (3.00 g, 15.1 mmol) in anh THF (50 mL) at room temp was added a solution of di-tert-butyl dicarbonate (3.30 g, 15.1 mmol) in anh THF (10 mL). The reaction mixture was heated at the reflux temp. for 3 h, at which time TLC indicated the presence of unreacted methylenedianiline. Additional di-tert-butyl dicarbonate (0.664 g, 3.03 mmol, 0.02 equiv) was added and the reaction stirred at the reflux temp. for 16 h. The resulting mixture was diluted with $Et_2O$ (200 mL), sequentially washed with a saturated $NaHCO_3$ solution (100 ml), water (100 mL) and a saturated NaCl solution (50 mL), dried (MgSO4), and concentrated under reduced pressure. The resulting white solid was purified by silica gel chromatography (gradient from 33% EtOAc/67% hexane to 50% EtOAc/50% hexane) to afford the desired product as a white solid (2.09 g, 46%): TLC (50% EtOAc/50% hexane) $R_f$ 0.45; $^1$H-NMR (DMSO-$d_6$) δ 1.43 (s, 9H), 3.63 (s, 2H), 4.85 (br s, 2H), 6.44 (d, J=8.4 Hz, 2H), 6.80 (d, J=8.1 Hz, 2H), 7.00 (d, J=8.4 Hz, 2H), 7.28 (d, J=8.1 Hz, 2H), 9.18 (br s, 1H); FAB-MS m/z 298 ($M^+$).

A7. General Method for the Synthesis of Aryl Amines Via Electrophilic Nitration Followed by Reduction

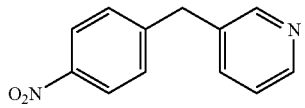

Step 1. 3-(4-Nitrobenzyl)pyridine: A solution of 3-benzylpyridine (4.0 g, 23.6 mmol) and 70% nitric acid (30 mL) was heated overnight at 50° C. The resulting mixture was allowed to cool to room temp. then poured into ice water (350 mL). The aqueous mixture then made basic with a 1N NaOH solution, then extracted with $Et_2O$ (4×100 mL). The combined extracts were sequentially washed with water (3×100 mL) and a saturated NaCl solution (2×100 mL), dried ($Na_2SO_4$), and concentrated in vacuo. The residual oil was purified by MPLC (silica gel; 50% EtOAc/50% hexane) then recrystallization (EtOAc/hexane) to afford the desired product (1.0 g, 22%): GC-MS m/z 214 ($M^+$).

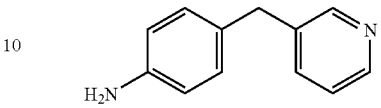

Step 2. 3-(4-Pyridinyl)methylaniline: 3-(4-Nitrobenzyl)pyridine was reduced to the aniline in a manner analogous to that described in Method A1.

A8. General Method for Synthesis of Aryl Amines Via Substitution with Nitrobenzyl Halides Followed by Reduction

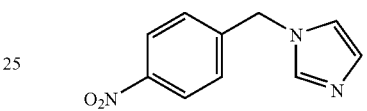

Step 1. 4-(1-Imidazolylmethyl)-1-nitrobenzene: To a solution of imidazole (0.5 g, 7.3 mmol) and 4-nitrobenzyl bromide (1.6 g, 7.3 mmol) in anh acetonitrile (30 mL) was added $K_2CO_3$ (1.0 g, 7.3 mmol). The resulting mixture was stirred at room temp. for 18 h and then poured into water (200 mL) and the resulting aqueous solution was extracted with EtOAc (3×50 mL). The combined organic layers were sequentially washed with water (3×50 mL) and a saturated NaCl solution (2×50 mL), dried ($MgSO_4$), and concentrated in vacuo. The residual oil was purified by MPLC (silica gel; 25% EtOAc/75% hexane) to afford the desired product (1.0 g, 91%): EI-MS m/z 203 ($M^+$).

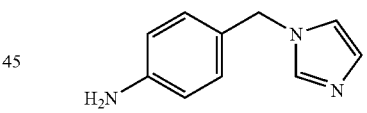

Step 2. 4-(1-Imidazolylmethyl)aniline: 4-(1-Imidazolylmethyl)-1-nitrobenzene was reduced to the aniline in a manner analogous to that described in Method A2.

A9. Formation of Substituted Hydroxymethylanilines by Oxidation of Nitrobenzyl Compounds Followed by Reduction

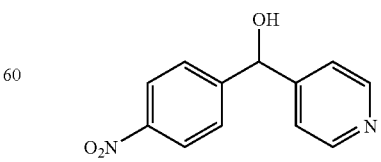

Step 1. 4-(1-Hydroxy-1-(4-pyridyl)methyl-1-nitrobenzene: To a stirred solution of 3-(4-nitrobenzyl)pyridine (6.0 g, 28 mmol) in CH₂Cl₂ (90 mL) was added m-CPBA (5.80 g, 33.6 mmol) at 10° C., and the mixture was stirred at room temp. overnight. The reaction mixture was successively washed with a 10% NaHSO₃ solution (50 mL), a saturated K₂CO₃ solution (50 mL) and a saturated NaCl solution (50 mL), dried (MgSO4) and concentrated under reduced pressure. The resulting yellow solid (2.68 g) was dissolved in anh acetic anhydride (30 mL) and heated at the reflux temperature overnight. The mixture was concentrated under reduced pressure. The residue was dissolved in MeOH (25 mL) and treated with a 20% aqueous NH₃ solution (30 mL). The mixture was stirred at room temp. for 1 h, then was concentrated under reduced pressure. The residue was poured into a mixture of water (50 mL) and CH₂Cl₂ (50 mL). The organic layer was dried (MgSO₄), concentrated under reduced pressure, and purified by column chromatography (80% EtOAc/20% hexane) to afford the desired product as a white solid. (0.53 g, 8%): mp 110-118° C.; TLC (80% EtOAc/20% hexane) R$_f$0.12; FAB-MS m/z 367 ((M+H)⁺, 100%).

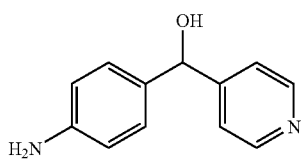

Step 2. 4-(1-Hydroxy-1-(4-pyridyl)methylaniline: 4-(1-Hydroxy-1-(4-pyridyl)-methyl-1-nitrobenzene was reduced to the aniline in a manner analogous to that described in Method A3d, Step2.

A10. Formation of 2-(N-methylcarbamoyl)pyridines via the Menisci reaction

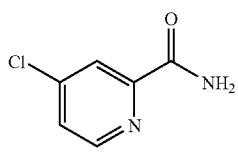

Step 1. 2-(N-methylcarbamoyl)-4-chloropyridine. (Caution: this is a highly hazardous, potentially explosive reaction.) To a solution of 4-chloropyridine (10.0 g) in N-methylformamide (250 mL) under argon at ambient temp was added conc. H₂SO₄ (3.55 mL) (exotherm). To this was added H₂O₂ (17 mL, 30% wt in H2O) followed by FeSO₄7H₂O (0.55 g) to produce an exotherm. The reaction was stirred in the dark at ambient temp for 1 h then was heated slowly over 4 h at 45° C. When bubbling subsided, the reaction was heated at 60° C. for 16 h. The opaque brown solution was diluted with H2O (700 mL) followed by a 10% NaOH solution (250 mL). The aqueous mixture was extracted with EtOAc (3×500 mL) and the organic layers were washed separately with a saturated NaCl solution (3×150 mL. The combined organics were dried (MgSO₄) and filtered through a pad of silica gel eluting with EtOAc. The solvent was removed in vacuo and the brown residue was purified by silica gel chromatography (gradient from 50% EtOAc/50% hexane to 80% EtOAc/20% hexane). The resulting yellow oil crystallized at 0° C. over 72 h to give 2-(N-methylcarbamoyl)-4-chloropyridine in yield (0.61 g, 5.3%): TLC (50% EtOAc/50% hexane) R$_f$ 0.50; MS; ¹H NMR (CDCl₃): δd 8.44 (d, 1H, J=5.1 Hz, CHN), 8.21 (s, 1H, CHCCO), 7.96 (b s, 1H, NH), 7.43 (dd, 1H, J=2.4, 5.4 Hz, ClCHCN), 3.04 (d, 3H, J=5.1 Hz, methyl); CI-MS m/z 171 ((M+H)+).

A11. General Method for the Synthesis of δ-Sulfonylphenyl Anilines

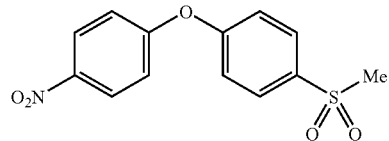

Step 1. 4-(4-Methylsulfonylphenoxy)-1-nitrobenzene: To a solution of 4-(4-methylthiophenoxy)-1-ntirobenzene (2 g, 7.66 mmol) in CH₂Cl₂ (75 mL) at 0° C. was slowly added mCPBA (57-86%, 4 g), and the reaction mixture was stirred at room temperature for 5 h. The reaction mixture was treated with a 1 N NaOH solution (25 mL). The organic layer was sequentially washed with a 1N NaOH solution (25 mL), water (25 mL) and a saturated NaCl solution (25 mL), dried (MgSO₄), and concentrated under reduced pressure to give 4-(4-methylsulfonylphenoxy)-1-nitrobenzene as a solid (2.1 g).

Step 2. 4-(4-Methylsulfonylphenoxy)-1-aniline: 4-(4-Methylsulfonylphenoxy)-1-nitrobenzene was reduced to the aniline in a manner anaologous to that described in Method A3d, step 2.

A12. General Method for Synthesis of δ-Alkoxy-δ-Carboxyphenyl Anilines

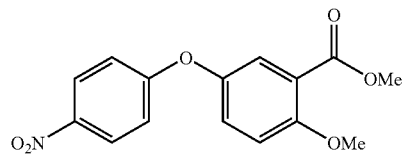

Step 1. 4-(3-Methoxycarbonyl-4-methoxyphenoxy)-1-nitrobenzene: To a solution of δ-(3-carboxy-4-hydroxyphenoxy)-1-nitrobenzene (prepared in a manner analogous to that described in Method A3a, step 1, 12 mmol) in acetone (50 mL) was added K₂CO₃ (5 g) and dimethyl sulfate (3.5 mL). The resulting mixture was heated at the reflux temperature overnight, then cooled to room temperature and filtered through a pad of Celite®. The resulting solution was concentrated under reduced pressure, absorbed onto silica gel, and purified by column chromatography (50% EtOAc/ 50% hexane) to give 4-(3-methoxycarbonyl-4-methoxyphenoxy)-1-nitrobenzene as a yellow powder (3 g): mp 115-118° C.

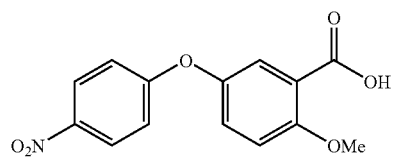

Step 2. 4-(3-Carboxy-4-methoxyphenoxy)-1-nitrobenzene: A mixture of 4-(3-methoxycarbonyl-4-methoxyphenoxy)-1- nitrobenzene (1.2 g), KOH (0.33 g), and water (5 mL) in MeOH (45 mL) was stirred at room temperature overnight and then heated at the reflux temperature for 4 h. The resulting mixture was cooled to room temperature and concentrated under reduced pressure. The residue was dissolved in water (50 mL), and the aqueous mixture was made acidic with a 1N HCl solution. The resulting mixture was extracted with EtOAc (50 mL). The organic layer was dried (MgSO$_4$) and concentrated under reduced pressure to give 4-(3-carboxy-4-methoxyphenoxy)-1-nitrobenzene (1.04 g).

B. General Methods of Urea Formation

B1. Reaction of a Heterocyclic Amine with an Aryl Isocyanate

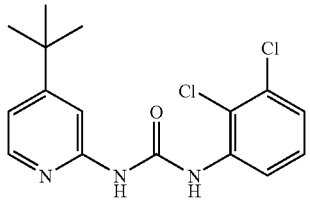

N-(4-tert-butylpyridyl)-N'-(2,3-dichlorophenyl) urea: A solution of 2-amino-4-tert-butylpyridine (192 mg) and 2,3-dichlorophenyl isocyanate (240 mg) in anh. toluene (15 mL) was heated at 70° C. under argon for 24 h. The resulting mixture was diluted with EtOAc (200 mL) then washed with water (125 mL). The organic layer was dried (MgSO$_4$) and concentrated under reduced pressure to give a gum. Trituration of the gum with hexanes afforded N-(4-tert-butylpyridyl)-N'-(2,3-dichlorophenyl) urea as a white solid (394 mg, 91%): TLC (2:1 hexanes/ethyl acetate) R$_f$ 0.40; FAB-MS m/z 338 ((M+H)$^+$).

B2a. Reaction of a Heterocyclic Amine with N,N'-Carbonyldiimidazole Followed By Reaction with a Substituted Aniline

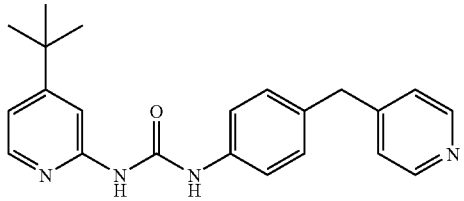

N-(4-tert-butylpyridyl)-N'-(4-(4-pyridinylmethyl)phenyl urea: To a stirring solution of 4-tert-butyl-2-aminopyridine (192 mg) in anh. CH$_2$Cl$_2$ (15 mL) under argon at 0° C. was added CDI (207 mg). The resulting solution was allowed to warm to ambient temp over 2 h. To this mixture was added 4-(4-pyridylmethyl)aniline (prepared according to Method A1, 235 mg). The resulting solution was stirred at room temperature for 24 h, then was quenched with water (125 mL). The resulting mixture was extracted with EtOAc (200 mL). The organic layer was washed with water (100 mL), dried (MgSO$_4$) and concentrated under reduced pressure. The residue was purified by chromatography (SiO$_2$, EtOAc) to afford N-(4-tert-butylpyridyl)-N'-(4-(4-pyridinylmethyl) phenyl urea as a white solid (200 mg, 43%): TLC (EtOAc) R$_f$ 0.47; FAB-MS m/z 361 ((M+H)$^+$).

B2b. Reaction of a Heterocyclic Amine with N,N'-Carbonyldiimidazole Followed by Reaction with a Substituted Aniline

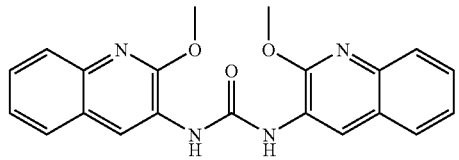

N,N'-(Bis(3-(2-methoxyquinolinyl)) urea): To a stirring solution of 3-amino-2-methoxyquinoline (138 mg) in anh. CH$_2$Cl$_2$ (15 mL) under argon at 0° C. was added CDI (128 mg). The resulting solution was warmed to ambient temp over 1 h. After 16 h 4-(2-N-Methylcarbamyl-4-pyridyloxy) aniline (175 mg) was added and the resulting yellow solution was stirred at room temperature under argon for 72 h. The solution was treated with water (125 mL) and the resulting mixture was extracted with EtOAc (2×150 mL). The combined organics were washed with a saturated NaCl solution (100 mL), dried (MgSO$_4$) and concentrated under reduced pressure. The residue was triturated with a 10% hexane/90% EtOAc solution. The resulting white crystals were washed with EtOAc. The resulting filtrate was purified by chromatography (SiO$_2$, 50% EtOAc/50% hexane) to give N,N'-(bis(3-(2-methoxyquinolinyl)) urea) (30 mg, 20% yield): TLC (50% EtOAc/50% hexane) R$_f$ 0.45; HPLC ES-MS m/z 375 ((M+H)$^+$).

B2c. Reaction of a Heterocyclic Amine with N,N'-Carbonyldiimidazole Followed by Reaction with a Substituted Aniline

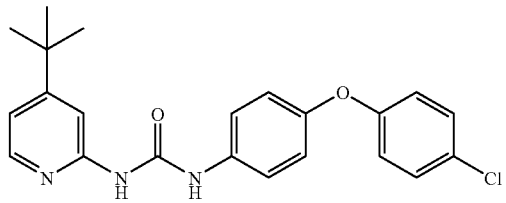

N-(4-tert-Butylpyridyl)-N'-(4-(4-chlorophenoxy)phenyl) urea: A solution of 4-tert-butyl-2-aminopyridine (0.177 g, 1.18 mmol, 1 equiv.) in 1.2 mL of anh. CH$_2$Cl$_2$ (1.2 mL) was added to CDI (0.200 g, 1.24 mmol, 1.05 equiv) and the mixture was allowed to stir under argon at room temperature 1 d. To the resulting solution was added 4-(4-chlorophenoxy)aniline (0.259 g, 1.18 mmol, 1 equiv.) in one portion. The resulting mixture was stirred at room temperature for 1 d, then was treated with a 10% citric acid solution (2 mL) and allowed to stir for 1 h. The resulting organic layer was extracted with EtOAc (3×5 mL). The combined organic layers were dried (MgSO$_4$) and concentrated in vacuo. The resultant residue was treated with CH$_2$Cl$_2$ (10 mL) and a 1 N aqueous NaOH solution. This mixture was allowed to stir overnight. The resulting organic layer was extracted with CH$_2$Cl$_2$ (3×5 mL). The combined organic layers were (MgSO$_4$) and concentrated in vacuo. The resultant solids were suspended in diethyl ether (10 mL) and sonicated for 15 minutes. The resulting white solids were dried to give N-(4-tert-butylpyridyl)-N'-(4-(4-chlorophenoxy)phenyl) urea (42 mg, 9%): mp 198-199° C.

B3. Reaction of Substituted Aniline with N,N'-Carbonyldiimidazole Followed by Reaction with a Heterocyclic Amine

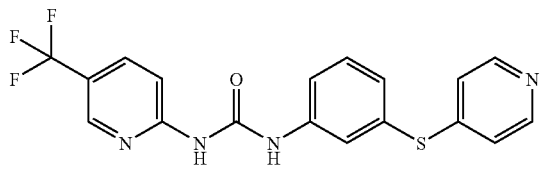

N-(2-(5-trifluoromethyl)pyridyloxy)-N'-(3-(4-pyridylthio) phenyl) urea: A solution of 3-(4-pyridylthio)aniline (300 mg, 1.48 mmoles) in $CH_2Cl_2$ (12 mL) was treated with CDI (253 mg, 1.56 mmoles). The solution was stirred at room temperature and under argon for 2 h. The resulting mixture was treated with 2-amino-5-(trifluoromethyl)pyridine (238 mg, 1.47 mmoles) and heated at 40° C. overnight. The reaction mixture was then diluted with EtOAc (25 mL), washed with water (10 mL) and a saturated NaCl solution m(25 mL), dried ($MgSO_4$), and concentrated under reduced pressure. The residue was purified by column chromatography ($SiO_2$; gradient from 70% EtOAc/30% $CH_2Cl_2$ to 100% EtOAc to give N-(2-(5-trifluoromethyl)pyridyloxy)-N'-(3-(4-pyridylthio)phenyl) urea (103 mg): TLC (50% EtOAc/50% $CH_2Cl_2$) $R_f$ 0.33; $^1$H-NMR (DMSO-$d_6$) δ 6.06 (d, J=6 Hz, 2H), 7.25 (dt, J=1.2,7.8 Hz, 1H), 7.48 (t, J=8.1 Hz, 1H), 7.59-7.63 (m, 1H), 7.77 (d, J=8.7 Hz, 1H), 7.86 (t, J=1.8 Hz, 1H), 8.12 (dd, J=2.7,9.3 Hz, 1H), 8.37 (d, J=6.3 Hz, 2H), 8.67 (bs, 1H), 9.88 (s, 1H), 10.26 (s, 1H); FAB-MS m/z 391 ((M+H)$^+$).

B4. Reaction of a Heterocyclic Amine with Phosgene, Followed by Reaction with a Substituted Aniline

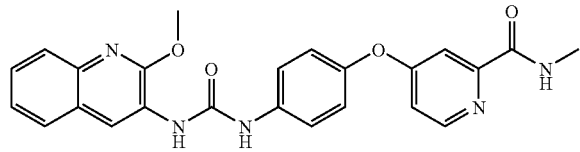

N-(3-(2-methoxyquinolinyl)-N'-(4-(4-(2-N-Methylcarbamyl-4-pyridyloxy)phenyl) urea: To a stirring solution of phosgene (20% in toluene, 1.38 mL) in anh. $CH_2Cl_2$ (20 ml) at 0° C. under argon was added anh. pyridine (207 mg) followed by 3-amino-2-methoxyquinoline (456 mg). The resulting solution was warmed to ambient temperature over 1 h, then concentrated in vacuo at ambient temperature to give a white solid. The solid was dried under vacuum for 15 min then suspended in anh toluene (20 mL). To the resulting slurry was added 4-(4-(2-(methylcarbamoyl)pyridyloxy) aniline (prepared according to Method A2, 300 mg) and the reaction heated under argon at 80° C. for 20 h. The resulting mixture was diluted with water (200 mL), then treated with a saturated $NaHCO_3$ solution (10 mL) and extracted with EtOAc (2×300 mL). The combined organic layers were washed with a saturated NaCl solution (100 mL), dried (MgSO4) and concentrated under reduced pressure. The solid yellow residue was purified by chromatography ($SiO_2$, gradient from 50% EtOAc/50% hexane to 100% EtOAc), followed by recrystallization from diethyl ether and hexane to give N-(3-(2-methoxyquinolinyl)-N'-(4-(4-(2-N-Methylcarbamyl-4-pyridyloxy)phenyl) urea as a white solid (140 mg, 25%): TLC (EtOAc) $R_f$ 0.52; FAB-MS m/z 430 ((M+H)$^+$).

SPECIFIC COMPOUND PREPARATIONS

Descriptions of the detailed preparative steps used to prepare the specific compounds listed in Tables 1-4 are provided below. Many of the compounds listed in the Tables can be synthesized following a variety of methods. The specific examples below are therefore provided by way of illustration only and should not be construed to limit the scope of the invention in any way.

Entry 5: N-(4-tert-Butylpyridyl)-N'-(4-(4-pyridinylmethyl) phenyl urea was prepared according to Method B2a.

Entry 6: 4-tert-Butyl-2-aminopyridine was reacted with 4-phenoxyaniline according to Method B2c to afford the urea.

Entry 7: 4-tert-Butyl-2-aminopyridine was reacted with 4-(4-methylphenoxy)aniline according to Method B2c to afford the urea.

Entry 8: N-(4-tert-Butylpyridyl)-N'-(4-(4-chlorophenoxy) phenyl) urea was prepared according to Method B2c.

Entry 10: 4-(4-Aminophenoxy)pyridine was prepared starting from 4-hydroxypyridine and 1-bromo-3-nitrobenzene according to Method A3F. 4-tert-Butyl-2-aminopyridine was reacted with 4-(4-aminophenoxy)pyridine according to Method B2a to afford the urea.

Entry 11: 4-(4-Pyridylthio)aniline was prepared starting from 4-aminothiophenol and 4-chloropyridine hydrochloride according to Method A4a. 4-tert-Butyl-2-aminopyridine was reacted with 4-(4-pyridylthio)aniline according to Method B2c to afford the urea.

Entry 12: 4-(4-Pyridylthio)aniline was prepared starting from 4-aminothiophenol and 4-chloropyridine hydrochloride according to Method A4a. 4-tert-Butyl-2-aminopyridine was reacted with 3-(4-pyridylthio)aniline according to Method B2c to afford the urea.

Entry 20: 4-(4-Aminophenoxy)pyridine was prepared starting from 4-hydroxypyridine and 1-bromo-3-nitrobenzene according to Method A3f. 3-Aminoisoquinoline was reacted with 4-(4-aminophenoxy)pyridine according to Method B2a to afford the urea.

Entry 22: N,N'-(Bis(3-(2-methoxyquinolinyl)) urea) was prepared according to Method B2b.

Entry 23: 3-Amino-2-methoxyquinoline and 4-(4-pyridylmethyl)aniline were reacted according to Method B3 to afford the urea.

Entry 24: 3-Amino-2-methoxyquinoline was reacted with 4-(4-pyridylcarbonyl)aniline according to Method B4 to afford the urea.

Entry 25: 4-(4-Pyridyloxy)aniline was prepared starting from 4-hydroxypyridine and 1-fluoro-4-nitrobenzene according to Method A3d. 3-Amino-2-methoxyquinoline was reacted with 4-(4-pyridyloxy)aniline according to Method B2c to afford the urea.

Entry 26: 3-Amino-2-methoxyquinoline was reacted with 4-((4-methoxyphenyl)methylamino)aniline according to Method B4 to afford the urea.

Entry 27: 3-(4-Pyridylthio)aniline was prepared according to Method A4a. 3-Amino-2-methoxyquinoline and 3-(4-pyridylmethyl)aniline were reacted according to Method B3 to afford the urea.

Entry 28: 4-(4-Pyridyloxy)aniline was prepared starting from 4-hydroxypyridine and 1-fluoro-4-nitrobenzene according to Method A3d. 1-(4-Methylpiperazinyl)-3-aminoisoquinoline was reacted with 4-(4-aminophenoxy) pyridine according to Method B2a to afford the urea.

The following compounds have been synthesized according to the General Methods listed above:
TABLE 1
4-tert-Butyl-2-pyridyl Ureas
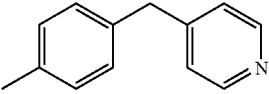
| Entry | R | mp (° C.) | HPLC (min.) | TLC Rf | TLC Solvent System | Mass Spec. [Source] |
|---|---|---|---|---|---|---|
| 5 | 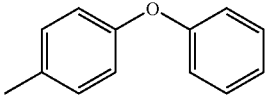 | | | 0.47 | 100% EtOAc | 361 (M + H) + (FAB) |
| 6 | 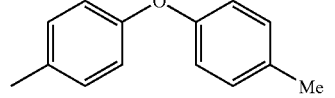 | 179-180 | | 0.58 | 5% MeOH/ 95% CH2Cl2 | 362 (M + H) + (FAB) |
| 7 | 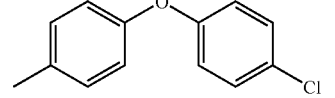 | 190-191 | | 0.46 | 5% MeOH/ 95% CH2Cl2 | 376 (M + H) + (FAB) |
| 8 | 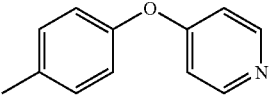 | 198-199 | | 0.76 | 5% MeOH/ 95% CH2Cl2 | 396 (M + H) + (FAB) |
| 10 | 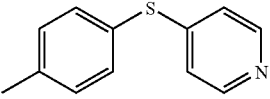 | | | 0.40 | 100% EtOAc | 363 (M + H) + (FAB) |
| 11 | 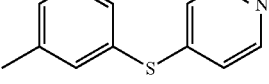 | 208-212 | | 0.39 | 5% MeOH/ 95% CH2Cl2 | 379 (M + H) + (HPLC ES-MS) |
| 12 |  | 196-197 | | 0.37 | 5% MeOH/ 95% CH2Cl2 | 379 (M + H) + (FAB) |

TABLE 2
3-Isoquinolyl Ureas
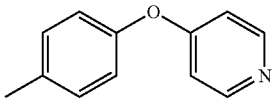
| Entry | R | mp (° C.) | HPLC (min.) | TLC $R_f$ | TLC Solvent System | Mass Spec. [Source] |
|---|---|---|---|---|---|---|
| 20 | 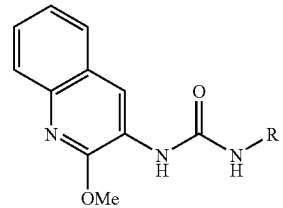 | | | 0.27 | 100% EtOAc | 357 (M + H) + (FAB) |
TABLE 3
2-Methoxy-3-quinolyl Ureas
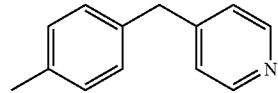
| Entry | R | mp (° C.) | HPLC (min.) | TLC $R_f$ | TLC Solvent System | Mass Spec. [Source] |
|---|---|---|---|---|---|---|
| 22 | 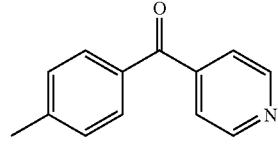 | | | 0.45 | 50% EtOAc/ 50% hexane | 375 (M + H) + (HPLC ES-MS) |
| 23 | 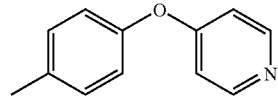 | | | 0.56 | 50% EtOAc/ 50% hexane | 385 (M + H) + (FAB) |
| 24 | 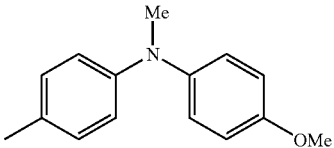 | | | 0.45 | 100% EtOAc | 399 (M + H) + (FAB) |
| 25 | | 207-208 | | 0.24 | 5% MeOH/ 95% CH2Cl2 | 387 (M + H) + (FAB) |
| 26 | | 126-130 | | | | |

TABLE 3-continued

2-Methoxy-3-quinolyl Ureas

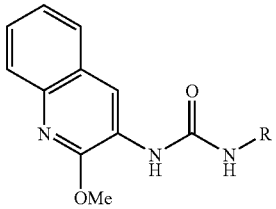

| Entry | R | mp (° C.) | HPLC (min.) | TLC $R_f$ | TLC Solvent System | Mass Spec. [Source] |
|---|---|---|---|---|---|---|
| 27 | (3-methylphenyl-S-4-pyridyl) | | | 0.39 | 50% acetone/ 50% CH2Cl2 | 403 (M + H) + (FAB) |

TABLE 4

3-Quinolyl Ureas

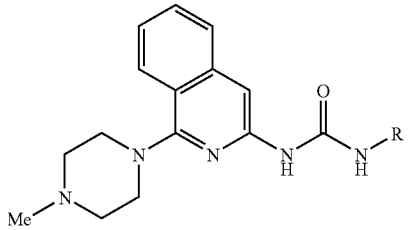

| Entry | R | mp (° C.) | HPLC (min.) | TLC $R_f$ | TLC Solvent System | Mass Spec. [Source] |
|---|---|---|---|---|---|---|
| 28 | (4-methylphenyl-O-4-pyridyl) | | | 0.20 | 30% MeOH/ 70% EtOAc | 455 (M + H) + (HPLC ES-MS) |

BIOLOGICAL EXAMPLES

In Vitro raf Kinase Assay

In an in vitro kinase assay, raf was incubated with MEK in 20 mM Tris-HCl, pH 8.2 containing 2 mM 2-mercaptoethanol and 100 mM NaCl. This protein solution (20 μL) was mixed with water (5 μL) or with compounds diluted with distilled water from 10 mM stock solutions of compounds dissolved in DMSO. The kinase reaction was initiated by adding 25 μL [λ-$^{33}$P]ATP (1000-3000 dpm/pmol) in 80 mM Tris-HCl, pH 7.5, 120 mM NaCl, 1.6 mM DTT, 16 mM MgCl$_2$. The reaction mixtures were incubated at 32° C., usually for 22 min. Incorporation of $^{33}$P into protein was assayed by harvesting the reaction onto phosphocellulose mats, washing away free counts with a 1% phosphoric acid solution and quantitating phosphorylation by liquid scintillation counting. For high throughput screening, 10 μM ATP and 0.4 μM MEK was used. In some experiments, the kinase reaction was stopped by adding an equal amount of Laemmli sample buffer. Samples were boiled 3 min and the proteins resolved by electrophoresis on 7.5% Laemmli gels. Gels were fixed, dried and exposed to an imaging plate (Fuji). Phosphorylation was analyzed using a Fujix Bio-Imaging Analyzer System.

All compounds exemplified displayed IC$_{50}$s of between 10 nM and 10 μM.

Cellular Assay

For in vitro growth assay, human tumor cell lines, including but not limited to HCT 116 and DLD-1, containing mutated K-ras genes were used in standard proliferation assays for anchorage dependent growth on plastic or anchorage independent growth in soft agar. Human tumor cell lines were obtained from ATCC (Rockville Md.) and maintained in RPMI with 10% heat inactivated fetal bovine serum and 200 mM glutamine. Cell culture media and additives were obtained from Gibco/BRL (Gaithersburg, Md.) except for fetal bovine serum (JRH Biosciences, Lenexa, Kans.). In a standard proliferation assay for anchorage dependent growth, 3×10$^3$ cells were seeded into 96-well tissue culture plates and allowed to attach overnight at 37° C. in a 5% CO$_2$ incubator. Compounds were titrated in media in dilution series and added to 96-well cell cultures. Cells were allowed to grow 5 days typically with a feeding of fresh compound containing media on day three. Proliferation was monitored by measuring metabolic activity with standard XTT colorimetric assay (Boehringer Mannheim) measured by standard ELISA plate reader at OD 490/560, or by measuring $^3$H-thymidine incorporation into DNA following an 8 h culture with 1 μCu $^3$H-thymidine, harvesting the cells onto glass fiber mats using a cell harvester and measuring $^3$H-thymidine incorporation by liquid scintillation counting.

For anchorage independent cell growth, cells were plated at $1\times10^3$ to $3\times10^3$ in 0.4% Seaplaque agarose in RPMI complete media, overlaying a bottom layer containing only 0.64% agar in RPMI complete media in 24-well tissue culture plates. Complete media plus dilution series of compounds were added to wells and incubated at 37° C. in a 5% $CO_2$ incubator for 10-14 days with repeated feedings of fresh media containing compound at 3-4 day intervals. Colony formation was monitored and total cell mass, average colony size and number of colonies were quantitated using image capture technology and image analysis software (Image Pro Plus, media Cybernetics).

These assays established that the compounds of formula I are active to inhibit raf kinase activity and to inhibit oncogenic cell growth.

In Vivo Assay

An in vivo assay of the inhibitory effect of the compounds on tumors (e.g., solid cancers) mediated by raf kinase can be performed as follows:

CDI nu/nu mice (6-8 weeks old) are injected subcutaneously into the flank at $1\times10^6$ cells with human colon adenocarcinoma cell line. The mice are dosed i.p., i.v. or p.o. at 10, 30, 100, or 300 mg/Kg beginning on approximately day 10, when tumor size is between 50-100 mg. Animals are dosed for 14 consecutive days once a day; tumor size was monitored with calipers twice a week.

The inhibitory effect of the compounds on raf kinase and therefore on tumors (e.g., solid cancers) mediated by raf kinase can further be demonstrated in vivo according to the technique of Monia et al. (*Nat. Med.* 1996, 2, 668-75).

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A compound of one of the following formulae

A-D-B     (I)

A'-D-B'     (II) and

A"-D-B"     (III)

or a pharmaceutically acceptable salt thereof, wherein
D is —NH—C(O)—NH—,
A is selected from the group consisting of substituted t-butylpyridyl groups, unsubstituted t-butylpyridyl groups, substituted (trifluoromethyl) pyridyl groups, unsubstituted (trifluoromethyl) pyridyl groups, substituted isopropylpyridyl groups, unsubstituted isopropylpyridyl groups, substituted (2-methyl-2-butyl) pyridyl groups, unsubstituted (2-methyl-2-butyl pyridyl) groups, substituted (3-methyl-3-pentyl) pyridyl groups, and unsubstituted (3-methyl-3-pentyl) pyridyl groups, substituted (3-ethyl-3-pentyl) pyridyl groups and unsubstituted (3-ethyl-3-pentyl) pyridyl groups, A' is a substituted isoquinolinyl group or unsubstituted isoquinolinyl group or an unsubstituted quinolinyl group,
A" is a substituted quinolinyl group,
B, B' and B" are each, independently, a substituted or unsubstituted bridged cyclic structure of up to 30 carbon atoms of the formula -L-(ML$^1$)$_q$ wherein L comprises a cyclic moiety having at least 5 members and is bound directly to D, L$^1$ comprises a cyclic moiety having at least 5 members, M is a bridging group selected from the group consisting of —O—, —S—, —N(R$^7$)—, —(CH$_2$)$_m$—, —C(O)—, —CH(OH)—, —(CH$_2$)$_m$O—, —(CH$_2$)$_m$S—, —(CH$_2$)$_m$N(R$^7$)—, —O(CH$_2$)$_m$, —CHX$^a$—, —CX$^a_2$—, —S—(CH$_2$)$_m$— and —N(R$^7$)(CH$_2$)$_m$—, where m=1-3, X$^a$ is halogen, and R$^7$ is as defined below,
q is an integer of from 1-3, and each cyclic structure of L and L$^1$ contains 0-4 members of the group consisting of nitrogen, oxygen and sulfur,
subject to the provisos that B is not

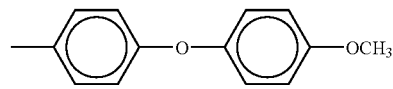

and B' is not

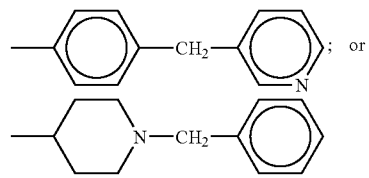

wherein the substituents for A" and the substituted isoquinolinyl groups of A' are selected from the group consisting of halogen, up to per-halo, and Wn, where n is 0-3 and each W is independently selected from the group consisting of $C_{1-10}$ alkyl, $C_{1-10}$ alkoxy, at least a five membered $C_{3-10}$ cycloalkyl having 0-3 heteroatoms, $C_{2-10}$ alkenyl, $C_{1-10}$ alkenoyl, substituted $C_{1-10}$ alkyl, substituted $C_{1-10}$ alkoxy, at least a five-membered substituted $C_{3-10}$ cycloalkyl having 0-3 heteroatoms selected from N, S and O; —CN, up to per halo substituted $C_6$-$C_{14}$ aryl, up to per halo substituted $C_7$-$C_{24}$ alkaryl, up to per halo substituted $C_7$-$C_4$ aralkyl, up to per halo substituted $C_3$-$C_{12}$ heteroaryl having at least 5 members and 1-3 heteratoms selected from 0, N and S, up to per halo substituted $C_4$-$C_{24}$ alkheteroaryl having at least 5 members and 1-3 heteroatoms selected from O, N and S, $C_6$-$C_{14}$ aryl, $C_1$-$C_{24}$ alkaryl, $C_1$-$C_{24}$ aralkyl, $C_3$-$C_{12}$ heteroaryl having at least 5 cyclic members and 1-3 heteroatoms selected from O, N and S, $C_4$-$C_{24}$ alkheteroaryl having at least 5 cyclic members and 1-3 heteroatoms selected from O, N and S; —CO$_2$R$^7$, —C(O)NR$^7$R$^{7'}$, —C(O)—R$^7$, —NO$_2$, —OR$^7$, —SR$^7$, —NR$^7$R$^{7'}$, —NR$^7$C(O)OR$^{7'}$, —NR$^7$C(O)R$^{7'}$, with each R$^7$ and R$^{7'}$ independently selected from hydrogen, $C_{1-10}$ alkyl, $C_{1-10}$ alkoxy, $C_{2-10}$ alkenyl, $C_{1-10}$ alkenoyl, up to per halosubstituted $C_{1-10}$ alkyl, up to per halosubstituted $C_{1-10}$ alkoxy, up to per halosubstituted $C_{2-10}$ alkenyl and up to per halosubstituted $C_{1-10}$ alkenoyl;

wherein the substitutents for the substituted t-butyl pyridyl groups substituted trifluoromethyl pyridyl groups, substituted isopropyl pyridyl groups, substituted 2-methyl-2-butyl pyridyl groups and substituted 3-methyl-3-pentyl pyridyl groups of A are selected from the group consisting of halogen, up to per-halo, and Zn, where n is 0-3 and each Z is independently selected from the group consisting of $C_{1-10}$ alkyl, $C_{1-10}$ alkoxy, $C_{2-10}$ alkenyl, $C_{1-10}$ alkenoyl, —CN, —$CO_2R^7$, —C(O)$NR^7R^{7'}$, —C(O)—$R^7$, —$NO_2$, —$OR^7$, —$SR^7$, —$NR^7R^{7'}$, —$NR^7C(O)OR^{7'}$, —$NR^7C(O)R^{7'}$, with each $R^7$ and $R^{7'}$ independently as defined above for W;

where B and B' are substituted, the substituents are selected from the group consisting of halogen, up to per-halo, and Jn, where n is 0-3 and each J is independently selected from the group consisting of —CN, —$CO_2R^7$, —C(O)$NR^7R^{7'}$, —C(O)—$R^7$, —$NO_2$, —$OR^7$, —$SR^7$, —$NR^7R^{7'}$, —$NR^7C(O)OR^{7'}$, —$NR^7C$ (O)$R^{7'}$, with each $R^7$ and $R^{7'}$ independently as defined above for W, $C_{1-10}$ alkyl, $C_{1-10}$ alkoxy, at least a five-membered $C_{3-10}$ cycloalkyl having 0-3 heteroatoms, $C_{2-10}$ alkenyl, $C_{1-10}$ alkenoyl, $C_{6-12}$ aryl, at least a five-membered $C_{3-12}$ hetaryl having 1-3 heteroatoms selected from N, S and O, $C_{7-24}$ aralkyl, $C_{7-24}$ alkaryl, substituted $C_{1-10}$ alkyl, substituted $C_{1-10}$ alkoxy, at least a five-membered substituted $C_{3-10}$ cycloalkyl having 0-3 heteroatoms selected from N, S and O, substituted $C_6$-$C_{14}$ aryl, at least a five-membered substituted $C_{3-12}$ hetaryl having 1-3 heteroatoms selected from N, S and O, substituted $C_{7-24}$ alkaryl and substituted $C_7$-$C_{24}$ aralkyl, where B" is substituted, the substituents are selected from the group consisting of halogen, —CN, —C(O)$NR^7R^{7'}$, —C(O)—$R^7$, —$NO_2$, —$OR^7$, —$SR^7$, —$NR^7R^{7'}$, —$NR^7C(O)OR^{7'}$, —$NR^7C(O)R^{7'}$, with each $R^7$ and $R^{7'}$ independently as defined above for W, $C_{1-10}$ alkyl, at least a five-membered $C_{3-10}$ cycloalkyl having 0-3 heteroatoms, $C_{2-10}$ alkenyl, $C_{1-10}$ alkenoyl, $C_{6-12}$ aryl, at least a five-membered $C_{3-12}$ hetaryl having 1-3 heteroatoms selected from N, S and O, $C_{7-24}$ aralkyl, substituted $C_{1-10}$ alkyl, substituted $C_{1-10}$ alkoxy, at least a five-membered substituted $C_{3-10}$ cycloalkyl having 0-3 heteroatoms selected from N, S and O, substituted $C_6$-$C_{14}$ aryl, at least a five-membered substituted $C_{3-12}$ hetaryl having 1-3 heteroatoms selected from N, S and O, substituted $C_{7-24}$ alkaryl and substituted $C_7$-$C_{24}$ aralkyl, subject to the proviso that where B, B' or B" is -L($ML^1$)$_q$, $L^1$ is not substituted by the substituents —C(O)$R^a$, —C($NR^a$)$R^b$, —C(O)$NR^aR^b$ and —$SO_2R^a$ wherein each $R^a$ and $R^b$ are independently hydrogen or a carbon based moiety of up to 24 carbon atoms, optionally containing heteroatoms selected from N, S and O, where J is a substituted group, it is substituted by halogen, up to per halo, or by one or more substituents independently selected from the group consisting of —CN, —$CO_2R^7$, —$OR^7$, —$SR^7$, —$NR^7R^{7'}$, —$NO_2$, —$NR^7C$ (O)$R^{7'}$ and —$NR^7C(O)OR^{7'}$; with each $R^7$ and $R^{7'}$ independently as defined above for W.

2. A compound as in claim 1, wherein:
$R^a$ and $R^b$ are, independently, $C_{1-10}$ alkyl, $C_{1-10}$ alkoxy, $C_{3-10}$ cycloalkyl having 0-3 heteroatoms, $C_{2-10}$ alkenyl, $C_{1-10}$ alkenoyl, $C_{6-12}$ aryl, $C_{3-12}$ hetaryl having 1-3 heteroatoms selected from N, S and O, $C_{7-24}$ aralkyl, $C_{7-24}$ alkaryl, substituted $C_{1-10}$ alkyl, substituted $C_{1-10}$ alkoxy, substituted $C_{3-10}$ cycloalkyl having 0-3 heteroatoms selected from N, S and O, substituted $C_6$-$C_{14}$ aryl, substituted $C_{3-12}$ hetaryl having 1-3 heteroatoms selected from N, S and O, substituted $C_{7-24}$ alkaryl or substituted $C_7$-$C_{24}$ aralkyl, where $R^a$ is a substituted group, it is substituted by halogen up to per halo.

3. A compound of claim 1, wherein L in the formula -L-($ML^1$)$_q$ for B, B' and B" is a substituted 6 member cyclic aryl moiety, a substituted 5-6 member cyclic hetaryl moiety, an unsubstituted 6 member cyclic aryl moiety, or an unsubstituted 5-6 member cyclic hetaryl moiety, and $L^1$ in the formula -L-($ML^1$)$_q$ of B, B' and B" is a substituted aryl moiety having at least six cyclic members, an unsubstituted aryl moiety having at least six cyclic members, a substituted hetaryl moiety having at least 5 cyclic members or an unsubstituted hetaryl moiety having at least 5 cyclic members, said hetaryl moieties having 1 to 4 members selected from the group of hetaryl atoms consisting of nitrogen, oxygen and sulfur with the balance of the hetaryl moiety being carbon.

4. A compound of claim 1, wherein L and $L^1$ in formula -L($ML^1$)$_q$ for B, B' and B" are each independently selected from the group consisting of thiophene, phenyl, substituted phenyl, pyridinyl, substituted pyridinyl, pyrimidinyl substituted pyrimidinyl, napthyl, substituted napthyl, quinolinyl, substituted quinolinyl, isoquinodiyl and substituted isoquinodiyl.

5. A compound of claim 4, wherein B is a substituted group, it is substituted by —CN, halogen, $C_{1-10}$ alkyl, $C_{1-10}$ alkoxy, —OH, up to per halo substituted $C_{1-10}$ alkyl, up to per halo substituted $C_{1-10}$ alkoxy —O($R^7$), —$SR^7$, —$NR^7R^7$ or —$NO_2$, wherein each $R^7$ is independently selected from hydrogen, $C_{1-10}$ alkyl, $C_{1-10}$ alkoxy, $C_{2-10}$ alkenyl, $C_{1-10}$ alkenoyl, up to per halosubstituted $C_{1-10}$ alkyl, up to per halosubstituted $C_{1-10}$ alkoxy, up to per halosubstituted $C_{2-10}$ alkenyl and up to per halosubstituted $C_{1-10}$ alkenoyl.

6. A compound of claim 4, wherein M in the formula -L-($ML^1$) for B, B' and B" is —O—, —$CH_2$—, —S—, —NH—, —C(O)—, —O—$CH_2$— and —$CH_2$—O—.

7. A compound of one of the following formulae A-D-B, A'-D-B'and A"-D-B" or a pharmaceutically acceptable salt thereof wherein D is —NH—C(O)—NH—

A is selected from the group consisting of substituted t-butylpyridyl groups, unsubstituted t-butylpyridyl groups, substituted (trifluoromethyl) pyridyl groups, unsubstituted (triftuoromethyl) pyridyl groups, substituted isopropylpyridyl groups, unsubstituted isopropylpyridyl groups, substituted (2-methyl-2-butyl) pyridyl groups, unsubstituted (2-methyl-2-butyl) pyridyl groups, substituted (3-methyl-3-pentyl) pyridyl groups, unsubstituted (3-methyl-3-pentyl) pyridyl groups, substituted (3-ethyl-3-pentyl) pyridyl groups, and unsubstituted (3-ethyl-3-pentyl) pyridyl groups, A' is a substituted isoquinolinyl group or unsubstituted isoquinolinyl group or an unsubstituted quinolinyl group, A" is a substituted quinolinyl group, B, B' and B" are each independently of the formula -L-($ML^1$)$_q$, wherein L is phenyl or substituted phenyl and $L^1$ is phenyl, substituted phenyl, pyridinyl or substituted pyridinyl, q is an integer of from 1-2 and M is selected from the group consisting of —O—, —S—, —N($R^7$)—, —($CH_2$)$_m$—, —C(O)—, —CH(OH)—, ($CH_2$)$_m$O—, —($CH_2$)$_m$S—, —($CH_2$)$_m$N($R^7$)—, —O($CH_2$)$_m$; —$CHX^a$—, —$CX^a_2$—, —S—($CH_2$)— and —N($R^7$)($CH_2$)$_m$—, where m=1-3, $X^a$ is halogen, and $R^7$ is as defined below;

subject to the provisos that B' is not

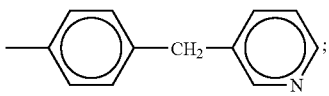

B is not

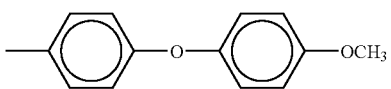

wherein the substituents for the substituted t-butyl pyridyl groups, substituted trifluoromethyl pyridyl groups, substituted isopropyl pyridyl groups, substituted 2-methylbutyl pyridyl groups and 3-methylpentyl pyridyl groups, of A are selected from the group consisting of halogen, up to per-halo, and Zn, where n is 0-3 and each Z is independently selected from the group consisting of $C_{1-10}$ alkyl, $C_{1-10}$ alkoxy, $C_{2-10}$ alkenyl, $C_{1-10}$ alkenoyl, —CN, —$CO_2R^7$, —$C(O)NR^7R^{7'}$, —C(O)—$R^7$, —$NO_2$, —$OR^7$, —$SR^7$, —$NR^7R^{7'}$, —$NR^7C(O)OR^{7'}$, —$NR^7C(O)R^{7'}$, with each $R^7$ and $R^{7'}$ independently selected from hydrogen, $C_{1-10}$ alkyl, $C_{1-10}$ alkoxy, $C_{2-10}$ alkenyl, $C_{1-10}$ alkenoyl, up to per halosubstituted $C_{1-10}$ alkyl, up to per halosubstituted $C_{1-10}$ alkoxy, up to per halosubstituted $C_{2-10}$ alkenyl and up to per halosubstituted $C_{1-10}$ alkenoyl;

wherein the substituents for A" and the substituted isoquinolinyl groups of A' are selected from the group consisting of halogen, up to per-halo, and Wn, where n is 0-3 and each W is independently selected from the group consisting of $C_{1-10}$ alkyl, $C_{1-10}$ alkoxy, $C_{2-10}$ alkenyl, $C_{1-10}$ alkenoyl, substituted $C_{1-10}$ alkyl, substituted $C_{1-10}$ alkoxy, —CN, —$CO_2R^7$, —$C(O)NR^7R^{7'}$, —C(O)—$R^7$, —$NO_2$, —$OR^7$, —$SR^7$, —$NR^7R^{7'}$, —$NR^7C(O)OR^{7'}$, —$NR^7C(O)R^{7'}$, with each $R^7$ and $R^{7'}$ independently selected from hydrogen, $C_{1-10}$ alkyl, $C_{1-10}$ alkoxy, $C_{2-10}$ alkenyl, $C_{1-10}$ alkenoyl, up to per halosubstituted $C_{1-10}$ alkyl, up to per halosubstituted $C_{1-10}$ alkoxy, up to per halosubstituted $C_{2-10}$ alkenyl and up to per halosubstituted $C_{1-10}$ alkenoyl;

wherein B and B' are substituted, the substituents are selected from the group consisting of halogen, up to per-halo, and Jn, where n is 0-3 and each J is independently selected from the group consisting of —CN, —$CO_2R^7$, —$C(O)NR^7R^{7'}$, —C(O)—$R^7$, —$NO_2$, —$OR^7$, —$SR^7$, —$NR^7R^{7'}$, —$NR^7C(O)OR^{7'}$, —$NR^7C(O)R^{7'}$, with each $R^7$ and $R^{7'}$ independently as defined above for W, $C_{1-10}$ alkyl, $C_{1-10}$ alkoxy, $C_{2-10}$ alkenyl, $C_{1-10}$ alkenoyl, substituted $C_{1-10}$ alkyl, and substituted $C_{1-10}$ alkoxy, subject to the proviso that where B, B' or B" is -L(ML$^1$)$_q$, L$^1$ is not substituted by the substituents —C(O)R$^a$, —C(NR$^a$)R$^b$, —C(O)NR$^a$R$^b$ and —SO$_2$R$^a$ wherein R$^a$ and R$^b$ are each independently, hydrogen or a carbon based moiety of up to 24 carbon atoms, optionally containing heteroatoms selected from N, S and O;

wherein B" is substituted, the substituents are selected from the group consisting of halogen, —CN, —C(O)NR$^7$R$^{7'}$, —NO$_2$, —OR$^7$, —SR$^7$, —NR$^7$R$^{7'}$, —NRC(O)OR$^{7'}$, —NR$^7$C(O)R$^{7'}$, with each R$^7$ and R$^{7'}$ independently as defined above for W, $C_{1-10}$ alkyl, $C_{2-10}$ alkenyl, $C_{1-10}$ alkenoyl, substituted $C_{1-10}$ alkyl, and substituted $C_{1-10}$ alkoxy, subject to the proviso that where B, B' or B" is -L(ML$^1$)$_q$, L$^1$ is not substituted by the substituents —C(O)R$^a$, —C(NR$^a$)R$^b$, —C(O)NR$^a$R$^b$ and —SO$_2$R$^a$ wherein R$^a$ and R$^b$ are each independently, hydrogen or a carbon based moiety of up to 24 carbon atoms, optionally containing heteroatoms selected from N, S and O.

8. A compound of claim 7, wherein the substituents for B, B' and B" are independently selected from the group consisting of —CN, halogen, $C_{1-10}$ alkyl, $C_{1-10}$ alkoxy, —OH, up to per halo substituted $C_{1-10}$ alkyl, and up to per halo substituted $C_{1-10}$ alkoxy.

9. A compound of claim 1, wherein the substituted pyridyl groups of A, the substituted isoquinolinyls of A' and the substituted quinolinyls of A" have 1-3 substituents selected from the group consisting of $C_{1-10}$ alkyl, up to per halo substituted $C_{1-10}$ alkyl, —CN, —OH, halogen, $C_{1-10}$ alkoxy, up to per halo substituted $C_{1-10}$ alkoxy and at least five-membered $C_3$-$C_{10}$ heterocyclic moieties comprising 1 to 2 heteroatoms selected from the group of consisting of nitrogen, oxygen and sulfur.

10. A compound of claim 7, wherein the substituted pyridyl groups of A, the substituted isoquinolinyls of A' and the substituted quinolinyls of A" have 1-3 substituents selected from the group consisting of $C_{1-10}$ alkyl, up to per halo substituted $C_{1-10}$ alkyl, —CN, —OH, halogen, $C_{1-10}$ alkoxy and up to per halo substituted $C_{1-10}$ alkoxy.

11. A compound of claim 1, wherein L and L$^1$ are independently phenyl, substituted phenyl, pyridinyl, substituted pyridinyl, pyrimidinyl or substituted pyrimidinyl.

12. A compound of claim 1, wherein L$^1$ is substituted 1 to 3 times by one or more substituents selected from the group consisting of $C_1$-$C_{10}$ alkyl, up to per halo substituted $C_1$-$C_{10}$ alkyl, —CN, —OH, halogen, $C_1$-$C_{10}$ alkoxy and up to per halo substituted $C_1$-$C_{10}$ alkoxy.

13. A compound of claim 7 wherein L$^1$ is substituted 1 to 3 times by one or more substituents selected from the group consisting of $C_1$-$C_{10}$ alkyl, up to per halo substituted $C_1C_{10}$ alkyl, —CN, —OH, halogen, $C_1$-$C_{10}$ alkoxy and up to per halo substituted $C_1$-$C_{10}$ alkoxy.

14. A compound of claim 1 wherein each substituent J is independently selected from the group consisting of $C_1$-$C_{10}$ alkyl, up to per halo substituted $C_1$-$C_{10}$ alkyl, —CN, —OH, halogen, $C_1$-$C_{10}$ alkoxy, up to per halo substituted $C_1$-$C_{10}$ alkoxy, —CN, —$CO_2R^7$, —$C(O)NR^7R^{7'}$, —C(O)—$R^7$, —$NO_2$, —$OR^7$, —$SR^7$, —$NR^7R^{7'}$, —$NR^7C(O)OR^{7'}$ and —$NR^7C(O)R^{7'}$, where $R^7$ and $R^{7'}$ are each, independently, as defined for W in claim 1, M is —O—, —S—, —N(R$^7$)—, —(CH$_2$)$_m$—, —C(O)—, —CH(OH)—, —(CH$_2$)$_m$O— and —O(CH$_2$)$_m$—, where m=1-3; and L$^1$ is phenyl, pyridinyl, pyrimidinyl, substituted phenyl, substituted pyridinyl and substituted pyrimidinyl, with substituents selected from the group consisting of —CN; —OH; halogen up to per-halo; $C_1$-$C_{10}$ alkoxy and halosubstituted $C_1$-$C_{10}$ alkoxy, up to per-halo.

15. A compound of claim 1 which is a pharmaceutically acceptable salt of a compound of formula I selected from the group consisting of a) basic salts of organic acids and inorganic acids selected from the group consisting of hydrochloric acid, hydrobromic acid, sulfuric acid, phosphoric acid, methanesulfonic acid, trifluorosulfonic acid, benzenesulfonic acid, p-toluene sulfonic acid (tosylate salt), 1-napthalene sulfonic acid, 2-napthalene sulfonic acid, acetic acid, trifluoroacetic acid, malic acid, tartaric acid, citric acid, lactic acid, oxalic acid, succinic acid, fumaric acid, maleic acid, benzoic acid, salicylic acid, phenylacetic acid, and mandelic acid; and b) acid salts of organic and inorganic bases containing cations selected from the group consisting of alkaline cations, alkaline earth cations, the ammonium cation, aliphatic substituted ammonium cations and aromatic substituted ammonium cations.

16. A compound of claim 7 which is a pharmaceutically acceptable salt of a compound of formula I selected from the group consisting of a) basic salts of organic acids and inorganic acids selected from the group consisting of hydrochloric acid, hydrobromic acid, sulphuric acid, phosphoric acid, methanesulphonic acid, trifluorosulphonic acid, benzenesulfonic acid, p-toluene sulfonic acid (tosylate salt), 1-napthalene sulfonic acid, 2-napthalene sulfonic acid, acetic acid, trifluoroacetic acid, malic acid, tartaric acid, citric acid, lactic acid, oxalic acid, succinic acid, fumaric acid, maleic acid, benzoic acid, salicylic acid, phenylacetic acid, and mandelic acid; and b) acid salts of organic and inorganic bases containing cations selected from the group consisting of alkaline cations, alkaline earth cations, the ammonium cation, aliphatic substituted ammonium cations and aromatic substituted ammonium cations.

17. A pharmaceutical composition comprising a compound of claim 1 and a physiologically acceptable carrier.

18. A pharmaceutical composition comprising a compound of claim 7 and a physiologically acceptable carrier.

19. A compound selected from the group consisting of:
N-(4-tert-butylpyridinyl)-N'-(4-(4-pyridinylmethyl)phenyl) urea or a pharmaceutically acceptable salt thereof;
N-(4-tert-butylpyridinyl)-N'-(4-phenoxyphenyl) urea or a pharmaceutically acceptable salt thereof;
N-(4-tert-butylpyridinyl)-N'-(4-(4-methylphenoxy)phenyl) or a pharmaceutically acceptable salt thereof;
N-(4-tert-butylpyridinyl)-N'-(4-(4-chlorophenoxy)phenyl) urea or a pharmaceutically acceptable salt thereof;
N-(4-tert-butylpyridinyl)-N'-(4-(4-pyridinyloxy)phenyl) urea or a pharmaceutically acceptable salt thereof;
N-(4-tert-butylpyridinyl)-N'-(4-(4-pyridinylthio)phenyl) urea or a pharmaceutically acceptable salt thereof
N-(4-tert-butylpyridinyl)-N'-(3-(4-pyridinylthio)phenyl) urea or a pharmaceutically acceptable salt thereof;
N-(3-isoquinolinyl)-N'-(4-(4-pyridinyloxy)phenyl) urea or a pharmaceutically acceptable salt thereof;
N,N'-(bis(3-(2-methoxyquinolinyl)) urea) or a pharmaceutically acceptable salt thereof;
N-(3-(2-methoxyquinolinyl)-N'-(4-(4-pyridinylmethyl) phenyl)) urea or a pharmaceutically acceptable salt thereof;
N-(3-(2-methoxyquinolinyl)-N'-(4-(4-pyridinylcarbonyl) phenyl)) urea or a pharmaceutically acceptable salt thereof;
N-(3-(2-methoxyquinolinyl)-N'-(4-(4-pyridinyloxy)phenyl)) urea or a pharmaceutically acceptable salt thereof;
N-(3-(2-methoxyquinolinyl)-N'-(4-((4-methoxyphenyl) methylamino)phenyl)) urea or a pharmaceutically acceptable salt thereof;
N-(3-(2-methoxyquinolinyl)-N'-(3-(4-pyridinylthio)phenyl)) urea or a pharmaceutically acceptable salt thereof; and
N-(1-(4-methylpiperazinyl)-3-isoquinolinyl)-N'(4-(4-pyridinyloxy)phenyl) urea or a pharmaceutically acceptable salt thereof.

20. A pharmaceutical composition comprising a compound of claim 19 and a physiologically acceptable carrier.

21. A compound of claim 1 of one of the following formulae

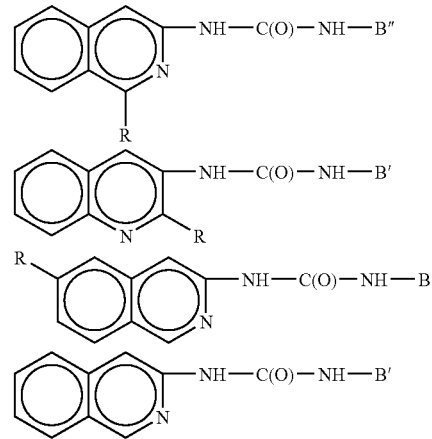

wherein B, B' and B" are as defined in claim 1 and R is selected from the group consisting of halogen, $C_{1-10}$ alkyl, $C_{1-10}$ alkoxy, $C_{2-10}$ alkenyl, $C_{1-10}$ alkenoyl, —CN, —$CO_2R^7$, —C(O)$NR^7R^{7'}$, —C(O)—$R^7$, —$NO_2$, —$OR^7$, —$SR^7$, —$NR^7R^{7'}$, —$NR^7C(O)OR^{7'}$, —$NR^7C(O)R^{7'}$, with each $R^7$ and $R^{7'}$ are independently selected from hydrogen, $C_{1-10}$ alkyl, $C_{1-10}$ alkoxy, $C_{2-10}$ alkenyl, $C_{1-10}$ alkenoyl, up to per halosubstituted $C_{1-10}$ alkyl, up to per halosubstituted $C_{1-10}$ alkoxy, up to per halosubstituted $C_{2-10}$ alkenyl and up to per halosubstituted $C_{1-10}$ alkenoyl.

22. A compound of claim 1:
wherein L is a cyclic moiety having an atom of the cyclic member bound directly to D and another atom of the cyclic member bound directly to -M-$L^1$ which is separated from the cyclic member bound directly to D by at least one other atom of the cyclic member and L is selected from the group consisting of:

(i) phenyl, optionally substituted with 1-3 substituents independently selected from the group consisting of $C_1$-$C_5$, linear or branched alkyl, $C_1$-$C_5$ linear or branched haloalkyl up to perhalo, $C_1$-$C_3$ alkoxy, $C_1$-$C_3$ haloalkoxy up to per haloalkoxy, hydroxy, amino, $C_1$-$C_3$ alkylamino, $C_1$-$C_6$ dialkylamino, halogen, cyano, and nitro;

(ii) 5 membered monocyclic heteroaryl groups, having 1-2 heteroatoms independently selected from the group consisting of O, N and S, optionally substituted with 1-3 substituents independently selected from the group consisting of $C_1$-$C_5$ linear or branched alkyl, $C_1$-$C_5$ linear or branched haloalkyl up to perhalo, $C_1$-$C_3$ alkoxy, $C_1$-$C_3$ haloalkoxy up to per haloalkoxy, hydroxy, amino, $C_1$-$C_3$ alkylamino, $C_1$-$C_6$ dialkylamino, halogen, cyano, and nitro; and (iii) 6 membered monocyclic heteroaryl groups, having 1-4 heteroatoms independently selected from the group consisting of O, N and S, optionally substituted with 1-3 substituents independently selected from the group consisting of $C_1$-$C_5$ linear or branched alkyl, $C_1$-$C_5$ linear or branched haloalkyl up to perhalo, $C_1$-$C_3$ alkoxy, $C_1$-$C_3$ haloalkoxy up to per haloalkoxy, hydroxy, amino, $C_1$-$C_3$ alkylamino, $C_1$-$C_6$ dialkylamino, halogen, cyano, and nitro;

$L^1$ comprises a substituted cyclic moiety selected from the group consisting of:
  (i) phenyl, optionally substituted with 1-3 substituents independently selected from the group consisting of $R^7$, $OR^7$, $NR^7R^{7'}$, $NR^7C(O)R^{7'}$, $NR^7C(O)OR^{7'}$, halogen, cyano and nitro;
  (ii) naphthyl, optionally substituted with 1-3 substituents independently selected from the group consisting of $R^7$, $OR^7$, $NR^7R^{7'}$, $NR^7C(O)R^{7'}$, $NR^7C(O)OR^{7'}$, halogen, cyano and nitro;
  (iii) 5 and 6 membered monocyclic heteroaryl groups, having 1-4 heteroatoms independently selected from the group consisting of O, N and S, optionally substituted with 1-3 substituents independently selected from the group consisting of $R^7$, $OR^7$, $NR^7R^{7'}$, $NR^7C(O)R^{7'}$, $NR^7C(O)OR^{7'}$, halogen, cyano and nitro;
  (iv) 8 to 10 membered bicyclic heteroaryl groups, having 1-4 heteroatoms independently selected from the group consisting of O, N and S, optionally substituted with 1-3 substituents independently selected from the group consisting of $R^7$, $OR^7$, $NR^7R^{7'}$, $NR^7C(O)R^{7'}$, $NR^7C(O)OR^{7'}$, halogen, cyano and nitro;

M is selected from the group consisting of
  —$(CH_2)_m$—O—$(CH_2)_l$—,
  —$(CH_2)_m$—S—$(CH_2)_l$—,
  —$(CH_2)_m$—$N(R^7)$—$(CH_2)_l$—,
  —$(CH_2)_m$—$(CH_2)_l$—,
  —$(CH_2)_m$—C(O)—$(CH_2)_l$—,
  —$(CH_2)_m$—C(OH)—$(CH_2)_l$—,
  —$(CH_2)_m$—$CHX^a$—$(CH_2)_l$—,
  —$(CH_2)_m$—$CX^a_2$—$(CH_2)_l$—,
  —$(CH_2)_m$—$N(R^7)C(O)$—$(CH_2)_l$—, and
  —$(CH_2)_m$—$C(O)N(R^7)$—$(CH_2)_l$—, where m and l are each independently integers of from 1-3, $X^a$ is halogen; and each $R^7$ and $R^{7'}$ is, independently,
  (a) hydrogen,
  (b) $C_1$-$C_6$ linear, branched, or cyclic alkyl, optionally substituted with 1-3 substituents independently selected from the group consisting of $C_1$-$C_5$ linear or branched alkyl, up to perhalo substituted $C_1$-$C_5$ linear or branched alkyl, $C_1$-$C_3$ alkoxy and hydroxy;
  (c) $C_1$-$C_6$ alkoxy, optionally substituted with 1-3 substituents independently selected from the group consisting of $C_1$-$C_5$ linear or branched alkyl, up to perhalo substituted $C_1C_5$ linear or branched alkyl, $C_1$-$C_3$ alkoxy, hydroxy and halogen;
  (d) phenyl, optionally substituted with 1-3 substituents independently selected from the group consisting of $C_1$-$C_5$ linear or branched alkyl, up to perhalo substituted $C_1$-$C_5$ linear or branched alkyl, $C_1$-$C_3$ alkoxy, hydroxy and halogen,
  (e) 5-6 membered monocyclic heteroaryl having 1-4 heteroatoms selected from the group consisting of O, N and S or 8-10 membered bicyclic heteroaryl having 1-6 heteroatoms selected from the group consisting of O, N and S, optionally substituted with 1-3 substituents independently selected from the group consisting of $C_1$-$C_5$ linear or branched alkyl, up to perhalo substituted $C_1$-$C_5$ linear or branched alkyl, $C_1$-$C_3$ alkoxy, hydroxy and halogen,
  (f) $C_1$-$C_3$ alkyl-phenyl, optionally substituted with 1-3 substituents independently selected from the group consisting of $C_1$-$C_5$ linear or branched alkyl, up to perhalo substituted $C_1$-$C_5$ linear or branched alkyl, $C_1$-$C_3$ alkoxy, hydroxy and halogen; and
  (g) up to per-halo substituted $C_1$-$C_5$ linear, branched or cyclic alkyl, and where not per-halo substituted, optionally substituted with 1-3 substituents independently selected from the group consisting of $C_1$-$C_5$ linear or branched alkyl, up to perhalo substituted $C_1$-$C_5$ liner or branched alkyl, $C_1$-$C_3$ alkoxy and hydroxy.

23. A compound as in claim 22 wherein M is one or more bridging groups selected from the group consisting of —O—, —S—, —$N(R^7)$—, —C(O)—, —CH(OH)—, —$(CH_2)O$—, —$(CH_2)S$—, —$(CH_2)N(R^7)$—, —$O(CH_2)$—, —CHF—, —$CF_2$—, —S—$(CH_2)$— and —$N(R^7)(CH_2)$—, —$C(O)CH_2$, —$CH_2OC(O)$—, —$C(O)OCH_2$, —$C(O)N(R^7)CH_2$—, —$N(R^7)C(O)CH_2$—, —$N(R^7)C(O)OCH_2$—, where $R^7$ is as defined in claim 1.

24. A compound of claim 22, wherein L is
  (i) phenyl, optionally substituted with 1-3 substituents independently selected from the group consisting of $R^7OR^7$, $NR^7R^{7'}$, $C(O)NR^7R^{7'}$, $NR^7C(O)R^{7'}$, $NR^7C(O)OR^{7'}$, halogen, cyano and nitro; or
  (ii) pyridyl, optionally substituted with 1-3 substituents independently selected from the group consisting of $R^1$, $OR^1$, $NR^1R^2$, $C(O)R^1$, $C(O)OR^1$, $C(O)NR^1R^2$, $NR^1C(O)R^2$, $NR^1C(O)OR^2$, halogen, cyano, and nitro; or
  (ii) pyrimidinyl, optionally substituted with 1-3 substituents independently selected from the group consisting of $R^7$, $OR^7$, $NR^7R^{7'}$, $C(O)R^7$, $C(O)OR^7$, $C(O)NR^7R^{7'}$, $NR^7C(O)R^{7'}$, $NR^7C(O)OR^{7'}$, halogen, cyano and nitro.

25. A compound of claim 22, wherein $L^1$ is phenyl, pyridinyl or pyrimidinyl.

26. A compound of claim 24, wherein $L^1$ is phenyl, pyridinyl or pyrimidinyl.

27. A compound of claim 1:
wherein L is a cyclic moiety having an atom of the cyclic member bound directly to D and another atom of the cyclic member bound directly to -M-$L^1$ which is separated from the cyclic member bound directly to D by at least one other atom of the cyclic member and
L is
  (i) phenyl, optionally substituted with 1-3 substituents independently selected from the group consisting of $C_1$-$C_5$ linear or branched alkyl, $C_1$-$C_5$ linear or branched haloalkyl up to perhalo, $C_1$-$C_3$ alkoxy, $C_1$-$C_3$ haloalkoxy up to per haloalkoxy, hydroxy, amino, $C_1$-$C_3$ alkylamino, $C_1$-$C_6$ dialkylamino, halogen, cyano, and nitro; or
  (ii) pyridyl optionally substituted with 1-3 substituents independently selected from the group consisting of $C_1$-$C_5$ linear or branched alkyl, $C_1$-$C_5$ linear or branched haloalkyl up to perhalo, $C_1$-$C_3$ alkoxy, $C_1$-$C_3$ haloalkoxy up to per haloalkoxy, hydroxy, amino, $C_1$-$C_3$ alkylamino, $C_1$-$C_6$ dialkylamino, halogen, cyano, and nitro;

$L^1$ comprises a substituted cyclic moiety selected from the group consisting of:
  (i) phenyl, optionally substituted with 1-3 substituents independently selected from the group consisting of $R^7$, $OR^7$, $NR^7R^{7'}$, $NR^7C(O)R^{7'}$, $NR^7C(O)OR^{7'}$, halogen, cyano and nitro;
  (ii) naphthyl, optionally substituted with 1-3 substituents independently selected from the group consisting of $R^7$, $OR^7$, $NR^7R^{7'}$, $NR^7C(O)R^{7'}$, $NR^7C(O)OR^{7'}$, halogen, cyano and nitro;

(iii) pyridyl, optionally substituted with 1-3 substituents independently selected from the group consisting of $R^7$, $OR^7$, $NR^7R^{7'}$, $NR^7C(O)R^{7'}$, $NR^7C(O)OR^{7'}$, halogen, cyano and nitro;
(iv) pyrimidinyl, optionally substituted with 1-3 substituents independently selected from the group consisting of $R^7$, $OR^7$, $NR^7R^{7'}$, $NR^7C(O)R^{7'}$, $NR^7C(O)OR^{7'}$, halogen, cyano and nitro;
(v) quinolinyl optionally substituted with 1-3 substituents independently selected from the group consisting of $R^7$, $OR^7$, $NR^7R^{7'}$, $NR^7C(O)R^{7'}$, $NR^7C(O)OR^{7'}$, halogen, cyano and nitro;
(vi) isoquinolinyl optionally substituted with 1-3 substituents independently selected from the group consisting of $R^7$, $OR^7$, $NR^7R^{7'}$, $NR^7C(O)R^{7'}$, $NR^7C(O)OR^{7'}$, halogen, cyano and nitro;

M is selected from the group consisting of
—$(CH_2)_m$—O—$(CH_2)_l$—,
—$(CH_2)_m$—S—$(CH_2)_l$—,
—$(CH_2)_m$—$N(R^7)$—$(CH_2)_l$—,
—$(CH_2)_m$—$(CH_2)_l$—,
—$(CH_2)_m$—C(O)—$(CH_2)_l$—,
—$(CH_2)_m$—C(OH)—$(CH_2)_l$—,
—$(CH_2)_m$—$CHX^a$—$(CH_2)_l$—,
—$(CH_2)_m$—$CX^a_2$—$(CH_2)_l$—,
—$(CH_2)_m$—$N(R^7)C(O)$—$(CH_2)_l$—, and
—$(CH_2)_m$—$C(O)N(R^7)$—$(CH_2)_l$—, where m and l are each independently integers of from 1-3, $X^a$ is halogen; and each $R^7$ and $R^{7'}$ is independently
(a) hydrogen,
(b) $C_1$-$C_6$ linear, branched, or cyclic alkyl, optionally substituted with 1-3 substituents independently selected from the group consisting of $C_1$-$C_5$ linear or branched alkyl, up to perhalo substituted $C_1$-$C_5$ linear or branched alkyl, $C_1$-$C_3$ alkoxy and hydroxy;
(c) $C_1$-$C_6$ alkoxy, optionally substituted with 1-3 substituents independently selected from the group consisting of $C_1$-$C_5$ linear or branched alkyl, up to perhalo substituted $C_1$-$C_5$ linear or branched alkyl, $C_1$-$C_3$ alkoxy, hydroxy and halogen;
(d) phenyl, optionally substituted with 1-3 substituents independently selected from the group consisting of $C_1$-$C_5$ linear or branched alkyl, up to perhalo substituted $C_1$-$C_5$ linear or branched alkyl, $C_1$-$C_3$ alkoxy, hydroxy and halogen,
(e) 5-6 membered monocyclic heteroaryl having 1-4 heteroatoms selected from the group consisting of O, N and S or 8-10 membered bicyclic heteroaryl having 1-6 heteroatoms selected from the group consisting of O, N and S, optionally substituted with 1-3 substituents independently selected from the group consisting of $C_1$-$C_5$ linear or branched alkyl, up to perhalo substituted $C_1$-$C_5$ linear or branched alkyl, $C_1$-$C_3$ alkoxy, hydroxy and halogen,
(f) $C_1$-$C_3$ alkyl-phenyl, optionally substituted with 1-3 substituents independently selected from the group consisting of $C_1$-$C_5$ linear or branched alkyl, up to perhalo substituted $C_1$-$C_5$ linear or branched alkyl, $C_1$-$C_3$ alkoxy, hydroxy and halogen; and
(g) up to per-halo substituted $C_1$-$C_5$ linear, branched or cyclic alkyl, and where not per-halo substituted, optionally substituted with 1-3 substituents independently selected from the group consisting of $C_1$-$C_5$ linear or branched alkyl, up to perhalo substituted $C_1$-$C_5$ linear or branched alkyl, $C_1$-$C_3$ alkoxy and hydroxy.

28. A compound of claim 1:
where L is
(i) phenyl, optionally substituted with 1-3 substituents independently selected from the group consisting of $C_1$-$C_5$ linear or branched alkyl, $C_1$-$C_5$ linear or branched haloalkyl, $C_1$-$C_3$ alkoxy, hydroxy, amino, $C_1$-$C_3$ alkylamino, $C_1$-$C_6$ dialkylamino, halogen, cyano, and nitro; or
(ii) pyridyl, optionally substituted with 1-3 substituents independently selected from the group consisting of $C_1$-$C_5$ linear or branched alkyl, $C_1$-$C_5$ linear or branched haloalkyl, $C_1$-$C_3$ alkoxy, hydroxy, amino, $C_1$-$C_3$ alkylamino, $C_1$-$C_6$ dialkylamino, halogen, cyano, and nitro; and M is selected from the group consisting of
—$(CH_2)_m$—O—$(CH_2)_l$—,
—$(CH_2)_m$—S—$(CH_2)_l$—,
—$(CH_2)_m$—$N(R^7)$—$(CH_2)_l$—,
—$(CH_2)_m$—$(CH_2)_l$—,
—$(CH_2)_m$—C(O)—$(CH_2)_l$—,
—$(CH_2)_m$—C(OH)—$(CH_2)_l$—,
—$(CH_2)_m$—$CHX^a$—$(CH_2)_l$—,
—$(CH_2)_m$—$CX^a_2$—$(CH_2)_l$—,
—$(CH_2)_m$—$N(R^7)C(O)$—$(CH_2)_l$—, and
—$(CH_2)_m$—$C(O)N(R^7)$—$(CH_2)_l$—, where m and l are each independently integers of from 1-3, $X^a$ is halogen, and $L^1$ comprises a cyclic moiety selected from the group consisting of
(ii) naphthyl, optionally substituted with 1-3 substituents independently selected from the group consisting of $R^7$, $OR^7$, $NR^7R^{7'}$, $C(O)R^7$, $C(O)OR^7$, $C(O)NR^7R^{7'}$, $NR^7C(O)R^{7'}$, $NR^7C(O)OR^{7'}$, halogen, cyano and nitro;
(iii) pyridyl, optionally substituted with 1-3 substituents independently selected from the group consisting of $R^7$, $OR^7$, $NR^7R^{7'}$, $C(O)R^7$, $C(O)OR^7$, $C(O)NR^7R^{7'}$, $NR^7C(O)R^{7'}$, $NR^7C(O)OR^{7'}$, halogen, cyano and nitro;
(iv) pyrimidinyl, optionally substituted with 1-3 substituents independently selected from the group consisting of $R^7$, $OR^7$, $NR^7R^{7'}$, $C(O)R^7$, $C(O)OR^7$, $C(O)NR^7R^{7'}$, $NR^7C(O)R^{7'}$, $NR^7C(O)OR^{7'}$, halogen, cyano and nitro;
(v) quinolinyl optionally substituted with 1-3 substituents independently selected from the group consisting of $R^7$, $OR^7$, $NR^7R^{7'}$, $C(O)R^7$, $C(O)OR^7$, $C(O)NR^7R^{7'}$, $NR^7C(O)R^{7'}$, $NR^7C(O)OR^{7'}$, halogen, cyano and nitro;
(vi) isoquinolinyl optionally substituted with 1-3 substituents independently selected from the group consisting of $R^7$, $OR^7$, $NR^7R^{7'}$, $C(O)R^7$, $C(O)OR^7$, $C(O)NR^7R^{7'}$, $NR^7C(O)R^{7'}$, $NR^7C(O)OR^{7'}$, halogen, cyano and nitro;

and each $R^7$ and $R^{7'}$ is independently
(a) hydrogen,
(b) $C_1$-$C_6$ linear, branched, or cyclic alkyl, optionally substituted with 1-3 substituents independently selected from the group consisting of $C_1$-$C_5$ linear or branched alkyl, up to perhalo substituted $C_1$-$C_5$ linear or branched alkyl, $C_1$-$C_3$ alkoxy and hydroxy;
(c) $C_1$-$C_6$ alkoxy, optionally substituted with 1-3 substituents independently selected from the group consisting of $C_1$-$C_5$ linear or branched alkyl, up to perhalo substituted $C_1$-$C_5$ linear or branched alkyl, $C_1$-$C_3$ alkoxy, hydroxy and halogen;

(d) phenyl, optionally substituted with 1-3 substituents independently selected from the group consisting of $C_1$-$C_5$ linear or branched alkyl, up to perhalo substituted $C_1$-$C_5$ linear or branched alkyl, $C_1$-$C_3$ alkoxy, hydroxy and halogen, (e) 5-6 membered monocyclic heteroaryl having 1-4 heteroatoms selected from the group consisting of O, N and S or 8-10 membered bicyclic heteroaryl having 1-6 heteroatoms selected from the group consisting of O, N and S, optionally substituted with 1-3 substituents independently selected from the group consisting of $C_1$-$C_5$ linear or branched alkyl, up to perhalo substituted $C_1$-$C_5$ linear or branched alkyl, $C_1$-$C_3$ alkoxy, hydroxy and halogen, (f) $C_1$-$C_3$ alkyl-phenyl, optionally substituted with 1-3 substituents independently selected from the group consisting of $C_1$-$C_5$, linear or branched alkyl, up to perhalo substituted $C_1$-$C_5$ linear or branched alkyl, $C_1$-$C_3$ alkoxy, hydroxy and halogen; and (g) up to perhalo substituted $C_1$-$C_5$ linear, branched or cyclic alkyl, and where not per-halo substituted, optionally substituted with 1-3 substituents independently selected from the group consisting of $C_1$-$C_5$ linear or branched alkyl, up to perhalo substituted $C_1$-$C_5$ linear or branched alkyl, $C_1$-$C_3$ alkoxy and hydroxy.

29. A compound of claim 28 wherein $L^1$ is pyridyl.

30. A compound as in claim 1 wherein A, A', A", L and $L^1$ follow one of the following of combinations:
- A=substituted pyridinyl, L=phenyl and $L^1$ is phenyl, pyridinyl, quinolinyl or isoquinolinyl,
- A=substituted pyridinyl, L=pyridinyl and $L^1$ is phenyl, pyridinyl, quinolinyl or isoquinolinyl,
- A'=isoquinolinyl, L=phenyl and $L^1$ is phenyl, pyridinyl, quinolinyl or isoquinolinyl,
- A'=isoquinolinyl, L=pyridinyl and $L^1$ is phenyl, pyridinyl, quinolinyl or isoquinolinyl,
- A'=quinolinyl, L=phenyl and $L^1$ is phenyl, pyridinyl, quinolinyl or isoquinolinyl,
- A'=quinolinyl, L=pyridinyl and $L^1$ is phenyl, pyridinyl, quinolinyl or isoquinolinyl,
- A"=substituted quinolinyl, L=phenyl and $L^1$=is phenyl, pyridinyl, quinolinyl or isoquinolinyl,
- A"=substituted quinolinyl, L=pyridinyl and $L^1$=is phenyl, pyridinyl, quinolinyl or isoquinolinyl.

31. A compound of claim 1, wherein either A, A', A", B, B' or B" is substituted by at least one hydroxy group.

32. A compound of claim 31, wherein B, B' and B" are, independently, a moiety of the formula -L(ML$^1$)$_q$, wherein $L^1$ is pyridinyl substituted by hydroxy.

33. A compound of claim 32, wherein the hydroxy group appears on the nitrogen of the pyridinyl moiety.

34. A compound according to claim 1, made by at least reducing a nitroaryl to an aryl amine.

35. A compound according to claim 1, made by at least converting a nitroaryl or an aniline into a corresponding arenesulfonyl chloride.

36. A compound according to claim 19, selected from the group consisting of:
- N-(4-tert-butylpyridinyl)-N'-(4-(4-pyridinylmethyl)phenyl) urea or a pharmaceutically acceptable salt thereof;
- N-(4-tert-butylpyridinyl)-N'-(4-phenoxyphenyl) urea or a pharmaceutically acceptable salt thereof;
- N-(4-tert-butylpyridinyl)-N'-(4-(4-methylphenoxy)phenyl) or a pharmaceutically acceptable salt thereof;
- N-(4-tert-butylpyridinyl)-N'-(4-(4-chlorophenoxy)phenyl) urea or a pharmaceutically acceptable salt thereof;
- N-(4-tert-butylpyridinyl)-N'-(4-(4-pyridinyloxy)phenyl) urea or a pharmaceutically acceptable salt thereof;
- N-(4-tert-butylpyridinyl)-N'-(4-(4-pyridinylthio)phenyl) urea or a pharmaceutically acceptable salt thereof; and
- N-(4-tert-butylpyridinyl)-N'-(3-(4-pyridinylthio)phenyl) urea or a pharmaceutically acceptable salt thereof.

37. A compound according to claim 19, selected from the group consisting of:
- N,N'-(bis(3-(2-methoxyquinolinyl)) urea) or a pharmaceutically acceptable salt thereof;
- N-(3-(2-methoxyquinolinyl)-N'-(4-(4-pyridinylmethyl) phenyl)) urea or a pharmaceutically acceptable salt thereof;
- N-(3-(2-methoxyquinolinyl)-N'-(4-(4-pyridinylcarbonyl) phenyl)) urea or a pharmaceutically acceptable salt thereof;
- N-(3-(2-methoxyquinolinyl)-N'-(4-(4-pyridinyloxy)phenyl)) urea or a pharmaceutically acceptable salt thereof;
- N-(3-(2-methoxyquinolinyl)-N'-(4-((4-methoxyphenyl) methylamino)phenyl)) urea or a pharmaceutically acceptable salt thereof; and
- N-(3-(2-methoxyquinolinyl)-N'-(3-(4-pyridinylthio)phenyl)) urea or a pharmaceutically acceptable salt thereof.

* * * * *

UNITED STATES PATENT AND TRADEMARK OFFICE
CERTIFICATE OF CORRECTION

PATENT NO. : 7,371,763 B2
APPLICATION NO. : 11/158048
DATED : May 13, 2008
INVENTOR(S) : Dumas et al.

It is certified that error appears in the above-identified patent and that said Letters Patent is hereby corrected as shown below:

On the Title Page, Item (75) Inventors, reads "(US); Timotthy B. Lowinger"
should read -- (US); Timothy B. Lowinger --

Column 40, line 13, reads "(OH)-, -$(CH_2)_mO$-, -$(CH_{2)m}S$-, -$(CH_2)_m$" should read
-- (OH)-, -$(CH_2)_mO$-, -$(CH_2)_mS$-, -$(CH_2)_m$, --

Column 40, line 14, reads "$N(R^7)$-, -$0(CH_2)_m$, -$CHX^a$-, -$CX^a_2$-, -S-" should read
-- $N(R^7)$-, -$O(CH_2)_m$-, -$CHX^a$-, -$CX^a_2$-, -S- --

Column 40, line 44, reads "five membered $C_{3-10}$ cycloalkyl having 0-3 heteroat-"
should read -- five-membered $C_{3-10}$ cycloalkyl having 0-3 heteroat- --

Column 40, line 50, reads "$C_7$-$C_{24}$ alkaryl, up to per halo substituted $C_7$-$C_4$ aralkyl,"
should read -- $C_7$-$C_{24}$ alkaryl, up to per halo substituted $C_7$-$C_{24}$ aralkyl, --

Column 40, line 52, reads "least 5 members and 1-3 heteratoms selected from 0, N"
should read -- least 5 members and 1-3 heteroatoms selected from O, N --

Column 41, line 2, reads "pyridyl groups substituted trifluoromethyl pyridyl" should
read -- pyridyl groups, substituted trifluoromethyl pyridyl --

Column 41, line 18, reads "-$OR^7$, -$SR^7$, -$NR^7R^{7,}$ $^{-NR^7}C(O)OR^{7'}$, -$NR^7C$" should read
-- -$OR^7$, -$SR^7$, -$NR^7R^{7'}$, -$NR^7C(O)OR^{7'}$, -$NR^7C$ --

Column 41, line 41, reads "substituted $C_{1-10}$ alkyl, substituted $C_{1-10}$ alkoxy, at least"
should read -- $C_{7-24}$ alkaryl, substituted $C_{1-10}$ alkyl, substituted $C_{1-10}$ alkoxy, at least --

Column 42, line 23, reads "phenyl, pyridinyl, substituted pyridinyl, pyrimidinyl
substi-" should read -- phenyl, pyridinyl, substituted pyridinyl, pyrimidinyl, substi- --

Signed and Sealed this
Twenty-eighth Day of December, 2010

David J. Kappos
*Director of the United States Patent and Trademark Office*

CERTIFICATE OF CORRECTION (continued)
U.S. Pat. No. 7,371,763 B2

Column 42, line 30, reads "per halo substituted $C_{1-10}$ alkoxy -O($R^7$), -$SR^7$, $NR^7R^{7}$" should read -- per halo substituted $C_{1-10}$ alkoxy, -O($R^7$), -$SR^7$, $NR^7R^7$ --

Column 42, line 45, reads "unsubstituted (triftuoromethyl) pyridyl groups, substi-" should read -- unsubstituted (trifluoromethyl) pyridyl groups, substi- --

Column 43, line 21, reads "groups, of A are selected from the group consisting of" should read -- groups of A are selected from the group consisting of --

Column 43, line 65, reads "$NR^7R^7$, -$NO_2$, $OR^7$, -$SR^7$, -$NR^7R^7$, -NRC(O)" should read -- $NR^7R^7$, -$NO_2$, $OR^7$, -$SR^7$, -$NR^7R^7$, -$NR^7C(O)$ --

Column 44, line 37, "13. A compound of claim 7 wherein $L^1$ is substituted 1 to" should read -- 13. A compound of claim 7, wherein $L^1$ is substituted 1 to --

Column 44, line 39, reads "consisting of $C_1$-$C_{10}$ alkyl, up to per halo substituted $C_1C_{10}$" should read -- consisting of $C_1$-$C_{10}$ alkyl, up to per halo substituted $C_1$-$C_{10}$ --

Column 44, line 42, reads " 14. A compound of claim 1 wherein each substituent J is" should read -- 14. A compound of claim 1, wherein each substituent J is --

Column 45, line 45, reads "urea or a pharmaceutically acceptable salt thereof" should read -- urea or a pharmaceutically acceptable salt thereof; --

Column 46, line 45, reads "$C_1$-$C_5$, linear or branched alkyl, $C_1$-$C_5$ linear or" should read -- $C_1$-$C_5$ linear or branched alkyl, $C_1$-$C_5$ linear or --

Column 47, line 32, reads "-$(CH_2)_m$-C(OH)-$(CH_2)_1$-," should read -- $(CH_2)_m$-CH(OH)-$(CH_2)_1$-, --

Column 47, line 49, reads "perhalo substituted $C_1C_5$ linear or branched alkyl," should read -- perhalo substituted $C_1$-$C_5$ linear or branched alkyl, --

Column 48, line 15, reads "-N($R^7$)($CH_2$)-, -C(O)$CH_2$, -$CH_2$OC(O)-," should read -- -N($R^7$)($CH_2$)-, -C(O)$CH_2$-, -$CH_2$OC(O)- --

Column 48, line 16, reads "-C(O)O$CH_2$-,-C(O)N($R^7$)$CH_2$-, -N(R7)C(O)" should read -- -C(O)O$CH_2$-, -C(O)N($R^7$)$CH_2$-, -N($R^7$)C(O) --

Column 48, line 22, reads "$R^7OR^7$, $NR^7R^7$, C(O)$NR^7R^7$, $NR^7C(O)R^7$, $NR^7C(O)$" should read -- $R^7$, $OR^7$, $NR^7R^7$, C(O)$NR^7R^7$, $NR^7C(O)R^7$, $NR^7C(O)$ --

Column 49, line 24, reads "-$(CH_2)_m$-C(OH) -$(CH_2)_1$–," should read -- -$(CH_2)_m$-CH(OH) -$(CH_2)_1$–, --

Column 50, line 21, reads "–$(CH_2)_m$–C(OH) –$(CH_2)_1$–," should read -- –$(CH_2)_m$–CH(OH) –$(CH_2)_1$–, --

Column 50, line 30, reads "consisting of" should read -- consisting of: --

Column 50, line 56, reads "and each $R^7$ and $R^7$ is independently" should read -- and each $R^7$ and $R^{7'}$ is independently --

Column 51, line 17, reads "consisting of $C_1$-$C_5$, linear or branched alkyl, up to" should read -- consisting of $C_1$-$C_5$ linear or branched alkyl, up to --

Column 51, line 29, reads "follow one of the following of combinations:" should read -- follow one of the following combinations: --

Column 51, line 42, reads "A"=substituted quinolinyl, L=phenyl and $L^1$=is phenyl," should read -- A"=substituted quinolinyl, L=phenyl and $L^1$ is phenyl, --

Column 51, line 44, reads "A"=substituted quinolinyl, L=phenyl and $L^1$=is phenyl," should read -- A"=substituted quinolinyl, L=phenyl and $L^1$ is phenyl, --